(12) United States Patent
Low et al.

(10) Patent No.: US 9,279,813 B2
(45) Date of Patent: Mar. 8, 2016

(54) EX VIVO FLOW CYTOMETRY METHOD AND DEVICE

(71) Applicant: Purdue Research Foundation, West Lafayette, IN (US)

(72) Inventors: Philip Stewart Low, West Lafayette, IN (US); Wei He, West Lafayette, IN (US); Sumith A. Kularatne, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 22 days.

(21) Appl. No.: 14/187,844

(22) Filed: Feb. 24, 2014

(65) Prior Publication Data

US 2014/0234866 A1   Aug. 21, 2014

Related U.S. Application Data

(62) Division of application No. 12/513,028, filed as application No. PCT/US2007/023176 on Nov. 2, 2007, now Pat. No. 8,685,752.

(60) Provisional application No. 60/856,667, filed on Nov. 3, 2006, provisional application No. 60/956,562, filed on Aug. 17, 2007.

(51) Int. Cl.
*G01N 33/574* (2006.01)
*G01N 33/58* (2006.01)
(Continued)

(52) U.S. Cl.
CPC .......... *G01N 33/582* (2013.01); *G01N 33/5091* (2013.01); *G01N 33/574* (2013.01); *G01N 33/57434* (2013.01); *G01N 15/1459* (2013.01);
(Continued)

(58) Field of Classification Search
CPC .............. G01N 33/582; G01N 33/574; G01N 33/57434; G01N 33/5091
See application file for complete search history.

(56) References Cited

U.S. PATENT DOCUMENTS 2,816,110 A   12/1957   Sletzinger et al.
4,577,636 A   3/1986    Spears
(Continued)

FOREIGN PATENT DOCUMENTS

CA   2520406    10/2004
CA   2666234    5/2008
(Continued)

OTHER PUBLICATIONS

NCBI, MeSH definition for Indocarbocyanine Green, 2 pages, Aug. 31, 2008.
(Continued)

*Primary Examiner* — Gail R Gabel
(74) *Attorney, Agent, or Firm* — Barnes & Thornburg LLP

(57) ABSTRACT

The invention relates to a method for diagnosing a disease state mediated by pathogenic cells. The method comprises the steps of combining with an ex vivo patient sample a composition comprising a conjugate or complex of the general formula $$A_b\text{-}X$$

wherein the group $A_b$ comprises a ligand that binds to the pathogenic cells and the group X comprises an imaging agent, and detecting the pathogenic cells that express a receptor for the ligand using flow cytometry.

19 Claims, 19 Drawing Sheets

(51) Int. Cl.
*G01N 33/50* (2006.01)
*G01N 15/14* (2006.01)
*G01N 15/10* (2006.01)

(52) U.S. Cl.
CPC .... *G01N 15/1463* (2013.01); *G01N 2015/1006* (2013.01); *G01N 2015/149* (2013.01); *G01N 2015/1438* (2013.01); *G01N 2458/00* (2013.01)

(56) References Cited

U.S. PATENT DOCUMENTS

| | | |
|---|---|---|
| 4,641,650 A | 2/1987 | Mok |
| 4,713,249 A | 12/1987 | Schroder |
| 4,718,417 A | 1/1988 | Kittrell et al. |
| 4,785,806 A | 11/1988 | Deckelbaum |
| 4,817,601 A | 4/1989 | Roth et al. |
| 4,850,351 A | 7/1989 | Herman et al. |
| 4,917,084 A | 4/1990 | Sinofsky |
| 4,950,266 A | 8/1990 | Sinofsky |
| 5,094,848 A | 3/1992 | Brixner |
| 5,108,921 A | 4/1992 | Low et al. |
| 5,140,104 A | 8/1992 | Coughlin et al. |
| 5,192,525 A | 3/1993 | Yang et al. |
| 5,217,456 A | 6/1993 | Narciso |
| 5,266,333 A | 11/1993 | Cady et al. |
| 5,275,594 A | 1/1994 | Baker et al. |
| 5,336,506 A | 8/1994 | Josephson et al. |
| 5,373,093 A | 12/1994 | Vallarino et al. |
| 5,399,338 A | 3/1995 | Born et al. |
| 5,416,016 A | 5/1995 | Low et al. |
| 5,417,982 A | 5/1995 | Modi |
| 5,547,668 A | 8/1996 | Kranz et al. |
| 5,552,545 A | 9/1996 | Pearce et al. |
| 5,562,100 A | 10/1996 | Kittrell et al. |
| 5,576,305 A | 11/1996 | Ratcliffe |
| 5,688,488 A | 11/1997 | Low et al. |
| 5,753,631 A | 5/1998 | Paulson et al. |
| 5,759,546 A | 6/1998 | Weinberg et al. |
| 5,820,847 A | 10/1998 | Low et al. |
| 6,093,382 A | 7/2000 | Wedeking et al. |
| 6,167,297 A | 12/2000 | Benaron |
| 6,204,371 B1 | 3/2001 | Levinson |
| 6,217,847 B1 | 4/2001 | Contag et al. |
| 6,221,334 B1 | 4/2001 | Wedeking et al. |
| 6,246,901 B1 | 6/2001 | Benaron |
| 6,270,766 B1 | 8/2001 | Feldman et al. |
| 6,335,434 B1 | 1/2002 | Guzaev et al. |
| 6,365,362 B1 | 4/2002 | Terstappen et al. |
| 6,387,350 B2 | 5/2002 | Goldenberg |
| 6,507,747 B1 | 1/2003 | Gowda et al. |
| 6,780,984 B2 | 8/2004 | Wang et al. |
| 6,782,289 B1 | 8/2004 | Strauss |
| 6,960,449 B2 | 11/2005 | Wang et al. |
| 7,033,594 B2 | 4/2006 | Low et al. |
| 7,128,893 B2 | 10/2006 | Leamon et al. |
| 7,223,380 B2 | 5/2007 | Yang et al. |
| 7,381,535 B2 * | 6/2008 | Perez et al. ................. 435/7.21 |
| 7,601,332 B2 | 10/2009 | Vlahov |
| 7,740,854 B2 | 6/2010 | Low et al. |
| 7,977,058 B2 | 7/2011 | Low et al. |
| 8,043,602 B2 | 10/2011 | Jallad et al. |
| 8,043,603 B2 | 10/2011 | Kennedy et al. |
| 8,383,354 B2 | 2/2013 | Low et al. |
| 8,388,977 B2 | 3/2013 | Low et al. |
| 8,586,595 B2 | 11/2013 | Low et al. |
| 8,685,752 B2 * | 4/2014 | Low et al. .................. 436/505 |
| 2001/0031252 A1 | 10/2001 | Low et al. |
| 2002/0127181 A1 | 9/2002 | Edwards et al. |
| 2002/0192157 A1 | 12/2002 | Low et al. |
| 2003/0162234 A1 | 8/2003 | Jallad et al. |
| 2003/0198643 A1 | 10/2003 | Lu |
| 2003/0219375 A1 | 11/2003 | Piwnica-Worms |
| 2004/0033195 A1 | 2/2004 | Leamon et al. |
| 2004/0057900 A1 | 3/2004 | Edwards et al. |
| 2004/0136910 A1 | 7/2004 | Jallad et al. |
| 2004/0184990 A1 | 9/2004 | Larsen et al. |
| 2004/0242582 A1 | 12/2004 | Green et al. |
| 2005/0002942 A1 | 1/2005 | Vlahov et al. |
| 2005/0026866 A1 | 2/2005 | Pawelek |
| 2005/0227985 A9 | 10/2005 | Green et al. |
| 2005/0244336 A1 | 11/2005 | Low |
| 2006/0002891 A1 | 1/2006 | Pouletty |
| 2006/0067946 A1 | 3/2006 | Low et al. |
| 2006/0134002 A1 | 6/2006 | Lin |
| 2006/0182687 A1 | 8/2006 | Yang et al. |
| 2006/0204565 A1 | 9/2006 | Low et al. |
| 2007/0009434 A1 | 1/2007 | Low et al. |
| 2007/0031334 A1 | 2/2007 | Leamon et al. |
| 2007/0231266 A1 | 10/2007 | Low et al. |
| 2007/0276231 A1 | 11/2007 | Low et al. |
| 2008/0119475 A1 | 5/2008 | Low et al. |
| 2008/0138396 A1 | 6/2008 | Low et al. |
| 2008/0254499 A1 | 10/2008 | Low et al. |
| 2008/0311037 A1 * | 12/2008 | Heston et al. ................. 424/1.85 |
| 2009/0012009 A1 | 1/2009 | Low et al. |
| 2010/0055735 A1 | 3/2010 | Low et al. |
| 2010/0322854 A1 | 12/2010 | Low et al. |
| 2011/0044897 A1 | 2/2011 | Low et al. |
| 2011/0189086 A1 | 8/2011 | Low et al. |
| 2012/0003151 A1 | 1/2012 | Low et al. |
| 2012/0276191 A1 | 11/2012 | Low et al. |
| 2013/0101519 A1 | 4/2013 | Low et al. |
| 2013/0336895 A1 | 12/2013 | Jallad et al. |
| 2013/0344002 A1 | 12/2013 | Jallad et al. |
| 2014/0056809 A1 | 2/2014 | Low et al. |
| 2014/0065066 A1 | 3/2014 | Low et al. |
| 2014/0112866 A1 | 4/2014 | Low et al. |

FOREIGN PATENT DOCUMENTS

| | | | |
|---|---|---|---|
| EP | 0220030 | 10/1986 | |
| EP | 0273085 | 12/1986 | |
| EP | 1940473 | 7/2008 | |
| JP | 2774378 | 7/1998 | |
| JP | 2003-515570 | 5/2003 | |
| RU | 2123338 | 11/1996 | |
| RU | 2101703 | 10/1998 | |
| WO | 90/12096 | 10/1990 | |
| WO | 91/19501 | 12/1991 | |
| WO | 91/19502 | 12/1991 | |
| WO | 92/13572 | 2/1992 | |
| WO | 96/22521 | 7/1996 | |
| WO | 96/36367 | 11/1996 | |
| WO | 97/37690 | 10/1997 | |
| WO | 98/49196 | 11/1998 | |
| WO | 99/41285 | 8/1999 | |
| WO | 00/73332 | 12/2000 | |
| WO | 01/19320 | 3/2001 | |
| WO | 01/039806 | 6/2001 | |
| WO | 01/47552 | 7/2001 | |
| WO | 01/074382 | 10/2001 | |
| WO | 01/091807 | 12/2001 | |
| WO | 02/087424 | 11/2002 | |
| WO | 2004/044227 | 5/2004 | |
| WO | 2004/069159 | 8/2004 | |
| WO | 04/110250 | 12/2004 | |
| WO | WO 2004/0110250 | * 12/2004 | ........... G01N 33/567 |
| WO | 2005/049579 | 6/2005 | |
| WO | 2005/067644 | 7/2005 | |
| WO | 2005/087275 | 9/2005 | |
| WO | 2006/012527 | 2/2006 | |
| WO | 2006/034046 | 3/2006 | |
| WO | 2006/065943 | 6/2006 | |
| WO | 2006/071754 | 7/2006 | |
| WO | 2006/018454 | 9/2006 | |
| WO | 2007/001466 | 1/2007 | |
| WO | 2007/006041 | 1/2007 | |
| WO | WO 2007/038346 | 4/2007 | |
| WO | 2008/057437 | 5/2008 | |
| WO | 2008/098112 | 8/2008 | |
| WO | 2008/148001 | 12/2008 | |
| WO | 2009/002993 | 12/2008 | |
| WO | 2009/026177 | 2/2009 | |

(56) References Cited

FOREIGN PATENT DOCUMENTS

OTHER PUBLICATIONS

"Macrophages" from Wikipedia, updated Nov. 18, 2007.
Achilefu et al., "Novel Receptor-Targeted Fluorescent Contrast Agents for In Vivo Tumor Imaging", Investigative Radiology, vol. 35, No. 8, pp. 479-485, Aug. 2000.
Antohe et al., "Increased uptake of folate conjugates by activated macrophages in experimental hyperlipemia", Cell Tissue Research, vol. 320, No. 2, pp. 277-285, May 2005.
Aviram et al., "Intralipid infusion abolishes ability of human serum to cholesterol-load cultured macrophages", Arteriosclerosis, vol. 9, pp. 67-75, 1989.
Ballou et al., "Tumor labeling in vivo using cyanine-conjugated monoclonal antibodies", Cancer Immunol Immunother, vol. 41, pp. 257-263, 1995.
Barrera et al., "Synovial macrophage depletion with clodronate-containing liposomes in rheumatoid arthritis", Arthritis and Rheumatism, vol. 43, pp. 1951-1959, 2000.
Beaumont et al., "Selective Fluorodenitration of Chloronitroaromatics", J. Fluorine Chem., vol. 63, pp. 25-30, 1993.
Becker et al., "Macromolecular Contrast Agents for Optical Imaging of Tumors: Comparison of Indotricarbocyanine-labeled Human Serum Albumin and Transferrin", Photochemistry and Photobiology, vol. 72, No. 2, pp. 234-241, May 14, 2000.
U.S. Appl. No. 61/235,220, filed Aug. 19, 2009, Low et al.
U.S. Appl. No. 61/157,847, filed Mar. 5, 2009, Low et al.
Bettio et al, "Synthesis and Preclinical Evaluation of a Folic Acid Derivative Labeled with 18F for PET Imaging of Folate Receptor-Positive Tumors", The Journal of Nuclear Medicine, vol. 47, No. 7, pp. 1153-1160, 2006.
Bock et al., "Sulfonamide Structure-Activity Relationships in a Cell-Free System. 2. Proof for the Formation of a Sulfonamide-Containing Folate Analog", Journal of Medicinal Chemistry, vol. 17, No. 1, pp. 23-28, 1974.
Boechat et al., Fluorodenitrations Using Tetramethylammonium Fluoride, J. Soc. Chem, Commun., pp. 921-992, 1993.
Boente et al., "Screening, imaging, and Early Diagnosis of Ovarian Cancer", Clinical Obstetrics and Gynecology, vol. 37, No. 2, pp. 377-391, Jun. 1994.
Bonasera et al., "The Synthesis of [26, 27-11C]Dihydroxyvitamin D3, a Tracer for Positron Emission, Tomography (PET), Bioorganic & Medicinal Chemistry", Elsevier Science Ltd., vol. 9, pp. 3123-3128, 2001.
Budinger et al., "New Approaches to Targeting Arthritis with Radiopharmaceuticals", The Journal of Rheumatology, 22(1) Supp: 62-67, 1995.
Burke et al., "Book Review. The Macrophage", British Journal of Cancer, vol. 89, p. 421, 2003.
Campbell et al., "Folate-binding Protein is a Marker for Ovarian Cancer", Cancer Research, vol. 51, pp. 5329-5338, Oct. 1991.
Canis et al., "Lapascopic Diagnosis of Adnexal Cystic Masses: A 12-Year Experience With Long-Term Follow-Up", Obstetrics & Gynecology, vol. 83, No. 5, pp. 707-712, May 1994.
Case, "Ultrasound Physics and Instrumentation, Surgical Clinics of North America", vol. 78, No. 2, pp. 197-217, Apr. 1998.
Chen et al., "MicroPET Imaging of Brain Tumor Angiogenesis with 18F-Labeled PEGylated RGD Peptide", European Journal of Nuclear Medicine and Molecular Imaging, vol. 31, No. 8, pp. 1081-1089, Aug. 2004.
Tung et al., "Preparation of a Cathepsin D Sensitive Near-Infrared Fluorescence Probe for Imaging", American Chemical Society, vol. 10, No. 5, pp. 692-696, 1999.
Cochlovius, "Therapeutic Antibodies", Modern Drug Discovery, pp. 33-38, 2003.
Cohen et al., "Screening for ovarian cancer: The role of noninvasive imaging techniques", Am J. Obstet Gynecol., vol. 170, No. 4, pp. 1088-1094, 1994.

Cohen et al., "Three-Dimensional Power Doppler Ultrasound Improves the Diagnostic Accuracy for Ovarian Cancer Prediction", Gynecologic Oncology, vol. 82, pp. 40-48, 2001.
Cox et al., "Anhydrous, Tetrabutylammonium Fluoride: A Mild but Highly Efficient Source of Nucleophilic Fluoride Ion", J. Org. Chem., No. 49, pp. 3216-3219, 1984.
Degrado et al., "Synthesis and Evaluation of (18)F-Labeled Choline Analogs as Oncologic PET Tracers", J. Nuclear Medicine, vol. 42, No. 12, pp. 1805-1814, 2001.
DePriest et al., "Transvaginal Sonography as a Screening Method for the Detection of Early Ovarian Cancer", Gynecologic Oncology, vol. 65, No. GO974705, pp. 408-414, 1997.
U.S. Appl. No. 12/526,096, filed Aug. 6, 2009, Low et al.
Feldman et al., "Anti-TNFa Therapy Is Useful in Rheumatoid Arthritis and Crohn's Disease: Analysis of the Mechanism of Action Predicts Utility in Other Diseases", Transplant. Proc. , 30, pp. 4126-4127, 1998.
Forstner et al., "CT and MRI of ovarian cancer", Abdominal Imaging, vol. 20, pp. 2-8, 1995.
Garg et al., "Fluorine-18 Labeling of Monoclonal Antibodies and Fragments with Preservation of Immunoreactivity", Bioconjugate Chem., vol. 2, No. 1, pp. 44-49, 1991.
Giroldo et al., "An Unusually Fast Nucleophilic Aromatic Displacement Reaction: The Gas-Phase Reaction of Fluoride Ions with Nitrobenzene", Angew. Chem. Int. Ed., No. 43, pp. 3588-3590, 2004.
Godwin et al., "The synthesis of biologically active pteroyloligo-g-L-glutamates (folic acid conjugates): Evaluation of (3H) pteroylheptaglutamate for metabolic studies", Journal of Biological Chemistry. vol. 247, pp. 2266-2271, Apr. 1974.
Gotoh, "Causes and treatment of rheumatoid arthritis; recent trend I. Progress in pathogenesis of rheumatoid arthritis; role of macrophages and dendritic cells", Pharma Nedica, Japan Medical Review Co., Ltd., Tokyo, 17(10): 35-39, 1999.
Greenman, Y., et al., "Heterogeneous Expression of Two Somatostatin Receptor Subtypes in Pituitary Tumors," Journal of Clinical Endocrinology and Metabolism, vol. 78, No. 2, pp. 398-403, 1994.
Hamacher et al., "No-Carrier-Added Nucleophilic 18F-Lavelling in an Electrochemical Cell Exemplified by the Routine Production of [18F]altanserin", Applied Radiation and Isotopes, No. 64, pp. 989-994, 2006.
Harris et al., "Human leukemic models of myelomonocytic development: a review of the HL-60 and U937 cell lines", Journal of Leukocyte Biology, vol. 37., No. 4, pp. 407-422, 1985.
Holmgren et al., "Strategies for the Induction of Immune Responses at Mucosal Surfaces Making Use of Cholera Toxin B Subunit As Immunogen, Carrier, and Adjuvant", Am. J. Trop Med Hyd, 50, pp. 42-54, 1994.
Hynes et al., "Quinazolines as Inhibitors of Dihydrofolate Reductase. 4. Classical Analogues of Folic and Isofolic Acids", Journal of Medicinal Chemistry, vol. 20, No. 4, pp. 588-591, 1977.
Jager et al., "Resection guided by antibodies (REGAJ): a diagnostic procedure during second-look operation in ovarian cancer patients", Depts of Obstetrics, Gynecology and Nuclear Medicine, Univ of Erlangen-Nurnberg, pp. 18-20, 1990.
Johnstrom et al., "18F-Endothelin-1, a Positron Emission Tomography (PET) Radioligand for the Endothelin Receptor System: Radiosynthesis and In Vivo Imaging Using MicroPET", Clinical Science, vol. 103, Suppl. 48, pp. 45-85, 2002.
Karlan, "The Status of Ultrasound and Color Doppler Imaging for the Early Detection of Ovarian Cancer", Cancer Investigation, vol. 15, No. 3, pp. 265-269, 1997.
Karlan et al., "Ovarian Cancer Screening: The Role of Ultrasound in Early Detection", Cancer Supplement, vol. 76, No. 10, pp. 2011-2015, Nov. 1995.
Karsten et al., "Towards Usage-Based Accounting: Applying Policy-Based Intelligent Agents, ITC 15". Elsevier Science B.V., pp. 633-642, 1997.
Kennedy et al., "Evaluation of Folate Conjugate Uptake and Transport by the Choroid Plexus of Mice", Pharmaceutical Research, vol. 20, No. 5, p. 714-719, May 2003.

(56) References Cited

OTHER PUBLICATIONS

Kennedy et al., "Optical imaging of metastatic tumors using a folate-targeted fluorescent probe", J. of Biomedical Optics, vol. 8, No. 4, pp. 636-641, Oct. 2003.
Kim et al., "Synthesis and Biological Activity of 10-Thia-10-deaza Analogs of Folic Acid, Pteroic Acid, and Related Compounds", Journal of Medicinal Chemistry, vol. 18, No. 8, pp. 776-780, 1975.
Kinne et al., "Macrophage in rheumatoid arthritis", Arthritis Research, vol. 2, No. 3, pp. 189-202, 2000.
Konda et al., "Development of a Tumor-Targeting MR Contrast Agent Using the High-Affinity Folate Receptor", Investigative Radiology, vol. 35, No. 1, pp. 50-57, 2000.
Kramer, "Basic Principles of Magnetic Resonance Imaging", Radiological Clinics of North America, vol. 22, No. 4, pp. 765-778, Dec. 1984.
Kuroiwa et al., "Development of a Fluorescein Operative Microscope for Use During Malignant Glioma Surgery", Elsevier Science Inc., vol. 50, pp. 41-49, 1998.
Leamon et al., "Folate-mediated targeting: from diagnosis to drug and gene therapy", DDT vol. 6 No. 1 44-51, Jan. 2001.
Leamon et al., "Synthesis and Biological Evaluation of EC140: A Novel Folate—Targeted Cinca Alkaloid Conjugate", Bioconjugate Chem., vol. 17, No. 5, pp. 1226-1232, 2006.
Leamon et al., "Synthesis and Biologicial Evaluation of EC20: A New Folate-Derived, 99mTc-Based Radiopharmaceutical", Bioconjugate Chemistry, vol. 13, No. 6, pp. 1200-1210, 2002.
Leamon et al., "Selective Targeting of Malignant Cells with Cytotoxin-Folate Conjugates", J. Drug Targeting 2: 101-112, 1994.
Lee et al., "Folic Acid Antagonists. Methotrexate Analogs Containing Spurious Amino Acids. Dichlorohomofolic Acid", Journal of Medicinal Chemistry, vol. 17, No. 3, pp. 326-330, 1974.
Lemaire et al., "Fluorine-18-Altanserin: A Radioligand for the Study of Serotonin Receptors with PET: Radiolabeling and In Vivo Biologic Behavior in Rats", The Journal of Nuclear Medicine. vol. 32, No. 12, pp. 2266-2272, Dec. 1991.
Licha et al., "Hydrophilic Cyanine Dyes as Contrast Agents for Near-infrared Tumor Imaging: Synthesis, Photophysical Properties and Spectroscopic In vivo Characterization", Photochemistry and Photobiology, vol. 72, No. 3, pp. 392-398, 2000.
Liotta et al., "The Chemistry of "Naked" Anions. I. Reactions of the 18-Crown-6 Complex of Potassium Fluoride with Organic Substrates in Aprotic Organic Solvents", Journal of American Chemical Society, vol. 96, No. 7, pp. 2250-2252, Apr. 3, 1974.
Liu-Wu et al., "Identification and Analysis of Macrophage-Derived Foam Cells from Human Atherosclerotic Lesions by Using a 'Mock' FL3 Channel in Flow Cytometry", Cytometry, vol. 29, No. 2, pp. 155-164, 1997.
Low et al., "Ovarian Cancer: Comparison of findings with Perfluorocarbon-enhanced MR Imaging, In-111-CYT-103 Immunoscintigraphy, and CT", Depts of Diagnostic Rad and Onc, Sharp Memorial Hospital, vol. 195, No. 2, pp. 391-400, 1995.
Lu et al., "Folate-Targeted Enzyme Prodrug Cancer Therapy Utilizing Penicillin-V Amidase and a Doxorubicin Prodrug", J. Drug Targeting 7:43-53, 1999.
Mahmood et al, "Near Infrared Optical Imaging for Protease Activity for Tumor Detection", Radiology, 213:866-870, 1999.
Maiman et al., "Laproscopic Excision of Ovarian Neoplasm Subsequently Found to Be Malignant", Obstetrics & Gynecology, vol. 77, No. 4, pp. 563-565, Apr. 1991.
U.S. Appl. No. 60/956,489, filed Aug. 17, 2007, Low et al.
Mancini et al., "Relative contributions of apolipoprotein A and apolipoprotein B to the development of fatty lesions in the proximal aorta of mice", Arterioscler. Thromb. Vasc. Biol., vol. 15, pp. 1911-1916, 1995.
Mathias et al., "Preparation of 66Ga- and 68GA-labeled Ga(III)-deferoxamine-folate as potential folate-receptor-targeted PET radiopharmaceuticals", Nuclear Medicine and Biology, vol. 30, pp. 725-731, 2003.

Matsuyama et al., "Clinical significance of the folate receptor beta expression in rheumatoid synovial macrophages", Rheumatoid, Japan College of Rheumatology, 41(2): 265, 2001.
Matsuyama et al., "Activation and pathological significance of macrophages in rheumatoid synovitis", Clinical Immunity, Japan, Kagaku Hyoronsha, Tokyo, 30(2): 214-219, 1998.
Mestas et al. "Of Mice and Not Men: Differences between Mouse and Human Immunology", J. of Immunology, 172, pp. 2731-2738, 2004.
Mukasa et al., "Function analysis of folate receptor-β in a RA synovial membrane macrophage cell line", Rheumatoid, Japan College of Rheumatology, 40(2): 378, 2000.
Mulherin et al., "Synovial tissue macrophage populations and articular damage in rheumatoid arthritis", Arthritis and Rheumatism, vol. 39, No. 1, pp. 115-124, 1996.
Murakami et al., "18F-Labelled Annexin V: A PET Tracer for Apoptosis Imaging", European Journl of Nuclear Medicine and Molecular Imaging, vol. 31, No. 4, pp. 469-474, Apr. 2004.
Nagayoshi et al., "Effectiveness of Anti-Folate Receptor β Antibody Conjugated with Truncated *Pseudomonas* Exotoxin in the Targeting of Rheumatoid Arthritis Synovial Macrophages", Arthritis and Rheumatism, vol. 52, pp. 2666-2675, Sep. 2005.
Nair et al., "Folate Analogues Altered in the C9-N10 Bridge Region. 10-Oxafolic Acid and 10-Oxaaminopterin", Journal of Medicinal Chemistry, vol. 19, No. 6, pp. 825-829, 1976.
Nair et al., "Folate Analogues Altered in the C9-N10 Bridge Region: N10-Tosylisohomofolic Acid and N10-Tosylisohomoaminopterin", Journal of Medicinal Chemistry, vol. 21, No. 7, pp. 673-677, 1978.
Nair et al., "Folate Analogues Altered in the C9-N10 Bridge Region: 11-Thiohomofolic Acid", Journal of Medicinal Chemistry, vol. 22, No. 7, pp. 850-855, 1979.
Nair et al., "Folate Analogues Altered in the C9-N10 Bridge Region. 14. 11-Oxahomofolic Acid, a Potential Antitumor Agent", Journal of Medicinal Chemistry, vol. 23, pp. 59-65, 1980.
Nair et al., "Folate Analogues Altered in the C9-N10 Bridge Region. 18. Synthesis and Antitumor Evaluation of 11-Oxahomoaminopterin and Related Compounds", Journal of Medicinal Chemistry, vol. 24, pp. 1068-1073, 1981.
Nair et al., "Folate Analogues. 20. Synthesis and Antifolate Activity of 1, 2, 3, 4, 5, 6,—Hexahydrohomofolic Acid", Journal of Medicinal Chemistry, vol. 26, pp. 135-140, 1983.
Nair et al., "Folate Analogues. 21. Synthesis and Antifolate and Antitumor Activities of N10- (Cyanomethyl)- 5,8-dideazafolic Acid", Journal of Medicianal Chemistry, vol. 26, pp. 605-607, 1983.
Nair et al., "Folate Analogues. 22. Synthesis and Biological Evaluation of Two Analogues of Dihydrofolic Acid Processing a 7,8-Dihydro-8-oxapterin Ring System", Journal of Medicinal Chemistry, vol. 26, 1164-1168, 1983.
Nakashima-Matsushita et al, "Selective expression of folate receptor beta and its possible role in methotrexate transport in synovial macrophages from patients with rheumatoid arthritis", Arthritis Rheum. 42(8): 1609-1616, 1999.
Nehzat et al. "Four ovarian cancers diagnosed during laproscopic management of 1011 women with adnexal masses", Am J Obstet Gynecol., vol. 167, No. 3, pp. 790-796, Sep. 1992.
Oatis et al., "Synthesis of Quinazoline Analogues of Folic Acid Modified at Position 10", Journal of Medicinal Chemistry, vol. 20, No. 11, pp. 1393-1396, 1977.
Olma et al., "4-[18F]fluorophenyl ureas via carbamate-4-nitrophenyl esters and 4-[18F]Fluoroaniline", Journal of Labeled Compd. And Radiopnarm, vol. 49, pp. 1037-1050, 2006.
Paigen et al., "Variation in susceptibility to atherosclerosis among inbred strains of mice", Atherosclerosis, vol. 57, No. 1, pp. 65-73, 1985.
Pasterkamp et al. "Techniques characterizing the coronary atherosclerotic plaque: Influence on clinical decision making'?", J. Amer. Coll. Cardiol. 36:13-21, 2000.
Paulos et al. "Folate Receptor-Mediated Targeting of Therapeutic and Imaging Agents to Activated Macrophages in Rheumatoid Arthritis", Advanced Drug Delivery Reviews, vol. 56, No. 8, pp. 1205-1217, 2004.

(56) References Cited

OTHER PUBLICATIONS

Pelegrin et al., "Antibody-Fluorescein Conjugates for Photoimmunodiagnosis of Human Colon Carcinoma in Nude Mice", Institute of Biochemistry, University of Lausanne, vol. 67, No. 10, pp. 2529-2537, 1991.
Plante et al., "Polyglutamyl and Polylysyl Derivatives of the Lysine Analogues of Folic Acid and Homofolic Acid", Journal of Medicinal Chemistry, vol. 19, No. 11, pp. 1295-1299, 1976.
Rampone et al., "Ovarian cancer screening by transvaginal color Doppler ultrasonography", Minerva Ginecologica, vol. 53, Suppl. 1 al N 1, pp. 125-128, 2001.
Reddy et al., "Optimization of Folate-Conjugated Liposomal Vectors for Folate Receptor-Mediated Gene Therapy", J. Pharm. Sciences 88: 1112-1118, 1999.
Reddy et al., "Folate-Mediated Targeting of Therapeutic and Imaging Agents to Cancers", Critical Reviews in Ther. Drug Carrier Systems 15: 587-627, 1998.
Reddy et al., "Folate receptor specific anti-tumor activity of folate-mitomycin conjugates", Cancer Chemother. Pharmacol., 58(2): 229-36, 2006.
Reles et al., "Transvaginal Color Doppler Sonography and Conventional Sonography in the Preoperative Assessment of Adnexal Masses", Journal of Clinical Ultrasound, vol. 25, No. 5, pp. 217-225, Jun. 1997.
Roberts et al., "Folic Acid Analogs. Modifications in the Benzene-Ring Region. 2. Thiazole Analogs", Journal of Medicinal Chemistry, 15 (12): 1310-1312, 1972.
Roberts et al., "Folic Acid Analogs. Modifications in the Benzene-Ring Region. 1. 2'- and 3'—Azafolic Acids", Journal of Medicinal Chemistry, 14(2): 125-130, 1971.
Roberts et al., "Folic Acid Analogs. Modifications in the Benzene-Ring Region. 4. 3'-Ethyl - and 3'—Isopropylfolic Acids", Journal of Medicinal Chemistry, vol. 17, No. 2, pp. 219-222, 1974.
Rouzi et al., "Lapascopic Ovarian Cystectomy: Selection of Patients and Consequences of Rupture of Ovarian Malignancy", Annals of Saudi Medicine, vol. 17, No. 3, pp. 321-325, 1997.
Rudd et al., "Imaging Atherosclerotic Plaque Inflammation with [<18>F]-Fluorodeoxyglucose Positron Emission Tomography", Circulation, vol. 105, No. 23, pp. 2709-2710, 2002.
Sato et al., "Usefulness of Mass Screening for Ovarian Carcinoma Using Transvaginal Ultasonography", American Cancer Society, vol. 89, No. 3, pp. 582-588, Aug. 2000.
Sevick-Muraca et al., "Fluorescence and Absorption Contrast Mechanisms for Biomedical Optical Imaging Using Frequency-Domain Techniques", Photochemistry and Photobiology, vol. 66, No. 1, pp. 55-645, 1997.
Sheski et al., "Endoscopic Treatment of Early-Stage Lung Cancer", Division of Pulmonary, Allergy, Care, and Occupational Medicine at IU School of Medicine, vol. 7, No. 1, pp. 35-44, Jan./Feb. 2000.
Shoup et al., "Synthesis of Fluorine-18-Labeled Biotin Derivatives: Biodistribution and Infection Localization", J. Nuclear Medicine, vol. 35, No. 10, pp. 1685-1690, 1994.
Sijtsema et al., "Confocal Direct Imaging Raman Microscope: Design and Application in Biology", Applied Spectroscopy, vol. 52, Issue 3, pp. 348-355, 1998.
Sima et al., "Experimental obstructive coronary atherosclerosis in the hyperlipidemic hamster", J Submicrosc Cytol Pathol, vol. 22, No. 1, pp. 1-16, 1990.
Simionescu et al., "Prelesional modifications of the vessel wall in hyperlipidemic atherogenesis: Extracellular accumulation of modified and reassembled lipoproteins", Ann. NY Acad. Sci., vol. 598, pp. 1-16, 2001.
Smart et al., "Protein kinase C activators inhibit receptor-mediated potocytosis by preventing internalization of caveolae", Journal of Cell Biology, vol. 124, No. 3, pp. 307-313, 1994.
Solomin et al., "Computerized Tomography in Ovarian Cancer", Gynecologic Oncology, vol. 15 pp. 48-55, 1983.
Sudimack et al., "Targeted drug delivery via the folate receptor", Advanced Drug Delivery Reviews, vol. 41, pp. 147-162, 2000.
Sun et al., "Anhydrous Tetrabutylammonium Fluoride", J. Am. Chem. Soc., vol. 127, No. 7, pp. 2050-2051, 2005.
Sun et al., "Room-Temperature Nucleophilic Aromatic Fluorination: Experimental and Theoretical Studies", Angew. Chem. Int. Ed., No. 45, pp. 2720-2725, 2006.
Sundstrum et al., "Establishment and characterization of a human histiocytic lymphoma cell line (U-937)", International Journal of Cancer, vol. 17, No. 5, pp. 565-577, 1976.
Sutcliffe-Goulden, "Solid Phase Synthesis of [18F]Labelled Peptides for Positron Emission Tomography", Bio. & Medicin. Chem. Letters, No. 10, pp. 1501-1503, 2000.
Tan et al., "A Complete Remote-Control System for Reliable Preparation of [18F]altanserin", Applied Radiation and Isotopes, vol. 50, pp. 923-927, 1999.
Temple, Jr. et al., "Synthesis of Pseudo Cofactor Analogues as Potential Inhibitors of the Folate Enzymes", Journal of Medicinal Chemistry, vol. 25, pp. 161-166, 1982.
Toffoli et al., "Expression of Folate Binding Protein as a Prognostic Factor for Response to Platinum-Containing Chemotherapy and Survival in Human Ovarian Cancer", Int. J. Cancer, vol. 79, pp. 121-126, 1998.
Toffoli et al., "Overexpression of Folate Binding Protein in Ovarian Cancers", Int. J. Cancer (Pred. Oncol.), vol. 74., pp. 193-198, 1997.
Turk et al., "Folate-targeted imaging of activated macrophage in rats with adjuvant-induced arthritis", Arthritis and Rheumatism, vol. 46, No. 7, pp. 1947-1955, 2002.
Urban, "Screening for ovarian cancer: We now need a definitive randomized trial", BMJ, vol. 319, pp. 1317-1318, Nov. 1999.
Van Noort et al., "Cell Biology of Autoimmune Diseases", International Review of Cytology, vol. 178, pp. 127-204, 1998.
Vo-Dinh et al., "In Vivo Cancer Diagnosis of the Esophagus Using Differential Normalized Fluorescence (DNF) Indices", Lasers in Surgery and Medicine, vol. 16, pp. 41-47, 1995.
Wang et al., "Chemokines and their role in cardiovascular diseases", TCM, vol. 8, pp. 169-174, 1998.
Wang et al. "Synthesis, Purification, and Tumor Cell Uptake of Ga-Deferoxamine-Folate, a Potential Radiopharmaceutical for Tumor Imaging", American Chemical Society, Bioconjugate Chem., 1996, 7(1): 56-62, 1996.
Weinstock et al., "Folic Acid Analogs. II. p—{[2,6—Diamino—8—purinyl)methyl]amino}—benzoyl—L—glutamic Acid and Related Compounds", Journal of Medicinal Chemistry, 1970, 13(5): 995-997, 1970.
Weissleder et al., "In vivo imaging of tumors with protease-activated near-infrared fluorescent probes", Nature Biotechnology, vol. 17, pp. 375-378, Apr. 1999.
Weitman et al., "The folate receptor in central nervous system malignancies of childhood", Journal of Neuro-Oncology, vol. 21, pp. 107-112, 1994.
Westerhof et al., Carrier-and Receptor-Mediated Transport of Folate Antagonists Targeting Folate-Dependent Enzymes: Correlates of Molecular-Structure and Biological Activity, Molecular Pharmacology, 1995, 48: 459-471, 1995.
Whitehurst et al., "Development of an alternative light source to lasers for biomedical applications", SPIE, vol. 2629, pp. 291-298, 1993.
Wu et al., "Expression of Folate Receptor Type a in Relation to Cell Type Malignancy, and Differentiation in Ovary, Uterus and Cervix", Cancer Epidemiology, Biomarkers & Prevention, vol. 8, pp. 775-782, 1999.
Yavorsky et al., "Antiparticles", Handbook on Physics, pp. 339-340, 1984.
Zeisel et al., "Choline, an Essential Nutrient for Humans", The Faseb Journal, vol. 5, No. 7, pp. 2093-2098, 1991.
Delaloye et al., "Tumor imaging with monoclonal antibodies", Seminars in Nuclear Medicine, 25:144-164, 1995.
Reubi, "The role of peptides and their receptors as tumor markers", Endocrinology & Metabolism Clinics of North America, 22: 917-939, 1993.
Garin-Chesa et al., "Trophoblast and ovarian cancer antigen LK26. Sensitivity and specificity in immunopathology and molecular identification as a folate-binding protein", American Journal of Pathology, 142: 557-567, 1993.

(56) References Cited

OTHER PUBLICATIONS

Patrick et al., "Folate receptors as potential therapeutic targets in choroid plexus tumors of SV40 transgenic mice", Journal of Neuro-Oncology, 32: 111-123, 1997.

Weitman et al., "Distribution of the folate receptor GP38 in normal and malignant cell lines and tissues", Cancer Research, 52: 3396-3401, 1992.

Mathias et al., "Indium-111-DTPA-folate as a potential folate-receptor-targeted radiopharmaceutical", Journal of Nuclear Medicine, 39: 1579-1585, 1998.

Acosta et al., "Chromoendoscopy—where is it useful?", Journal of Clinical Gastroenterology, 27:13-20,1998.

Fleischer, "Chromoendoscopy and magnification endoscopy in the colon", Gastrointestinal Endoscopy, 49: S45-49, 1999.

Stepp et al., "Fluorescence endoscopy of gastrointestinal diseases: basic principles, techniques, and clinical experience", Endoscopy, 30: 379-386, 1998.

Ballou et al., "Tumor detection and visualization using cyanine fluorochrome-labeled antibodies", Biotechnology Progress, 13: 649-658, 1997.

Licha et al., "Synthesis, characterization, and biological properties of cyanine-labeled somatostatin analogues as receptor-targeted fluorescent probes", Bioconjugate Chemistry, 12: 44-50, 2001.

Becker et al., "Receptor-targeted optical imaging of tumors with near-infrared fluorescent ligands", Nature Biotechnology, 19: 327-331, 2001.

Terpetschnig et al., "Synthesis of squaraine-N-hydroxysuccinimide esters and their biological application as long-wavelength fluorescent labels", Analytical Biochemistry, 217: 197-204, 1994.

Mujumdar et al., "Cyanine dye labeling reagents containing isothiocyanate groups", Cytometry, 10: 11-19, 1989.

Wang et al., "Design and synthesis of [111 in]DTPA-folate for use as a tumor-targeted radiopharmaceutical", Bioconjugate Chemistry, 8: 673-679, 1997.

Dimartino et al., "Antiarthritic and immunoregulatory activity of spirogermanium", Journal of Pharmacology an Experimental Therapeutics, 236: 103-110, 1986.

Ross et al., "Differential regulation of folate receptor isoforms in normal and malignant tissues in vivo and in established cell lines. Physiologic and clinical implications", Cancer, 73: 2432-2443, 1994.

Ross et al., "Folate receptor type beta is a neutrophilic lineage marker and is differentially expressed in myeloid leukemia", Cancer, 85: 348-357, 1999.

Curtin et al., "Stage IV ovarian cancer: impact of surgical debulking", Gynecologic Oncology, 64: 9-12, 1997.

Munkarah et al., "Prognostic significance of residual disease in patients with stage IV epithelial ovarian cancer", Gynecologic Oncology, 64: 13-17, 1997.

Murolo et al., "Ultrasound examination in ovarian cancer patients. A comparison with second look laparotomy", Journal of Ultrasound in Medicine, 8: 441-443, 1989.

Piver et al., "Second-look laparoscopy prior to proposed second-look parotomy", Obstetrics and Gynecology, 55: 571, 1980.

Bell et al., "Intraoperative radioimmunodetection of ovarian cancer using monoclonal antibody B72.3 and a portable gamma-detecting probe", Obstetrics and Gynecology, 76: 607-677, 1990.

Reuter et al., "Detection of colorectal carcinomas by intraoperative RIS in addition to preoperative RIS: surgical and immunohistochemical findings", European Journal of Nuclear Medicine, 19: 102-109, 1992.

Hornung et al., "Minimally-invasive debulking of ovarian cancer in the rat pelvis by means of photodynamic therapy using the pegylated photosensitizer PEG-m-THPC", British Journal of Cancer, 81: 631-637, 1999.

Folli et al., "Immunophotodiagnosis of colon carcinomas in patients injected with fluoresceinated chimeric antibodies against carcinoembryonic antigen", Proceedings of the National Academy of Sciences of the United States of America, 89: 7973-7977, 1992.

Folli et al., "Antibody-indocyanin conjugates for immunophotodetection of human squamous cell carcinoma in nude mice", Cancer Research, 54: 2643-2649, 1994.

Bannwarth et al., "Methotrexate in rheumatoid arthritis. An update", Drugs, 47: 25-50, 1994.

Bettegowda, et al., Proc. Natl. Acad. ScL U.S.A., 102: 1145-1150, 2005.

Bunce, et al., Infect. Immun., 60: 2636-2640, 1992.

Claassen E. et al., "Preparation and characteristics of dichloromethylene diphosphonate-containing liposomes," *J. Microencapsul.*, 3: 109-14, 1986.

Marceau et al., Bioorganics and Medical Chemistry Letters, 15(24): 5442-5445, 2005.

Novabiochem® Letters, "Resins for the synthesis of biotinylated and fluorescently-labeled peptides," Jan. 2004, pp. 1-4, 2004.

Novabiochem® Letters, "Products for peptide ligation," Feb. 2004, pp. 1-4, 2004.

Novabiochem® Letters, "Amino acids for Fmoc SPPS," Mar. 2004, pp. 1-4, 2004.

Novabiochem® Letters, "PEG reagents," Apr. 2004, pp. 1-4, 2004.

Leamon et al., "Folate-Liposome-Mediated Antisense Oligodeoxynucleotide Targeting to Cancer Cells: Evaluation in Vitro and in Vivo", Bioconjugate Chem., 14, 738-747, 2003.

Leamon et al., "Folate-mediated Drug Delivery: Effect of Alternative conugate Chemistry", Journal of Drug Targeting, col. 7, No. 3, 157-169, 1999.

Marecos et al., "Antibody-Mediated versus Nontargeted Delivery in a Human Small Cell Lung Carcinoma Model", Bioconjugate Chemistry, 9:184-191 (1998).

"Osteomyelitis", XP-002569963, URL:http://emedicine.medscape.com/article/785020-overview>, retrieved Feb. 22, 2010.

Kennedy MD, "Folate-targeted imaging agents," Thesis submitted to the faculty of Purdue University in partial fulfillment of the requirements for the degree of Doctor of Philosophy, published Nov. 2004.

Holladay et al., "Riboflavin-mediated delivery of a macromolecule into cultured human cells," *Biochim Biophys Acta* 1426(1): 195-204 (1999).

Low PS, Leamon CP, Reddy JA, Green MA, Mathias C, Turk MJ, Waters DJ, Lu J, Lee RJ, Kennedy MD, "Folate-mediated delivery of therapeutic and imaging agents to cancer tissue," Gene, Drug Therapy, and Molecular Biology (Abstract), 2000.

Low, P.S., Leamon, C.P., Reddy, J.A., Green, M.A., Mathias, C., Turk, M.J., Waters, D.J., Lu, J., Lee, R.J. and Kennedy, M., "Folate-Mediated Delivery of Therapeutic and Imaging Agents to Cancer Tissues In Vivo," International Symposium on Tumor Targeted Delivery Systems, Bethesda, Maryland. British Journal of Pharmacology, vol. 134 (Abstract), 2001.

Kern, et al., "Evaluation of the Culprit Plaque and the Physiological Significance of Coronary Atherosclerotic Narrowings," Circulation, 2001; 103:3142-3149.

Phelps et al., Journal of Nuclear Medicine, 1975, 16(3): 210-224.

Snook et al., Br. J. Cancer, 1990, 62 (Suppl. X): 89-91.

Patton, Radiographics, 1998, 18: 995-1007.

Kanagaki et al., "Pituitary Gland and Parasellar Region," in *Magnetic Resonance Tomography*, Reiser et al. (eds.), 2008, p. 422.

Barnes, H. H., et al., "Purification of Catechol Siderophores by Boronate Affinity Chromatography: Identification of Chrysobactin From *Erwinia carotovora* subsp. *carotovora*", 1999, *BioMetals*, vol. 12, pp. 83-87.

Georgakoudi, Irene, et al., "In Vivo Flow Cytometry: A New Method for Enumerating Circulating Cancer Cells", Aug. 1, 2004, Cancer Research, No. 64, pp. 5044-5047.

Idanpaan-Heikkila, Ilona, et al., "Oligosaccharides Interfere With the Establishment and Progression of Experimental Pneumococcal Pneumonia", 1997, *The Journal of Infectious Diseases*, No. 176, pp. 704-712.

Iijima, Masatomi, et al., "IC202A, A New Siderophore with Immunosuppressive Activity Produced by *Streptoalloteichus* sp. 1454-19. I. Taxonomy, fermentation, isolation and biological activity.", Jan. 1999.

Lingwood, Clifford A., "Oligosaccharide Receptors for Bacteria: A View to a Kill", 1998, *Curr Opin Chem Biol.*, pp. 695-700.

(56) References Cited

OTHER PUBLICATIONS

Michelson, Alan D., et al., "Evaluation of Platelet Function by Flow Cytometry", 2000, *Methods*, vol. 21, pp. 259-270.
Novak, J., et al., "In Vivo Flow Cytometer for Real-Time Detection and Quantification of Circulating Cells", Jan. 1, 2004 *Optics Letters*, vol. 29, No. 1, pp. 77-79.
Ratledge, Colin, et al., "The Occurrence of Carboxymycobactin, The Siderophore of Pathogenic Mycobacteria, as a Second Extracellular Siderophore in *Mycobacterium smegmatis*", 1996 *Microbiology*, vol. 142, pp. 2207-2212.
Scharfman, Andree, et al., "*Pseudomonas aeruginosa* Binds to Neoglycoconjugates Bearing Mucin Carbohydrate Determinants and Predominantly to sialyl-Lewis x Conjugates", 1999, *Glycobiology*, vol. 9, No. 8, pp. 757-764.
Schalk, Isabelle J., et al., "Iron-Free Pyoverdin Binds to Its Outer Membrane Receptor FpvA in *Pseudomonas aeruginosa*: A New Mechanism for Membrane Iron Transport", 2001, *Molecular Microbiology*, vol. 39, No. 2, pp. 351-360.
Albrecht-Gary et al., "Bacterial Iron Transport: Coordination Properties of Pyoverdin PaA, a Peptidic Siderophore of *Pseudomonas aeruginosa*", 1994. *Inorg. Chem.*, 33 (26), pp. 6391-6402.
Henne, Walter A., et al., "Synthesis and Activity of a Folate Peptide Camptothecin Prodrug", (Aug. 9, 2006), *Bioorganic & Medicinal Chemistry Letters*, vol. 16, pp. 5350-5355.
Tang, Hailun, et al., "Prostate Targeting Ligands Based on N-Acetylated α-Linked Acidic Dipeptidase", (2003), *Biochemical and Biophysical Research Communications*, vol. 307, pp: 8-14.
Wosikowski, Katja, et al., "In Vitro and in Vivo Antitumor Activity of Methotrexate Conjugated to Human Serum Albumin in Human Cancer Cells", (May 2003), *Clinical Cancer Research*, vol. 9, pp. 1917-1926.
International Search Report and Written Opinion for PCT/US2007/023176 completed Aug. 4, 2008.
Wiener et al., "Targeting Dendrimer-Chelates to Tumors and Tumor Cells Expressing the High-Affinity Folate Receptor," *Investigative Radiology*, 1997; 32(12):748-754.
Paulos et al., "Ligand Binding and Kinetics of Folate Receptor Recycling in Vivo: Impact on Receptor-Mediated Drug Delivery," Molecular Pharmacology, 2004; 66:1406-1414.
He et al., "In vivo quantitation of rare circulating tumor cells by multiphoton intravital flow cytometry," Proc Nat Acad Sci USA, 2007; 104: 11760-11765.
Chen et al., "In vivo imaging of proteolytic activity in atherosclerosis," Circulation, 2002, 105: 2766-2771.
Mathias et al., "Synthesis of [99mTc]DTPA-Folate and Its Evaluation as a Folate-Receptor-Targeted Radiopharmaceutical", Bioconj. Chem., 2000; 11:253-257.
Linder et al., "In Virto & In Vivo Studies with α-and γ-lsomers of 99mTc-OXA-Folate Show Uptake of Both Isomers in Folate-Receptor (+) KB Cell Lines", Soc. Nucl. Med. Proc., May 2000; 41:5:119.
Ilgan et al., "99mTc-Ethylenedicysteine-Folate: A New Tumor Imaging Agent. Synthesis, labeling and Evaluation in Animals", Can. Biother. & Radiophar., 1998; 13:6:427-435.
Massoud et al., "Molecular imaging in living subjects: seeing fundamental biological processes in a new light", 2003, Genes Dev. 17: 545-580.
Caliceti et al., "Pharmacokinetic and biodistribution properties of poly9ethylene glycol)—protein conjugates", 2003, Adv. Drug Del. Rev. 55: 1261-1277.
Tamaki, et al., "PET in Oncology" Jpn J Cancer Clin, 2003, 49(6): 531-535.
Bendele et al., "Animal Models of Arthritis: Relevance to Human Disease", Toxicology Pathology, vol. 27, No. 1, pp. 134-142, 1999.
Tanaka, et al., "Digestive tract lesions and immunity," The Japanese Journal of Gastroenterology, 1994, vol. 91(2): 131-135.
Folate-FITC (http://www.medkoo.com/Anticancer-trials/EC-17.htm (downloaded on Aug. 8, 2013)).
Atherosclerosis (http://web.archive.oro/web/20081207060136/http://en.wikipedia.oro/wiki/Atherosclerosis (archived on Dec. 7, 2008)).

Yang et al, Imaging Tumor Folate Receptors using radiolabeled folate and methotrexate, Jour Labelled Compounds and Radiopharmaceuticals, 1999, Sussex, GB, vol. Suppl 1, 42: S696-S697.
Ilgan et al., "Imaging tumor folate receptors using 111 IN-DTPA-methotrexate." *Cancer Biother. Radiopharm.*, 1998, 13(3) pp. 177-184.
Akihiro H. et al., "Affinity for a-tocopherol transfer protein as a determinant of the biological activities of vitamin E analogs." *Federation of European Biochemical Societies*, 1997, vol. 409, pp. 105-108.
Kazuki S. et al., "Novel vitamin D3 antipsoriatic antedrugs: 16—En—22—oxa—1a,25—(OH)2D3 analogs," *Bioorganic & Medicinal Chemistry*, 2006, vol. 14, pp. 1838-1850.
Hisashi T. et al., "c-Fos protein as a target of anti-osteoclastogenic action of vitamin D, and synthesis of new analogs," journal article, *The Journal of Clinical Investigation*, 2006, vol. 116, No. 2, Feb., pp. 528-535.
Masato S. et al., "Synthesis and biological activities of new 1a,25-dihydroxy-19-norvitamin D3 analogs with modifications in both the A-ring and the side chain," journal article, *Bioorganic & Medicinal Chemistry*, 2006, 14(12) pp. 4277-4294.
Agoston E.S. et al., "Vitamin D Analogs as Anti-Carcinogenic Agents" *Anti-Cancer Agents in Medicinal Chemistry* 2006, 6(1), pp. 53-71.
Lonsdale, D., "A Review of the Biochemistry, Metabolism and Clinical Benefits of Thiamin(e) and Its Derivatives." *Evidence-Based Complementary & Alternative Medicine: eCAM*. Advance Access Publication, vol. 3, Feb. 2006, pp. 49-59.
Nosaka, K. et al., "Separate Determination of Anticoccidial Thiamine Analogs by High-Performance Liquid Chromatography." *ActaA Vitaminol. Et Enzymol.*, 1984, vol. 6 92), pp. 137-142.
Kandiko, C.T. et al., "Inhibition of Rat Brain Pyruvate Dehydrogenase by Thiamine Analogs." *Biochem. Pharmacology*, vol. 37, No. 22, (1988) pp. 4375-4380.
Spry, C. et al., "A Class of Pantothenic Acid Analogs Inhibits Plasmodium Falciparum Pantothenate Kinase and Represses the Proliferation of Malaria Parasites." *Antimicrobial Agents and Chemotherapy*, Nov. 2005, pp. 4649-4657.
Sargent, D.R. et al., "Antimetabolites of Pantothenic Acid, Ureido- and Carbamoyl-Derivatives." *Texas Reports on Biology and Medicine*, 1975, vol.. 33, No. 3, pp. 433-443.
Hanck, A.B. et al., "Dexpanthenol (Ro 01-4709) in the treatment of constipation." Abstract, Acta Vitaminol Enzymol, 1982, vol. 4 (1-2), pp. 87-97.
Kagechika, H. et al., "Synthetic Retinoids: Recent Developments Concerning Structure and Clinical Utility." *J. Med. Chem.*, Sep. 22, 2005, vol. 48, No. 19, pp. 5875-5883.
Shealy, Y.F. "Synthesis and Evaluation of Some New Retinoids for Cancer Chemoprevention." *Preventive Medicine*, 1989, vol. 18, pp. 624-645.
Landuer, W. et al., "The Interaction in Teratogenic Activity of the Two Niacin Analogs 3-acetylpyridine and 6- aminonicotinamide," *J Experimental Zoology*, 1962, vol. 151, pp. 253-258.
Renz, P. et al., "Synthesis of 4-Aza-5, 6-diethylbenzimidazole and Biosynthetic Preparation of 4- and 7-Aza-5, 6-dimethylbenzimidazolylcobamide," *Z. Naturforsch*, 1997, vol. 52C, pp. 5287-5291.
Ayers, W.A., "Effect of Vitamin B12 and Analogs on the Respiration of a Marine Bacterium." *Archives of Biochemistry and Biophysics*, 1962, vol. 96, pp. 210-215.
Toraya, T. et al., "Immobilized Derivatives of Vitamin B12 Coenzyme and Its Analogs." *Methods in Enzymology*, 1980, vol. 67, pp. 57-66.
Ueda, M. et al., "Effect of Vitamin B12 Derivatives on Urinary Excretion of Methylmalonic Acid in Liver Diseases." *Acta Med. Okayama*, 1970, vol. 24, pp. 365-372.
Toraya, T. et al., "The Synthesis of Several Immobilized Derivatives of Vitamin B12 Coenzyme and Their Use as Affinity Adsorbents for a Study of Interactions of Diol Dehydrase with the Coenzyme." *Journal of Biological Chemistry*, 1980, vol. 255, No. 8, Apr. 25, pp. 3520-3525.

(56) References Cited

OTHER PUBLICATIONS

Takahata, Y. et al., "Synthesis, Properties and Microbiological Activity of Hydrophobic Derivatives of Vitamin B12." *J. Nutr. Sci. Vitaminol.*, 1995, vol. 14, pp. 515-526.

Kamao, M. et al., "Determination of Plasma Vitamin K by High Performance Liquid Chromatography with Fluorescence Detection Using Vitamin K Analogs as Internal Standards." *J. of Chromatography B.*, 2005, vol. 816, pp. 41-48.

Nishikawa, Y. et al., "Growth Inhibition of Hepatoma Cells Induced by Vitamin K and Its Analogs." *Journal of Biological Chemistry*, 1995, vol. 270, No. 47, Nov. 24, pp. 28304-28310.

Mack, D.O. et al., "The Carboxylation Activity of Vitamin K Analogs with Substitutions at Position 2, 3, or 5." *Journal of Biological Chemistry*, 1979, vol. 254, Apr. 25, pp. 2656-2664.

Mock, D.M. et al., "Urinary Biotin Analogs Increase in Humans During Chronic Supplementation: the Analogs are Biotin Metabolites." *The American Physiological Society*, 1997, pp. 83-85.

International Search Report for PCT/US2002/13890 completed Oct. 28, 2002.

Vesely, D.L. et al., "Biotin Analogs Activate Guanylate Cyclase." *Molecular and Cellular Biochemistry*, 1984, vol. 60, pp. 109-114.

Lambooy, J.P., "Riboflavin Analogs Utilized for Metabolism by a Lactobacillus Casei Mutant." *Int. J. Biochem.*, 1984, vol. 16, No. 2, pp. 231-234.

Nielsen, P. et al., "Phosphates of Riboflavin and Riboflavin Analogs: A Reinvestigation by High- Performance Liquid Chromatography." *Analytical Biochemistry*, 1983, vol. 130, pp. 359-368.

Arya, P. et al., "Design and Synthesis of Analogs of Vitamin E: Antiproliferative Activity Against Human Breast Adenocarcinoma Cells." *Bioorganic & Medicinal Chemistry Letters*, 1998, vol. 8, No. 18, pp. 2433-2438.

Trachewsky, D. "Antihypertensive Effect of Riboflavin Analogs in Rats with Mineralocorticoid-Induced Hypertension." *Hypertension*, 1981, vol. 3, No. 1, Jan-Feb., pp. 75-80.

Skinner, W.A. et al., "Structure-Activity Relations in the Vitamin E Series. II. Derivatives of alpha- Tocopherol Substituted at the 5-Methyl Group." *J Med. Chem.*, 1962, vol. 12, pp. 64-66.

Neuzil, J. et al., "Vitamin E. Analogs: A New Class of Multiple Action Agents with Anti-Neoplastic and Anti-Atherogenic Activity." *Apoptosis*, 2002, vol. 7, pp. 179-187.

Politis, I. et al., "The Effect of Various Vitamin E Derivatives on the Urokinase-Plasmogen Activator System of Ovine Macrophages and Neutrophils." British Journal of Nutrition, 2003, vol. 89, pp. 259-265.

Wang, X. et al., "Vitamin E Analogs Trigger Apoptosis in HER2/erbB2-Overexpressing Breast Cancer Cells by Signaling Via the Mitochondrial Pathway." *Biochemical and Biophysical Research Communication*, 2005, vol. 326, pp. 282-289.

Kilbourn et al, Fluorine-18 labeling of proteins, 1987, J Nucl Med, 28: 462-470.

Coussens et al, Inflammation and cancer, 2002, Nature, 420: 860-867.

PCT International Search Report and Written Opinion for PCT Application No. PCT/US2010/026406, mailed Apr. 15, 2010.

Jallad et al, Dissertation Abstracts International, 2001, 65(5B), p2390.

Stummer et al, J Neurosurg, 2000, 93:1003-1013.

Kennedy et al, Dissertation Abstracts International, 2001, 65(5B), p. 2354.

Nisshoshi, 1994, The Japanese Journal of Gastoenterology, 91(2): 131-135.

Extended European Search Report for EP 02734139, completed Jun. 11, 2004.

International PCT Search Report and Written Opinion for PCT Application No. PCT/US2008/053293, completed Mar. 10, 2009.

International PCT Search Report and Written Opinion for PCT Application No. PCT/US2005/046708, completed Sep. 20, 2006.

Extended European Search Report for EP 05855293, completed Jun. 12, 2009.

Extended European Search Report for EP 04753487, completed Jun. 16, 2006.

International PCT Search Report and Written Opinion for PCT Application No. PCT/US2004/016667, completed Sep. 22, 2004.

International PCT Search Report and Written Opinion for PCT Application No. PCT/US2008/064711, completed May 19, 2010.

International PCT Search Report and Written Opinion for PCT Application No. PCT/US2006/037112, completed Nov. 14, 2007.

Reddy J A et al: "Expression and functional characterization of the beta-isoform of the folate receptor on CD34(+) cells," Blood, vol. 93, No. 11, Jun. 1, 1999, pp. 3940-3948, XP002300805.

Japanese Translation of PCT International Application No. 2005-519078.

Japanese Translation of PCT International Application No. 2004-530678.

Extended European Search Report for EP 07867348, completed Jul. 29, 2010.

\* cited by examiner

| METHOD | RECOVERY (%) |
|---|---|
| 1 FICOLL DENSITY SEPARATION +Ab COCKTAIL | 61.3 |
| 2 FICOLL + A23187 | 33.9 |
| 3 FICOLL DENSITY SEPARATION | 45.1 |
| 4 AMMONIUM CHLORIDE LYSIS | 5.0 |
| 5 ONCOQUICK | 20.0 |
| 6 HISTOPAQUE 1077 | 24.3 |
| 7 HISTOPAQUE 1083 | 27.5 |
| 8 HISTOPAQUE 1119 | 17.2 |
| 9 SPINDISK TUBE + FICOLL | 30.0 |

(i)　　　　　　　(ii)　　　　　　　(iii)

(i)　　　　　　　(ii)　　　　　　　(iii)

(i)            (ii)            (iii)

EX VIVO FLOW CYTOMETRY METHOD AND DEVICE

CROSS REFERENCE TO RELATED APPLICATIONS

This application is a divisional application of U.S. Non-provisional patent application Ser. No. 12/513,028, filed on Nov. 2, 2009, now issued U.S. Pat. No. 8,685,752, which is a U.S. National Stage Application of International Application Serial Number PCT/US2007/023176, filed on Nov. 2, 2007, which claims priority to U.S. Provisional Patent Application Ser. No. 60/856,667, filed on Nov. 3, 2006, and U.S. Provisional Patent Application Ser. No. 60/956,562, filed Aug. 17, 2007, the entire disclosures of which are hereby incorporated by reference.

FIELD OF THE INVENTION

This invention relates to an optical method for detecting and/or quantitating in an ex vivo sample of a patient body fluid a pathogenic cell population present in a body fluid, and devices therefor. More particularly, the invention relates to the use of ligand-imaging agent conjugates that bind to the pathogenic cells in an optical method for detecting and/or quantitating the cells, and devices for use in this method.

BACKGROUND AND SUMMARY

The presence of pathogenic cells in body fluids, such as the bloodstream, or the spread of pathogenic cells from other sites to the bloodstream is one of the important factors that determines whether or not a diseased patient will survive. For example, the spread of malignant cells from the primary neoplasm to distant organs is an important factor in determining whether cancer patients will survive. Highly sensitive methods must be developed that can detect and/or quantify circulating pathogenic cells, such as metastatic cells, and other types of pathogenic cells in the vasculature at the earliest stages of disease. Achievement of this objective requires highly sensitive, biocompatible probes with selectivity for the pathogenic cells.

Currently, CT, MRI, tissue/sentinel lymph node biopsy, and serum cancer marker analysis can detect some level of residual disease in cancer patients; however, the presence of tumor cells in circulation (CTCs) correlates most sensitively with cancer prognosis and metastasis. Additionally, flow cytometry is a method that is used for detecting and quantitating target cell populations using fluorescent probes that render high specificity and low background measurements. Flow cytometry assays can be performed in vivo without acquisition of a patient sample or ex vivo using a sample of a patient body fluid acquired from the patient. However, prior, conventional ex vivo techniques have many deficiencies. For example, the methods typically require the use of a large sample due to low sensitivity of the methods.

More recently, a conceptual in vivo flow cytometry technique utilizing confocal microscopy has been described for the real-time detection of flowing tumor cells in vivo (Georgakoudi, et al. (2004) *Cancer Res.*, 64, 5044-5047; Novak, et al. (2004) *Optics Lett.*, 29, 77-79). However, there is no available method with the requisite sensitivity and biocompatibility for performing the detection and quantification of pathogenic cells in an ex vivo sample of a patient body fluid. In this application, Applicants describe the detection and quantification of pathogenic cells found in patient body fluids using an ex vivo sample of a patient body fluid and using flow cytometry-based techniques.

In one embodiment, a method is described for diagnosing a disease state mediated by pathogenic cells. The method comprises the steps of combining with an ex vivo patient sample a composition comprising a conjugate or complex of the general formula $A_b$-X, wherein the group $A_b$ comprises a ligand that binds to the pathogenic cells and the group X comprises an imaging agent, and detecting the pathogenic cells that express a receptor for the ligand using flow cytometry.

In another embodiment, a method is described for determining a prognosis of a cancer by detecting cancer cells in an ex vivo patient sample. The method comprises the steps of detecting the cancer cells in the ex vivo patient sample by flow cytometry, and determining a prognosis for the cancer.

In another embodiment, a method is described for quantitating pathogenic cells. The method comprises the steps of combining with an ex vivo patient sample a composition comprising a conjugate or complex of the general formula $A_b$-X, wherein the group $A_b$ comprises a ligand that binds to the pathogenic cells and the group X comprises an imaging agent, and quantitating the pathogenic cells in the ex vivo patient sample using flow cytometry.

BRIEF DESCRIPTION OF THE DRAWINGS

FIG. 9 shows flourophore-dependent studies using FACS (2 Atom Spacer).

FIG. 10 shows flourophore-dependent studies using FACS (24 Atom Spacer).

FIG. 11 shows ALEXAFLUOR 647-dependent studies using FACS (24 Atom Spacer).

FIG. 12 shows OREGON GREEN 488-dependent studies using FACS (27 Atom Spacer).

FIG. 13 shows BODIPY 505-dependent studies using FACS (24 Atom Spacer).

FIG. 14 shows OREGON GREEN 488-dependent studies using FACS (24 Atom Spacer).

FIG. 15 shows fluorescence labeling studies using confocal microscopy.

FIG. 16 shows blood spiking studies using FACS.

FIG. 18 shows detection of CTCs in prostate cancer patient samples.

DETAILED DESCRIPTION

Figures 1, 2:
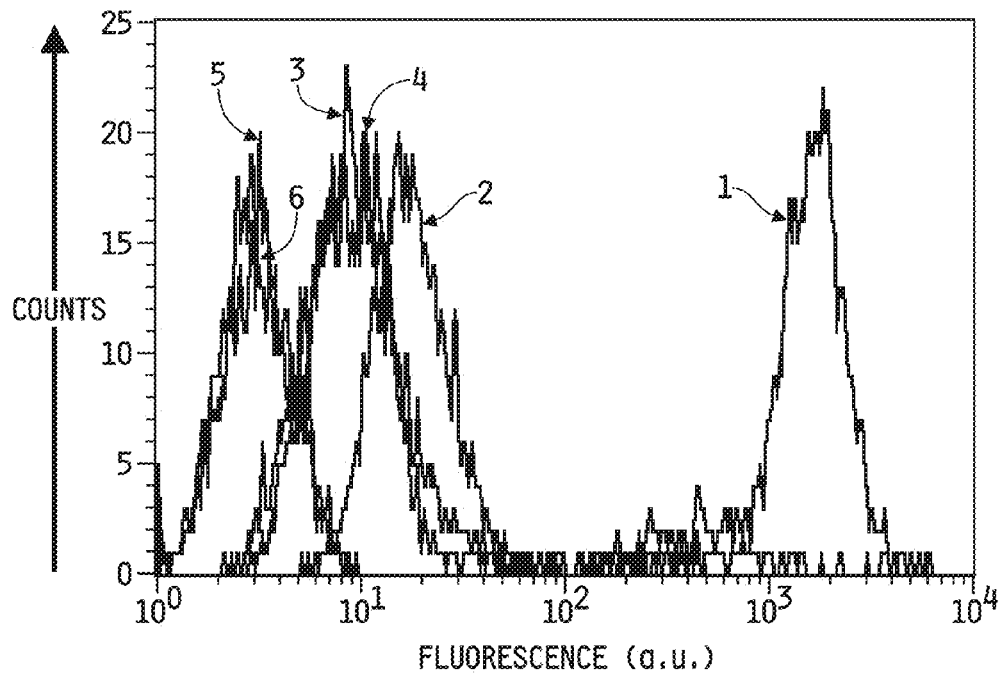
FIG. 1 shows labeling of folate receptor-positive tumor cells with folate conjugates compared to anti-folate receptor polyclonal antibodies.
FIG. 2 shows a comparison of the methods for separating a tumor cell enriched fraction from a red cell enriched fraction of whole blood prior to tumor cell labeling with folate-ALEXAFLUOR 488.

Methods are provided for diagnosing disease states mediated (e.g., caused or augmented) by pathogenic cells. In one embodiment, the pathogenic cells can be cancer cells. In another embodiment, the pathogenic cells can be metastatic cancer cells. In one aspect, the disease states can be diagnosed by combining with an ex vivo sample of a patient body fluid a composition comprising a conjugate or complex of the general formula $A_b$-X where the group $A_b$ comprises a ligand that binds to the pathogenic cells and the group X comprises an imaging agent. In another illustrative embodiment, the method further comprises the step of quantitating and/or detecting the presence of the pathogenic cells. In yet another embodiment, multiphoton flow cytometry can be used to detect and/or to quantitate the pathogenic cells. As used herein, "mediated by" in reference to diseases mediated by pathogenic cells means caused by or augmented by.

In one embodiment, the imaging agent (e.g., a reporter molecule) can comprise a chromophore such as, for example, fluorescein, rhodamine, TEXAS RED, phycoerythrin, OREGON GREEN, ALEXAFLUOR 488 (Molecular Probes, Eugene, Oreg.), Cy3, Cy5, Cy7, and the like.

In another aspect, the imaging agent is a fluorescent agent selected from OREGON GREEN fluorescent agents, including but not limited to OREGON GREEN 488, OREGON GREEN 514, and the like, ALEXAFLUOR fluorescent agents, including but not limited to ALEXAFLUOR 488, ALEXAFLUOR 647, and the like, fluorescein, and related analogs, rhodamine fluorescent agents, including but not limited to tetramethylrhodamine, and the like, DYLIGHT fluorescent agents, including but not limited to DYLIGHT 680, and the like, CW 800, TEXAS RED, phycoerythrin, and others. Illustrative fluorescent agents are shown in the following illustrative general structures:

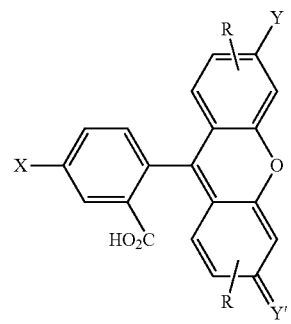

where X is oxygen, nitrogen, or sulfur, and where X is attached to linker L; Y is $OR^a$, $NR^a_2$, or $NR_3^{a+}$; and Y' is O, $NR^a$, or $NR_2^{a+}$; where each R is independently selected in each instance from H, fluoro, sulfonic acid, sulfonate, and salts thereof, and the like; and $R^a$ is hydrogen or alkyl, and, in another embodiment,

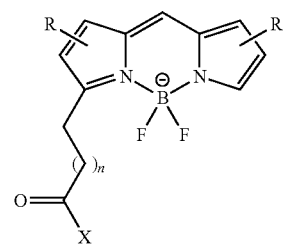

where X is oxygen, nitrogen, or sulfur, and where X is attached to linker L; and each R is independently selected in each instance from H, alkyl, heteroalkyl, and the like; and n is an integer from 0 to about 4.

Diagnosis typically occurs before treatment. However, in the diagnostic methods described herein, the term "diagnosis" can also mean monitoring of the disease state before, during, or after treatment to determine the progression of the disease state. The monitoring can occur before, during, or after treatment, or combinations thereof, to determine the efficacy of therapy, or to predict future episodes of disease.

The method disclosed herein can be used for both human clinical medicine and veterinary applications. Thus, the patient afflicted with the disease state and in need of diagnosis can be a human, or in the case of veterinary applications, can be a laboratory, agricultural, domestic or wild animal.

In various illustrative embodiments, body fluids that can be used to detect and/or quantify circulating pathogenic cells, include, but are not limited to urine, nasal secretions, nasal washes, bronchial lavages, bronchial washes, spinal fluid, sputum, gastric secretions, reproductive tract secretions (e.g. seminal fluid), lymph fluid, mucus, and blood. These samples can be prepared for testing as described herein.

In various embodiments the pathogenic cells can be quantitated using methods described herein. In various aspects, the pathogenic cells can be quantitated in 100 ul, 200 ul, 300 ul, 400 ul, 500 ul, 1 ml, 2 ml, 3 ml, 4 ml, 5 ml, 6 ml, or 8 ml of a patient body fluid. In various illustrative embodiments, the pathogenic cells can be quantitated in any of these volumes at values including about 1 to 10, 1 to 15, 1 to 20, 1 to 50, 1 to 100, 1 to 200, or 1 to 500 pathogenic cells per patient sample, or about 0 to 10, 0 to 15, 0 to 20, 0 to 50, 0 to 100, 0 to 200, or 0 to 500 pathogenic cells per patient sample.

In the ligand conjugates of the general formula Ab-X, the group Ab is a ligand that binds to the pathogenic cells when the conjugates are used to diagnose disease states. The pathogenic cells may be circulating pathogenic cells, such as metastatic cancer cells, and other types of cancer cells that can be found in the body fluid of a patient at various stages of disease. Any of a wide number of ligands can be employed.

In one embodiment, the ligand conjugates can be used to detect pathogenic cells and the ligand can be folic acid, a folic acid analog, or another folate receptor-binding molecule. Analogs of folate that can be used include folinic acid, pteropolyglutamic acid, and folate receptor-binding pteridines such as tetrahydropterins, dihydrofolates, tetrahydrofolates, and their deaza and dideaza analogs. The terms "deaza" and "dideaza" analogs refers to the art recognized analogs having a carbon atom substituted for one or two nitrogen atoms in the naturally occurring folic acid structure. For example, the deaza analogs include the 1-deaza, 3-deaza, 5-deaza, 8-deaza, and 10-deaza analogs. The dideaza analogs include, for example, 1,5 dideaza, 5,10-dideaza, 8,10-dideaza, and 5,8-dideaza analogs. The foregoing folic acid analogs are conventionally termed "folates," reflecting their capacity to bind to folate receptors. Other folate receptor-binding analogs include aminopterin, amethopterin (methotrexate), N10-methylfolate, 2-deamino-hydroxyfolate, deaza analogs such as 1-deazamethopterin or 3-deazamethopterin, and 3',5'-dichloro-4-amino-4-deoxy-N10-methylpteroyl-glutamic acid (dichloromethotrexate).

In one embodiment, the ligand conjugates can be used to detect cancer cells and the ligand can be a prostate-specific membrane antigen (PSMA)-targeted ligand, or another prostate cancer specific binding molecule. In other illustrative embodiments, inhibitors of N-acetylated α-linked acidic dipeptidase (NAALADASE) activity of PSMA can be used to target and detect prostate cancer cells as described in Tang et al., "Prostate targeting ligands based on N-acetylated α-linked acidic dipeptidase," Biochemical and Biophysical Research Communications, 307: 8-14 (2003), which is incorporated herein by reference.

For example, the ligand can be a ligand of PSMA attached through a linker to an imaging agent where the linker comprises a linear chain of at least seven atoms, at least 14 atoms, at least 7 atoms to about 20 atoms, or about 14 atoms to about 24 atoms. In one embodiment, the ligand is a compound selected from the group consisting of

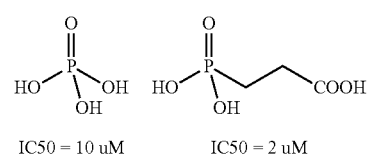

IC50 = 10 uM        IC50 = 2 uM

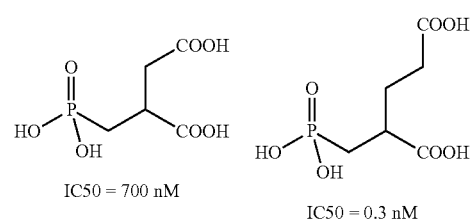

IC50 = 700 nM       IC50 = 0.3 nM

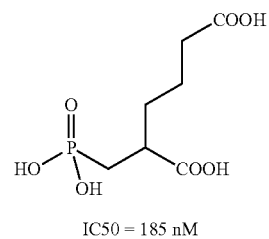

IC50 = 185 nM

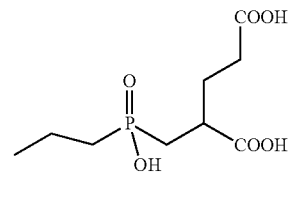

IC50 = 560 nM

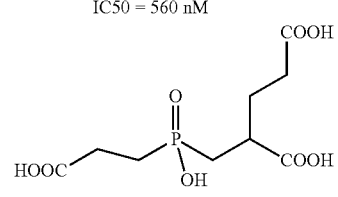

IC50 = 1 nM

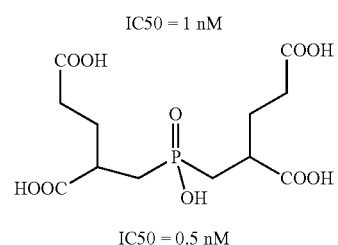

IC50 = 0.5 nM

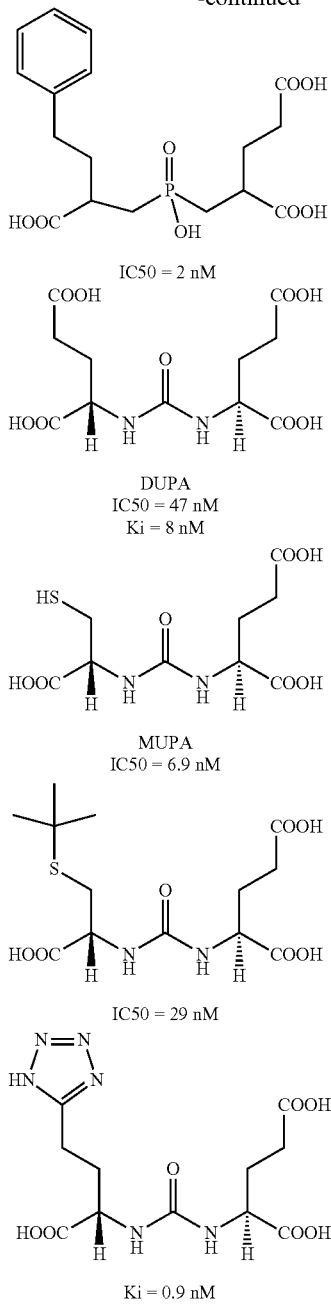

In another embodiment, the ligand can be a compound of the formula

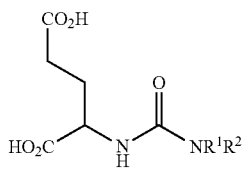

wherein $R^1$ and $R^2$ are each selected from hydrogen, optionally substituted carboxylic acids, such as thiolacetic acids, thiolpropionic acids, and the like; malonic acids, succinic acids, glutamic acids, adipic acids, and the like, and others.

Other PSMA ligands are described in provisional patent application No. 60/956,489 titled "PSMA Binding Ligand-Linker Conjugates and Methods for Using," incorporated herein by reference in its entirety.

In another embodiment, other vitamins can be used as the ligand for the use of the conjugates in detecting pathogenic cells. The vitamins that can be used in accordance with the methods described herein include niacin, pantothenic acid, folic acid, riboflavin, thiamine, biotin, vitamin $B_{12}$, vitamins A, D, E and K, other related vitamin molecules, analogs and derivatives thereof, and combinations thereof. In other embodiments, the ligand can be any ligand that binds to a receptor expressed or overexpressed on cancer cells.

In various illustrative embodiments, the ligand may be capable of specifically binding to a population of pathogenic cells in the patient due to preferential expression of a receptor for the ligand, accessible for ligand binding, on the pathogenic cells. Acceptable ligands include peptide ligands identified from library screens, tumor-specific peptides, tumor-specific aptamers, tumor-specific carbohydrates, small organic molecules derived from combinatorial libraries, growth factors, such as EGF, FGF, insulin, and insulin-like growth factors, and homologous polypeptides, somatostatin and its analogs, and other molecules that bind specifically to a receptor preferentially expressed on the surface of cancer cells, or fragments of any of these molecules.

For conjugates used to detect pathogenic cells wherein the group Ab is folic acid, a folic acid analog, or another folic acid receptor binding ligand, these conjugates are described in detail in U.S. Pat. No. 5,688,488, the specification of which is incorporated herein by reference. That patent, as well as related U.S. Pat. Nos. 5,416,016 and 5,108,921, each incorporated herein by reference, describe methods and examples for preparing conjugates useful in accordance with the methods described herein. The present ligand-imaging agent conjugates can be prepared and used following general protocols described in those earlier patents, and by the protocols described herein.

The conjugates for use in the method described herein can be conjugated by using any art-recognized method for forming a complex. This can include covalent, ionic, or hydrogen bonding of the ligand to the imaging agent, either directly or indirectly via a linking group such as a divalent linker. The conjugate is typically formed by covalent bonding of the ligand to the imaging agent through the formation of amide, ester or imino bonds between acid, aldehyde, hydroxy, amino, or hydrazo groups on the respective components of the complex or, for example, by the formation of disulfide bonds.

In one embodiment of the invention where pathogenic cells are detected, the ligand is folic acid, an analog of folic acid, or any other folate receptor binding molecule, and the folate ligand is conjugated to the imaging agent by a procedure that utilizes trifluoroacetic anhydride to prepare γ-esters of folic acid via a pteroyl azide intermediate. This procedure results in the synthesis of a folate ligand, conjugated to the imaging agent only through the γ-carboxy group of the glutamic acid groups of folate. Alternatively, folic acid analogs can be coupled through the α-carboxy moiety of the glutamic acid group or both the α and γ carboxylic acid entities.

Illustratively, a variety of folate analogs and derivatives may be substituted for folate itself in forming the folate linker conjugates. Those analogs and derivatives, or protected forms thereof, may be included in the synthetic protocols described herein. For example, folate analogs and derivatives are well-known in the art, such as those described in Westerhof, et al., Mol. Pharm. 48: 459-471 (1995), incorporated herein by reference.

In addition, structural modifications of the linker portion of the conjugates is contemplated herein. For example, a number of amino acid substitutions may be made to the linker portion of the conjugate, including but not limited to naturally occurring amino acids, as well as those available from conventional synthetic methods. In one aspect, beta, gamma, and longer chain amino acids may be used in place of one or more alpha amino acids. In another aspect, the stereochemistry of the chiral centers found in such molecules may be selected to form various mixture of optical purity of the entire molecule, or only of a subset of the chiral centers present. In another aspect, the length of the peptide chain included in the linker may be shortened or lengthened, either by changing the number of amino acids included therein, or by including more or fewer beta, gamma, or longer chain amino acids. In another aspect, the selection of amino acid side chains in the peptide portion may be made to increase or decrease the relative hydrophilicity of the linker portion specifically, or of the overall molecule generally.

Similarly, the length and shape of other chemical fragments of the linkers described herein may be modified. In one aspect, the linker includes an alkylene chain. The alkylene chain may vary in length, or may include branched groups, or may include a cyclic portion, which may be in line or spiro relative to the alkylene chain. In another aspect, where the linker includes a beta thiol releasable fragment, it is appreciated that other intervening groups connecting the thiol end to the hydroxy or carbonate end may be used in place of the ethylene bridge, such as but not limited to optionally substituted benzyl groups, where the hydroxy end is connected at the benzyl carbon and the thiol end is connected through the ortho or para phenyl position, and vice versa.

The conjugates used in accordance with the methods described herein of the formula Ab-X are used in one aspect to formulate diagnostic compositions, for combining with a patient sample, wherein the compositions comprise effective amounts of the conjugate and an acceptable carrier therefor. In various embodiments, the amount of the conjugate effective for use in accordance with the methods described herein can be about 1 nM to 100 nM, 1 nM to 200 nM, 1 nM to 500 nM, 1 nM to 10 uM, 1 nM to 1 mM, 10 nM to 200 nM, 10 nM to 500 nM, 100 nM to 500 nM, 10 nM to 10 uM, or 100 nM to 1 mM. In various illustrative embodiments, the conjugate is combined with 100 ul, 200 ul, 300 ul, 400 ul, 500 ul, 1 ml, 2 ml, 3 ml, 4 ml, 5 ml, 6 ml, or 8 ml of a patient body fluid.

Figure 8:
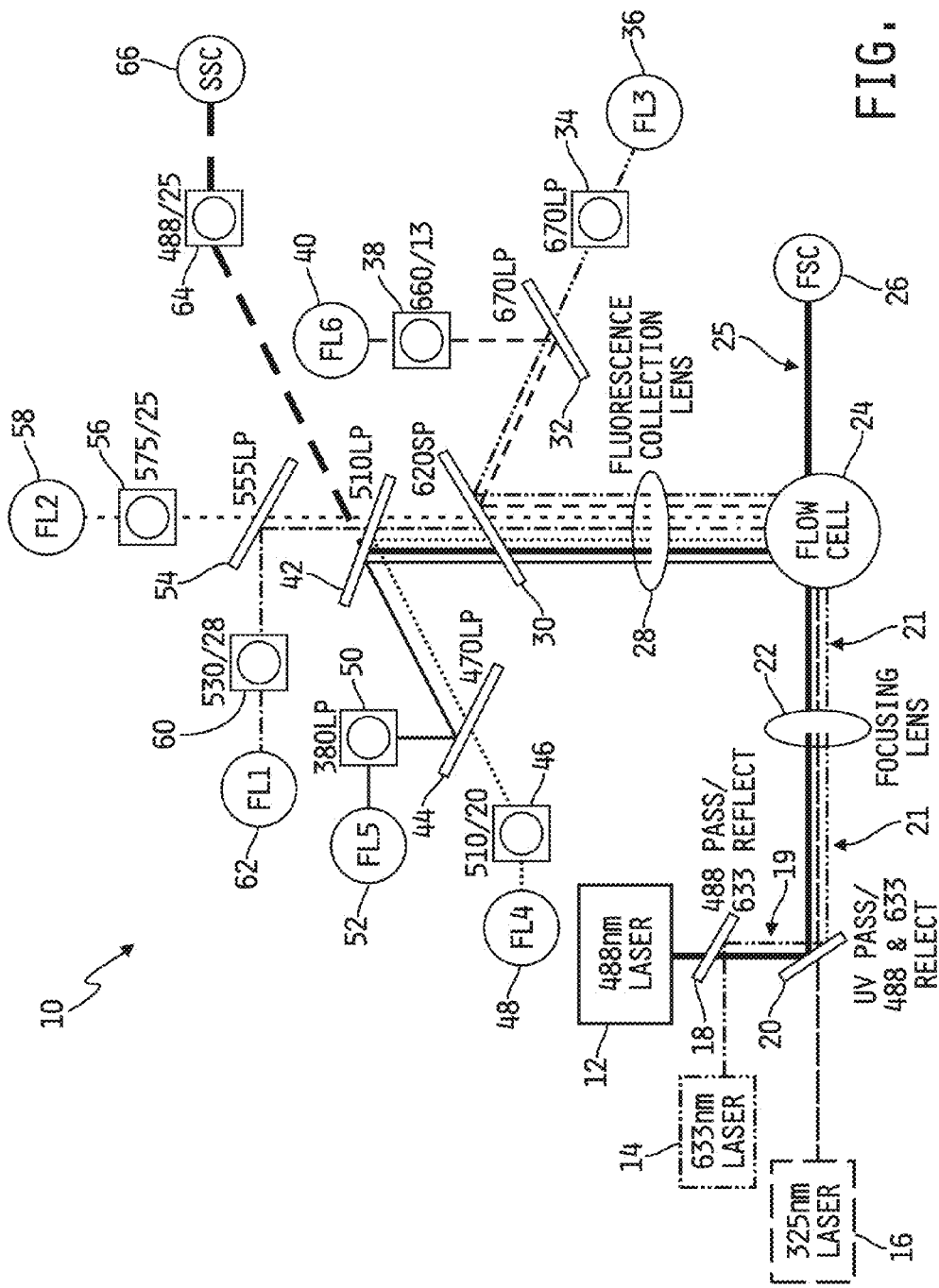
FIG. 8 shows an apparatus for conducting the method described herein.

Referring now to FIG. 8, in one embodiment, a flow cytometer system 10 for performing the ex vivo multi-photon flow cytometry process described herein includes a first laser 12, a second laser 14, and a third laser 16. Each of the lasers 12, 14, 16 is configured to generate a laser light beam having a predetermined wavelength. For example, in the embodiment illustrated in FIG. 8, the first laser 12 is configured to generate a laser light beam having a wavelength of about 488 nanometers, the second laser 14 is configured to generate a laser light beam having a wavelength of about 633 nanometers, and the third laser 16 is configured to generate a laser light beam having a wavelength of about 325 nanometers.

The output laser light beam of the first laser 12 is directed through a first dichroic mirror 18. The first dichroic mirror 18 is configured to transmit a predetermined first wavelength or range of wavelengths of light while reflecting a second wavelength or range of wavelengths of light. In the illustrative embodiment, the first dichroic mirror 18 is configured to transmit light having a wavelength of about 488 nanometers while reflecting wavelengths of about 633 nanometers. As such, the first dichroic mirror 18 is positioned such that the output laser light beam of the first laser 12 is transmitted through the first dichroic mirror 18 while the output laser light beam of the second laser 14 is reflected by the first dichroic mirror 18. As such, the resulting laser light beam 19 includes wavelengths of the output laser light beam of the first laser 12 and wavelengths of the output laser light beam of the second laser 14.

The light beam 19 is directed to and subsequently reflected by a second dichroic mirror 20. Similar to the first dichroic mirror 18, the second dichroic mirror 20 is configured to transmit a predetermined first wavelength or range of wavelengths of light while reflecting a second wavelength or range of wavelengths of light. In the illustrative embodiment of FIG. 8, the second dichroic mirror 20 is configured to reflect the wavelengths of the light beam 27 (i.e., the wavelengths of the output laser light beams of the first laser 12 and the second laser 14) and transmit the wavelengths of the output laser light beam of the third laser 16. That is, in the embodiment illustrated in FIG. 8, the second dichroic mirror 20 is configured to reflect light having wavelengths of about 488 nanometers and about 633 nanometers while transmitting light having wavelengths of about 325 nanometers. The second dichroic mirror 20 is positioned such that the light beam 19 is reflected by the second dichroic mirror 20 while the output laser light beam of the third laser 16 is transmitted through the second dichroic mirror 20. As such, the resulting laser light beam 21 includes wavelengths of the output laser light beam of the first laser 12, wavelengths of the output laser light beam of the second laser 14, and wavelengths of the output laser light beam of the third laser 16.

The flow cytometer 10 also includes a focusing lens 22, which is positioned to receive the laser light beam 21 generated by the lasers 12, 14, 16. The focusing lens 22 is configured to focus the laser light beam 21 onto a flow cell 24 wherein the sample (e.g., blood sample) to be analyzed is positioned. It should be appreciated that the flow cell 24 may be embodied as a channel through which the sample flows in some embodiments. In one particular embodiment, the flow cell 24 is embodied as a channel having a width of about 100 nanometers, but channels having other dimensions may be used in other embodiments.

A portion of the laser light beam 21 directed onto the flow cell 24 is scattered by the sample. The scattering of the laser light beam 21 forms a forward scattered light (FSC) beam 25, which is received by a forward scattered light (FSC) detector 26. The forward scatter light is generally proportional to cell-surface area or size and is a measurement of the amount of diffracted light. In addition to scattering, the laser light beam 21 excites the ligand conjugates contained in the sample. In response to the laser light beam 21, the fluorescent molecules of the ligand conjugates emit a light having a number of different wavelengths via epifluorescence. A portion of the emitted light from the fluorescent molecules is directed through a fluorescence collection lens 28.

The fluorescence collection lens 28 directs the emitted light from the fluorescent molecules to a third dichroic mirror 30. Similar to the first and second dichroic mirrors 18, 20, the third dichroic mirror 30 is configured to transmit a predetermined first wavelength or range of wavelengths of light while reflecting a second wavelength or range of wavelengths of light. In the illustrative embodiment of FIG. 8, the third dichroic mirror 20 is a shortpass dichroic mirror, which is configured to transmit light having a wavelength of about 620 nanometers or less and reflect light having a wavelength greater than about 620 nanometers.

The light having a wavelength greater than about 620 nanometers is reflected to a fourth dichroic mirror 32. The fourth dichroic mirror 32 is a longpass dichroic mirror, which is configured to transmit light having a wavelength of about 670 nanometers or greater and reflect light having a wavelength less than about 670 nanometers. The light transmitted by the fourth dichroic mirror 32 (i.e., light having a wavelength of about 670 nanometers or greater) is received by a first optical filter 34. The first optical filter 34 is a longpass optical filter and is configured to transmit light having a wavelength equal to or greater than a predetermined wavelength while blocking light of wavelengths less than the predetermined wavelength. In the illustrative embodiment, the first optical filter 34 is configured to transmit light having a wavelength of about 670 nanometers or greater and block light having a wavelength less than about 670 nanometers. The transmitted light from the first optical filter 34 is directed to a first detector 36, such as a photomultiplier tube (PMT). In some embodiments, the first detector 36 is configured to convert the received light into an analog signal.

Referring back to the fourth dichroic mirror 32, the light reflected by the mirror 32 (i.e., light having a wavelength less than about 670 nanometers) is directed to a second optical filter 38. The second optical filter 38 is a bandpass optical filter and is configured to transmit light having a wavelength within a predetermined range of wavelengths while blocking light of wavelengths other than the predetermined range. In the illustrative embodiment, the second optical filter is configured to transmit light having a wavelength of about 660 nanometers ±13 nanometers (i.e., light having a wavelength within the range of about 647 nanometers to about 673 nanometers). The transmitted light from the second optical filter 38 is directed to a second detector 40, such as a photomultiplier tube (PMT). In some embodiments, the second detector 40 is configured to convert the received light into an analog signal.

Referring back to the third dichroic mirror 30, the light transmitted through the mirror 30 (i.e., light having wavelengths of about 620 nanometers or less) is directed to a fifth dichroic mirror 42. The fifth dichroic mirror 42 is configured to transmit a predetermined first wavelength or range of wavelengths of light while reflecting a second wavelength or range of wavelengths of light. In the illustrative embodiment of FIG. 8, the fifth dichroic mirror 42 is a longpass dichroic mirror, which is configured to transmit light having a wavelength of about 510 nanometers or greater and reflect light having a wavelength less than about 510 nanometers.

The light having a wavelength less than about 510 nanometers is reflected to a sixth dichroic mirror 44. The sixth dichroic mirror 44 is also embodied as a longpass dichroic mirror, which is configured to transmit light having a wavelength of about 470 nanometers or greater and reflect light having a wavelength less than about 470 nanometers. The light transmitted by the sixth dichroic mirror 44 (i.e., light having a wavelength of about 470 nanometers or greater) is received by a third optical filter 46. The third optical filter 46 is a bandpass optical filter similar to the second optical filter 38. The third optical filter 46 is configured to transmit light having a wavelength within a predetermined range of wavelengths while blocking light of wavelengths other than the predetermined range. In the illustrative embodiment, the third optical filter 46 is configured to transmit light having a wavelength of about 510 nanometers ±10 nanometers (i.e., light having a wavelength within the range of about 500 nanometers to about 520 nanometers). The transmitted light from the third optical filter 46 is directed to a third detector 48, such as a photomultiplier tube (PMT). In some embodiments, the third detector 48 is configured to convert the received light into an analog signal.

Referring back to the sixth dichroic mirror 44, the light reflected by the mirror 44 (i.e., light having a wavelength less than about 470 nanometers) is directed to a fourth optical filter 50. The fourth optical filter 50 is a longpass optical filter and is configured to transmit light having a wavelength equal to or greater than a predetermined wavelength while blocking light of wavelengths less than the predetermined wavelength. In the illustrative embodiment, the fourth optical filter 50 is configured to transmit light having a wavelength of about 380 nanometers or greater and block light having a wavelength less than about 380 nanometers. The transmitted light from the fourth optical filter 50 is directed to a fourth detector 52, such as a photomultiplier tube (PMT). Again, in some embodiments, the fourth detector 52 is configured to convert the received light into an analog signal.

Referring now back to the fifth dichroic mirror 42, the light transmitted by the mirror 42 (i.e., light having a wavelength greater than about 510 nanometers) is directed to a seventh dichroic mirror 54. The seventh dichroic mirror 54 is configured to transmit a predetermined first wavelength or range of wavelengths of light while reflecting a second wavelength or range of wavelengths of light. In the illustrative embodiment of FIG. 8, the seventh dichroic mirror 54 is a longpass dichroic mirror, which is configured to transmit light having a wavelength of about 555 nanometers or greater and reflect light having a wavelength less than about 555 nanometers.

The light transmitted by the seventh dichroic mirror 54 (i.e., light having a wavelength of about 555 nanometers or greater) is received by a fifth optical filter 56. The fifth optical filter 56 is a bandpass optical filter and is configured to transmit light having a wavelength within a predetermined range of wavelengths while blocking light of wavelengths other than the predetermined range. In the illustrative embodiment, the fifth optical filter 56 is configured to transmit light having a wavelength of about 575 nanometers ±25 nanometers (i.e., light having a wavelength within the range of about 550 nanometers to about 600 nanometers). The transmitted light from the fifth optical filter 56 is directed to a fifth detector 58, such as a photomultiplier tube (PMT). In some embodiments, the fifth detector 58 is configured to convert the received light into an analog signal.

Referring back to the seventh dichroic mirror 54, the light reflected by the mirror 54 (i.e., light having a wavelength less than about 55 nanometers) is directed to a sixth optical filter 60. The sixth optical filter 60 is also a bandpass optical filter and is configured to transmit light having a wavelength within a predetermined range of wavelengths while blocking light of wavelengths other than the predetermined range. In the illustrative embodiment, the sixth optical filter 60 is configured to transmit light having a wavelength of about 530 nanometers ±28 nanometers (i.e., light having a wavelength within the range of about 502 nanometers to about 558 nanometers). The transmitted light from the sixth optical filter 60 is directed to a sixth detector 62, such as a photomultiplier tube (PMT). In some embodiments, the sixth detector 62 is configured to convert the received light into an analog signal.

Additionally, in some embodiments, the flow cytometer 10 may include a seventh optical filter 64 configured to receive side scattered light (SSC) via the fluorescence collection lens 26, the third dichroic mirror 30, and the fifth dichroic mirror 42. The side scattered light (SSC) is proportional to the cell granularity or internal complexity of the sample positioned in the flow cell 24. The seventh optical filter is a bandpass optical filter and is configured to transmit light having a wavelength within a predetermined range of wavelengths while blocking light of wavelengths other than the predetermined range. In the illustrative embodiment, the seventh optical filter 64 is configured to transmit light having a wavelength of about 488 nanometers ±25 nanometers (i.e., light having a wavelength within the range of about 463 nanometers to about 513 nanometers). The transmitted light from the seventh optical filter 64 is directed to a seventh detector 66, such as a photomultiplier tube (PMT). In some embodiments, the seventh detector 66 is configured to convert the received light into an analog signal.

The flow cytometer 10 may also include additional circuitry for conditioning, amplifying, and/or displaying the signals generated by the detectors 26, 36, 40, 48, 52, 58, 62, 66. For example, the flow cytometer 10 may include a preamplifier (not shown) and/or filter block (not shown) for amplifying and conditioning the generated signals. Additionally, in embodiments wherein the detectors 26, 36, 40, 48, 52, 58, 62, 66 are configured to generate analog signals, the flow cytometer 10 may include an analog-to-digital converter (not shown) for converting the analog signals into digital signals usable by, for example, a computer system (not shown). Such a computer system 54 may include a processor and other circuitry configured to process the digital signals into an image, such as a colored image, viewable on a display device of the computer system.

Although one exemplary flow cytometer has been described herein, it should be appreciated that in other embodiments other types of flow cytometers may be used to perform the ex vivo multi-photon flow cytometry process described herein. Additionally, although dichroic mirrors and optical filters have been described with reference to specific wavelength values, it should be appreciated that in other embodiments, dichroic mirrors and/or optical filters usable with other wavelength specifications may be used in other embodiments.

The following examples are illustrative embodiments only and are not intended to be limiting.

Example 1

Materials

Fmoc-Lys(Mtt)-Wang resin, Fmoc-Glu-OtBu, HOBT (1-hydroxybenzotriazole) and HBTU (2-(1H-benzotriazole-1-yl)-1,1,3,3-tetramethyluronium hexafluorophosphate) were purchased from Novabiochem (San Diego). Piperidine, DIPEA (diisopropylethylamine), Rhodamine B isothiocyanate (Rd-ITC) and triisopropyl saline (TIPS) were from Aldrich (Milwaukee). DiIC$_{18}$ (3) and fluorescein isothiocyanate (FITC) were purchased from Molecular Probes (Invitrogen). The PD-10 column (Sephadex G-25M) was from Amersham. EC17 (folate-FITC), rabbit sera, and the folate-binding column were provided by Endocyte, Inc.

Example 2

Cell Culture

Nasopharyngeal cancer cells (KB cells) were cultured in folate-deficient RPMI 1640 (Gibco) plus 10% fetal bovine serum (or calf serum) at pH 7 and incubated at 37° C.

Example 3

Solid Phase Synthesis of Folate Conjugates

The precursor of folate, N$^{10}$-TFA-Pteroic acid was synthesized according to standard procedures. Fmoc-Lys(Mtt)-Wang resin was soaked in DMF for 20 minutes with nitrogen bubbling before the reaction. 20% piperidine was added to cleave the Fmoc protective group. 2.5 e.q. Fmoc-Glu-OtBu, HOBT and HBTU, dissolved in DMF, as well as 4 e.q. DIPEA were added to the reaction funnel. After 2 hours of nitrogen bubbling at room temperature, the Fmoc cleavage step was repeated with 20% piperidine. 1.5 e.q. N$^{10}$-TFA-Pteroic acid and 2.5 e.q. HOBT and HBTU, dissolved in 1:1 DMF/DMSO (dimethylformamide/dimethylsulfoxide), as well as 4 e.q. DIPEA were then added to the reaction for 4 hours with bubbling with nitrogen. The product was then washed with DMF, DCM (dichloromethane), methanol and isopropyl alcohol thoroughly and dried under nitrogen. 1% TFA/DCM (trifluoroacetic acid/dichloromethane) was used to cleave the Mtt (Mtt=4-methyltrityl) group. 2.5 e.q. Rd-ITC, dissolved in DMF, and 4 e.q. DIPEA were added to the resin and reaction was carried out at room temperature overnight under reduced light conditions. Cleavage of the conjugates was achieved by TFA:TIPS:H$_2$O (95:2.5:2.5). The crude product was collected by precipitation with cool ether. The crude product was lyophilized overnight. On the second day, the crude product was hydrolyzed using 10% ammonium hydroxide (pH=10) for 45 minutes with nitrogen bubbling. The product was collected by lyophilization. Purification was carried out using preparative HPLC (Rigel).

Example 4

Antibody Purification and Conjugation

Anti-folate receptor polyclonal antibodies PU9, PU10 and PU17 were purified from anti-rabbit serum using a folate affinity column. The samples were desalted using a PD-10 column and then the samples were buffered in PBS (pH 8.0). Conjugation was carried out at a ratio of 80 μg of FITC per mg of antibody at room temperature for 4 hours under reduced light conditions. After conjugation, the labeled antibodies were purified by affinity column chromatography. The samples were desalted using a PD-10 column and then the samples were buffered in PBS (pH=7.4). The antibody concentration and FITC-to-protein ratio were calculated, respectively, as follows using UV/Vis absorbance: C (mg/ml)=[A (280)-0.31*A (495)]/1.4, F/P ratio=3.1*A (495)/[A (280)-0.31*A (495)].

Example 5

Blood Samples

To perform the multi-photon flow cytometry assays, experiments were carried out using fresh blood samples collected in anticoagulant from ovarian cancer patients. The blood samples were treated with folate-ALEXAFLUOR 488 before examination by flow cytometry.

Example 6

Imaging

Flow cytometry was performed with a laser scanning microscope (IX70/FV300, Olympus Inc.) that permits confocal, non-confocal, and two-photon excitation fluorescence (TPEF) imaging. A 543-nm He—Ne Laser was used for non-confocal and confocal fluorescence imaging with output power of 1 mW out of the objective. A femtosecond Ti-sapphire laser (Mira900, Coherent Inc.) was used for TPEF with an output power of 35 mW out of the objective. The pulse duration is 100 fs at 800 nm and the repetition rate is 77 MHz.

Data were acquired either by two-dimensional XY scanning or by one dimensional scanning of blood samples.

Example 7

Comparison of Labeling Between Folate Receptor-Positive Tumor Cells Using Folate Conjugates and Anti-Folate Receptor Polyclonal Antibodies Flow cytometry assays of the labeling intensities of folate-FITC (1) and three different anti-FR polyclonal antibodies conjugated with FITC: PU9 (2), PU10 (3) and PU17 (4) were performed. Unlabeled KB cells (5) and KB cells incubated with 5 µM folic acid plus 50 nM folate-FITC (6, fully competed) served as negative controls. Cultured KB cells were incubated for 30 min at 37° C. with each of the above probes before analysis by flow cytometry. The average fluorescence intensities of folate-FITC labeled KB cells are two orders magnitude higher than that of any anti-folate receptor (FR) polyclonal antibody-labeled KB cells (FIG. 1). This result was unexpected, since antibodies can be labeled with multiple FITC molecules, even though folate-FITC carries only one FITC. Further, polyclonal antibodies can bind to multiple epitopes on the FR, whereas folate-FITC only binds to a single site. This result explains the failure to detect any CTC's with fluorescent anti-tumor cell antibodies (data not shown).

Example 8

Comparison of the Methods for Separating a Tumor Cell Enriched Fraction from a Red Cell Enriched Fraction of Whole Blood Prior to Tumor Cell Labeling with Folate-Alexafluor 488

Methods to separate red cells from all other cells (i.e., a tumor cell fraction) in whole blood samples were analyzed. The methods included: 1) an antibody cocktail method described in detail in Example 9 and FIG. 3; 2) the use of A23187 which is a calcium ionophore that can shrink RBCs for better separation from white cells; 3) ficoll density separation which is commonly used to separate white cells from red cells; 4) ammonium chloride lysis which can generate sufficient osmotic pressure to burst RBCs without lysing other cell populations in whole blood; 5) a commercially available enrichment kit (Oncoquick, Greiner Bio-One) for quick separation of CTCs from peripheral blood samples of cancer patients; 6-8) different types of density centrifugation media with different equilibrium densities; and 9) SpinDisk tube (Greiner Bio-One) which is a centrifugation tube with a porous membrane insert ~3 ml from the bottom that allows filtration of red cells while retaining white cells above the filter. The Results are shown in FIG. 2. The best percent recovery was obtained with the antibody cocktail method plus ficoll density separation.

Example 9

Circulating Tumor Cell Enrichment Procedure: The Antibody Cocktail Method

Figure 3:
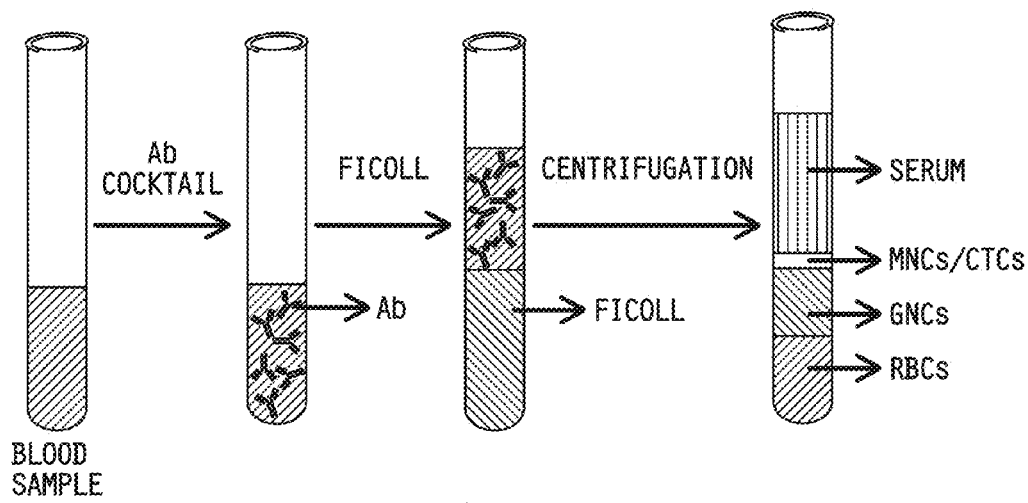
FIG. 3 is a schematic representation of the method for enrichment of circulating tumor cells from a whole blood sample.

In FIG. 3, the following abbreviations are used—CTC: circulating tumor cells, MNC: mononuclear cells, GNC: granulocytes, RBC: red blood cells, Ficoll: Separation medium, Ab Cocktail: Epithelial CTC enrichment antibody cocktail. The tetrameric antibody complexes in the antibody cocktail bridge red blood cells to unwanted white blood cells for depletion of both cell types, allowing a cleaner population of cancer cells to remain.

The following parameters were optimized for the enrichment procedure: centrifugation speed, dilution factor, centrifugation time, and pH of the separation medium. The evaluation of these parameters is shown in Tables 1-4. Generally, a centrifugation speed of approximately 1000 g for 20 minutes was optimal. Whole blood is generally too viscous and sticky for efficient CTC enrichment. Therefore, different dilutions of whole blood into PBS containing 2% fetal bovine serum (FBS) were examined. Generally, a 1:1 ratio of whole blood into PBS+2% FBS was an optimal dilution with PBS at pH 7 providing optimal labeling efficiency.

TABLE 1

Evaluation of Centrifugation Speed

| Centrifugation speed | 500 g | 1000 g | 1500 g |
| --- | --- | --- | --- |
| DiD+ (%) | 18.90 | 61.34 | 30.37 |
| FR+ Ratio out of DiD+ (%) | 97.32 | 99.22 | 97.93 |

TABLE 2

Evaluation of Dilution Factor

| Dilution Factor | 1:1 | 1:2 | 1:3 |
| --- | --- | --- | --- |
| DiD+ (%) | 61.34 | 55.83 | 60.59 |
| FR+ Ratio out of DiD+ (%) | 99.22 | 98.93 | 98.78 |

TABLE 3

Evaluation of Centrifugation Time (at 1000 g)

| Time (min) | 10 | 20 | 30 |
| --- | --- | --- | --- |
| DiD+ (%) | 50.04 | 61.34 | 45.1% |
| FR+ Ratio out of DiD+ (%) | 99.16 | 99.22 | N/A |

TABLE 4

Evaluation of Impact of pH

| pH | Citric acid pH = 5 +2% FBS | Trisbase pH = 9 +2% FBS | PBS pH = 7 +2% FBS |
| --- | --- | --- | --- |
| DiD+ (%) | 60.77 | 56.10 | 61.34 |
| FR+ Ratio out of DiD+ (%) | 90.00 | 87.63 | 99.22 |

Example 10

Preparation of an Ex Vivo Patient Sample for Detection and Quatitation of Pathogenic Cells by Flow Cytometry Assay A blood sample of 2 ml from a cancer patient was warmed at room temperature for 30 minutes. 50 µL/mL RosetteSep™ Circulating Human Epithelial Tumor Cell Extensive Enrichment Cocktail (StemCell Technologies) was added to the whole blood sample and mixed gently, then incubated for 20 minutes at room temperature. The sample was diluted with an equal volume of PBSF (PBS+2% FBS) and mixed well. Ficoll-Paque was layered underneath the diluted sample at a volume ratio of 3:4. The sample was then centrifuged for 30 minutes at 400 g at room temperature, with the brake off. The supernatant was removed from the Ficoll-Paque to another tube. 6-8 ml of PBSF was added to wash the cells, then the cells were pelleted by centrifugation at 500 g for 15 minutes. Approximately 500-1000 ul of liquid was left in the sample to resuspend the cells and folate-imaging agent 488 (100 nM). CD45-Cy5 (1:300) and Hoechst (5 ug/ml) were added to the sample. The sample was incubated on ice for 1 hour. PBSF was added to the sample to reach a volume of 5 ml. The cells were then pelleted by centrifugation at 200 g for 10 minutes. A 10× volume of PBSF was added to wash off the dye. Cells were resuspended in 1 ml PBSF for performing the flow cytometry assay. To assure that all the cells were counted by the flow cytometer, another 500 ul PBSF was added to wash the tube before performing the flow cytometry assay. When performing the above protocol, all the agents should be sterile. When transferring tubes, the tube should be washed several times to promote recovery of all the cells. New tubes should be rinsed with PBSF to reduce the non-specific adsorption of cells to the plastic walls.

Example 11

Figure 4:
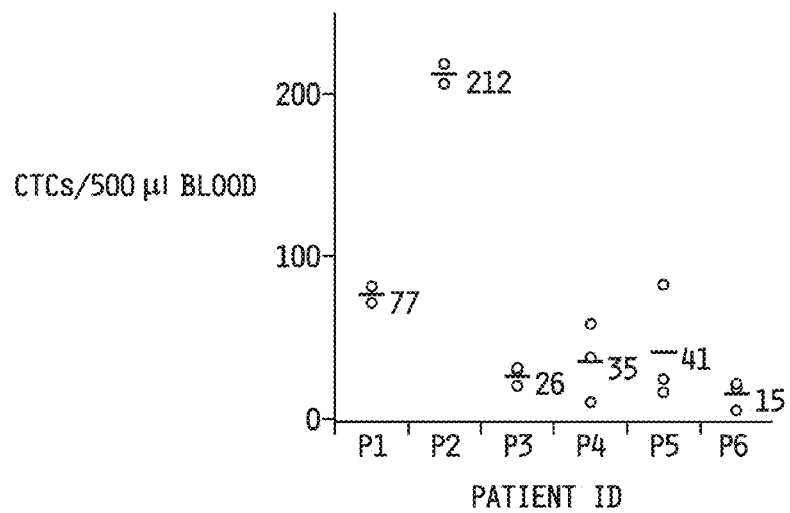
FIG. 4 shows the detection and quantification of circulating tumor cells in blood samples from ovarian cancer patients. Bars represent mean values from 2 (patients 1 and 2) or 3 independent measurements (patients 3-6).
Figure 6:
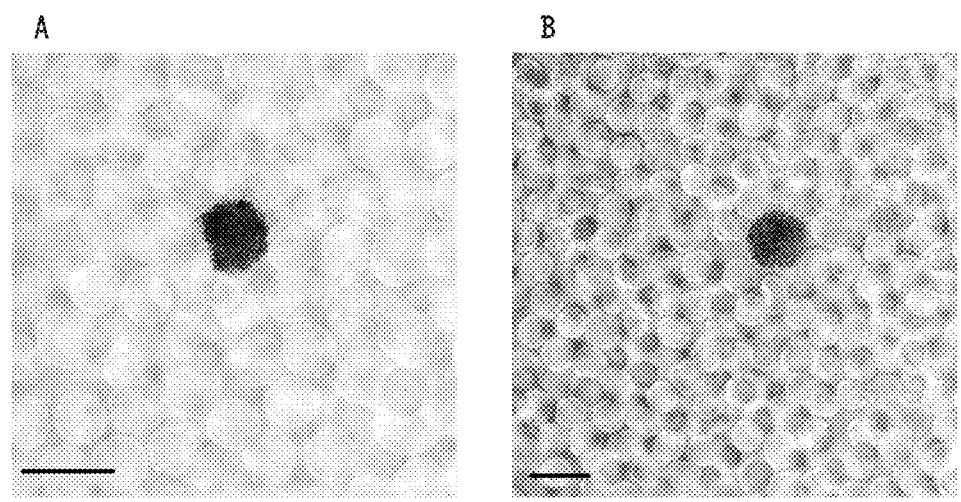
FIG. 6 (Panels A and B) shows confocal images of circulating tumor cells in peripheral blood from ovarian cancer patients. Overlap of green (folate-ALEXAFLUOR 488) with red (rhodamine-X labeled anti-cytokeratin antibody) fluorescence is displayed as yellow fluorescence (scale bar, 10 µm).

Detection of Circulating Tumor Cells in an Ex Vivo Patient Sample by Flow Cytometry and Confocal Microscopy Fresh blood samples were collected in anticoagulant from six ovarian cancer patients and were treated using the procedure described in Example 10. Five hundred microliters of whole blood from the ovarian cancer patient samples were incubated with 100 nM folate-ALEXAFLUOR 488 for 30 min at 37° C. before analysis by flow cytometry. As seen in FIG. 4, all six samples revealed measurable CTCs, ranging from 15 to 210 cells/500 μl. In contrast, similar samples from 3 healthy donors were found to contain no fluorescent particles/500 μl. To assure that the labelled cells in the ovarian cancer patients were malignant, the same peripheral blood samples were labelled with a monoclonal anti-human CA125 antibody plus the appropriate secondary antibody conjugated to rhodamine-X. As shown by confocal microscopy of a blood smear from an ovarian cancer patient shown in FIG. 6, the green fluorescence of folate-ALEXAFLUOR 488 was found to colocalize with the red fluorescence of rhodamine-X, demonstrating that the folate-ALEXAFLUOR-labelled cells indeed derive from the ovarian cancer. Overlap of green (folate-ALEXAFLUOR 488) with red (rhodamine-X labeled anti-cytokeratin antibody) fluorescence is displayed as yellow fluorescence and is seen in panels A and B of FIG. 6.

Example 12

Figure 5:
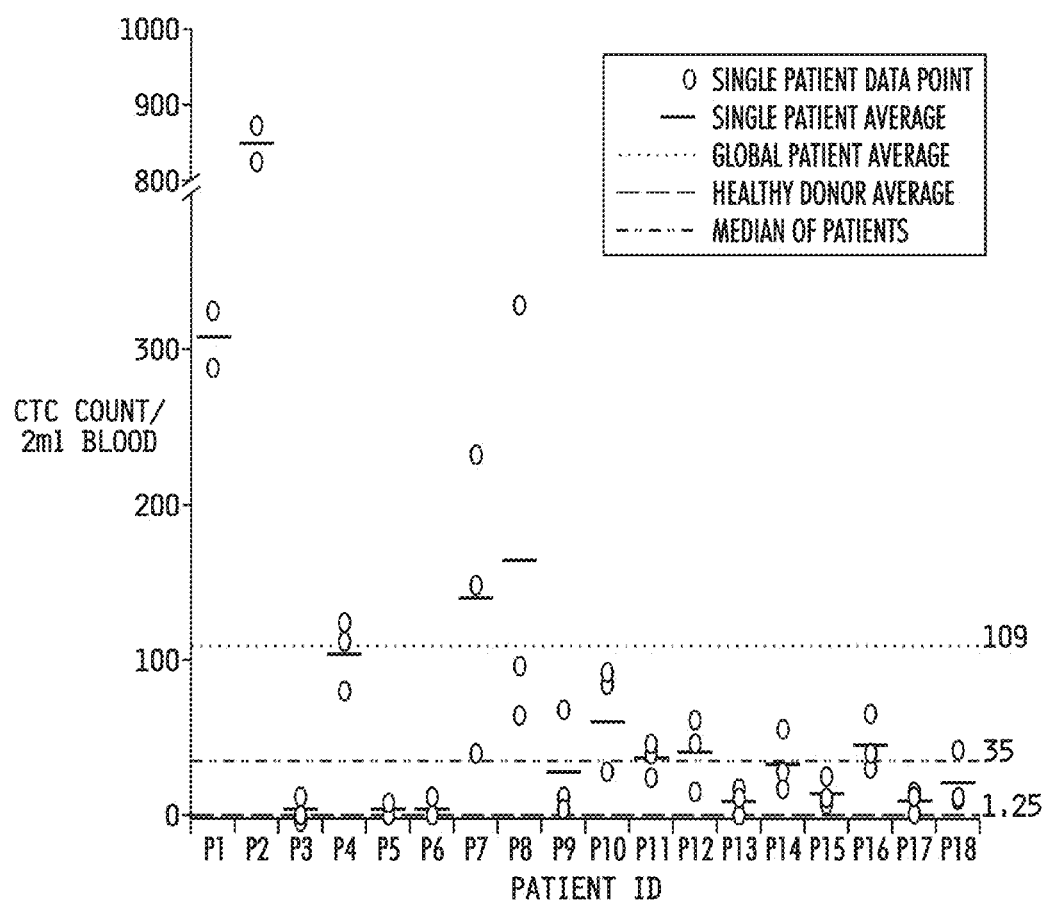
FIG. 5 shows the detection and quantification of circulating tumor cells in the blood of ovarian cancer patients using ex vivo flow cytometry.

Quantification of Circulating Tumor Cells in Ovarian Cancer Patients Using Ex Vivo Flow Cytometry Blood samples from ovarian cancer patients were analyzed by flow cytometry. Samples were treated as described in Example 10. Then, 500 ul of whole blood from patients 1-11 were incubated with 100 nM folate-ALEXAFLUOR 488 for 30 min at 37° C. before analysis by flow cytometry. A control sample for each patient sample was incubated with 10 uM folic acid for 30 min at 37° C. before the same treatment described above. For patients 12-17, 2 ml of whole blood were treated with antibody cocktail (Epithelial CTC enrichment antibody cocktail) and red blood cells were removed by using the Ficoll separation medium. The enriched tumor cell fraction was then washed and labeled with folate-ALEXAFLUOR 488 for 30 min at 4° C. before flow cytometry analysis. The results are shown in FIG. 5. Black dots represent CTC counts in each assay. The bars represent the average number of CTCs obtained in 2 or 3 independent measurements on the same blood sample. The upper dotted line represents the average CTC count for all patients. The middle dotted line represents the median CTC count for all patients. The lower black dotted line represents the average CTC count for all healthy donors. The average CTCs/2 ml of blood for the cancer patients is about 103 CTCs/2 ml, and the median is ~45 CTCs/2 ml. The lowest number of CTCs was observed in patients 3, 5 and 6, where ~5 to 10 CTCs/2 ml were detected. These numbers are above the background level found in normal blood, which averaged 1.25 CTCs/2 ml.

Example 13

Quantification of Circulating Tumor Cells in the Blood of Healthy Donors

Figure 7:
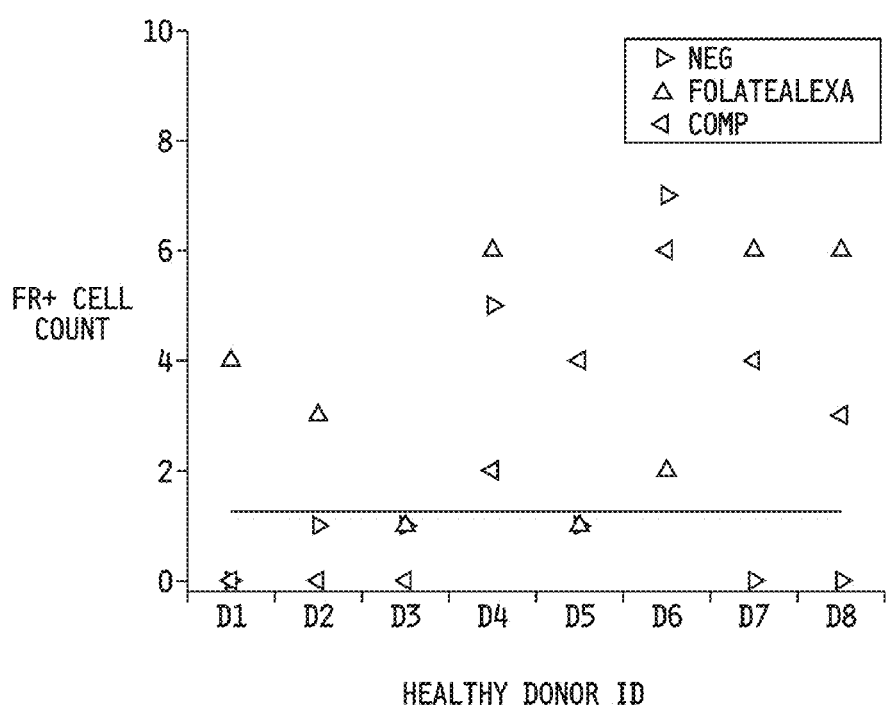
FIG. 7 shows the quantification of circulating FR-expressing cells in the blood of healthy donors.

Red blood cells were removed from six ml of whole blood from eight healthy donors using the Ficoll+Ab cocktail method, and the white cell/cancer cell fraction was washed and resuspended in 1.5 ml of PBS (2% PBS). One aliquot (500 ul cell suspension) was not labeled and served as a negative control (rightward pointing triangles). A second aliquot (upward pointing triangles) was incubated with 100 nM folate-ALEXAFLUOR 488 for 30 min at 4° C. prior to flow cytometry. The third aliquot (leftward pointing triangles) was incubated with 10 uM folic acid for 30 min at 4° C. prior to incubation with Folate-ALEXAFLUOR 488 to block any FR-specific binding. These data suggest that a CTC count (FR-expressing cell count) up to 6/2 ml can be normal (FIG. 7).

Example 14

Synthesis of Folate-Cys-Texas Red

TEXAS RED $C_2$-maleimide (Molecular Probes, Eugene, Oreg.) was dissolved in dimethyl sulfoxide (DMSO) (1 mg in 200 μl DMSO). A 1.4 molar equivalent (1 mg) of Folate-Cys was added to the solution and mixed for 4 hours at room temperature. Folate-Cys-TEXAS RED (Folate-TEXAS RED) was purified by reverse-phase HPLC on a C18 column at a flow rate of 1 ml/min. The mobile phase, consisting of 10 mM $NH_4HCO_3$ buffer, pH 7.0 (eluent A) and acetonitrile (eluent B), was maintained at a 99:1 A:B ratio for the first five minutes and then changed to 70:30 A:B in a linear gradient over the next 30 minutes followed by a 1:99 A:B linear gradient over the last 15 minutes. Folate-Cys-TEXAS RED eluted as two isomer peaks at 44.5 and 45.8 minutes. The product was confirmed by mass spectroscopy and the biologic activity was confirmed by fluorescence measurement of its binding to cell surface folate receptors on folate receptor positive M109 cells in culture.

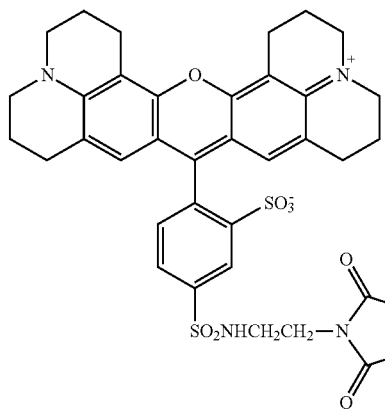
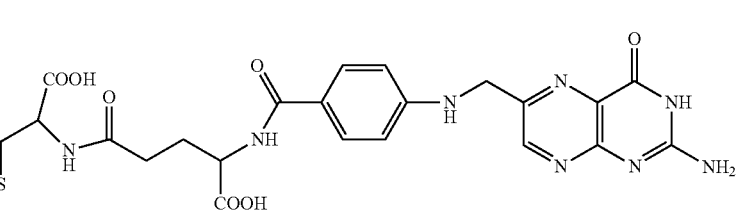

Texas Red-Cys-γ-Glu-Pteroic Acid

MW 1273.37

Example 15

Synthesis of Folate-Oregon Green 514

Standard Fmoc peptide chemistry was used to synthesize a folate peptide linked to OREGON GREEN (Molecular Probes, Eugene, Oreg.) attached to the γ-COOH of folic acid. The sequence Lys-Glu-Pteroic acid (Folate-Cys) was constructed by Fmoc chemistry with HBTU and N-hydroxybenzotriazole as the activating agents along with diisopropyethylamine as the base and 20% piperidine in dimethylformamide (DMF) for deprotection of the Fmoc groups. An α-t-Boc-protected N-α-Fmoc-L-glutamic acid followed by a $N^{10}$-trifluoroacetylpteroic acid was linked to a Fmoc-protected lysine wang resin containing a 4-methyltrityl protecting group on the ε-amine. The methoxytrityl protecting group on the ε-amine of lysine was removed with 1% trifluoroacetic acid in dichloromethane to allow attachment of OREGON GREEN (Folate-OREGON GREEN). A 1.5 molar equivalent of OREGON GREEN carboxylic acid, succinimidyl ester was reacted overnight with the peptide and then washed thoroughly from the peptide resin beads. The Folate-OREGON GREEN was then cleaved from the resin with a 95% trifluoroacetic acid-2.5% water-2.5% triisopropylsilane solution. Diethyl ether was used to precipitate the product, and the precipitant was collected by centrifugation. The product was washed twice with diethyl ether and dried under vacuum overnight. To remove the $N^{10}$-trifluoroacetyl protecting group, the product was dissolved in a 10% ammonium hydroxide solution and stirred for 30 minutes at room temperature. The product was precipitated with combined isopropanol and ether, and the precipitant was collected by centrifugation.

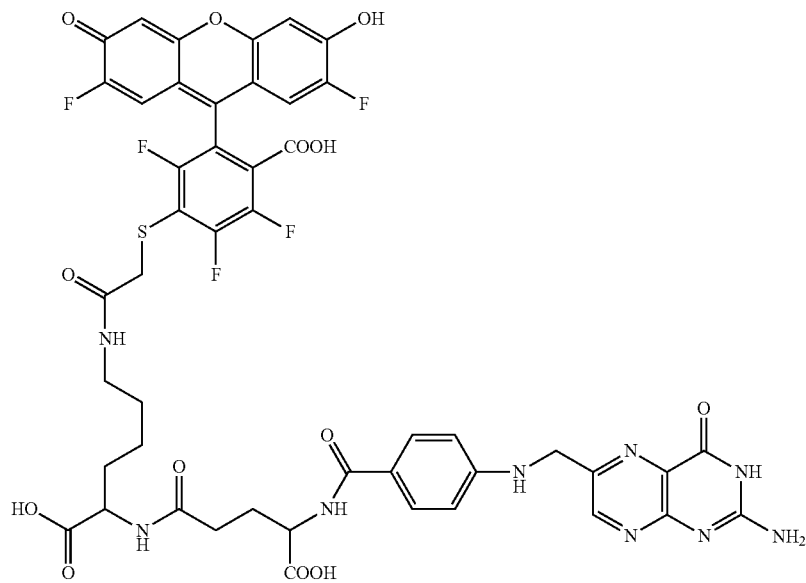 [SMILES: Nc1nc2ncc(CNc3ccc(C(=O)NC(CCC(=O)NC(CCCCNC(=O)CSc4c(F)c(F)c(C(=O)O)c(-c5c6cc(F)c(=O)cc-6oc6cc(O)c(F)cc56)c4F)C(=O)O)C(=O)O)cc3)nc2c(=O)[nH]1]

Example 16

Synthesis of Folate-R-Phycoerythrin

Folate-phycoerythrin was synthesized by following a procedure published by Kennedy M. D. et al. in *Pharmaceutical Research*, Vol. 20(5); 2003. Briefly, a 10-fold excess of folate-cysteine was added to a solution of R-phycoerythrin pyridyldisulfide (Sigma, St. Louis, Mo.) in phosphate buffered saline (PBS), pH 7.4. The solution was allowed to react overnight at 4° C. and the labeled protein (Mr ~260 kDa) was purified by gel filtration chromatography using a G-15 desalting column. The folate labeling was confirmed by fluorescence microscopy of M109 cells incubated with folate-phycoerythrin in the presence and absence of 100-fold excess of folic acid. After a 1-hour incubation and 3 cell washes with PBS, the treated cells were intensely fluorescent, while the sample in the presence of excess folic acid showed little cellular fluorescence.

Example 17

Synthesis of Folate-Fluorescein

Folate-FITC was synthesized as described by Kennedy, M. D. et al. in *Pharmaceutical Research*, Vol. 20(5); 2003.

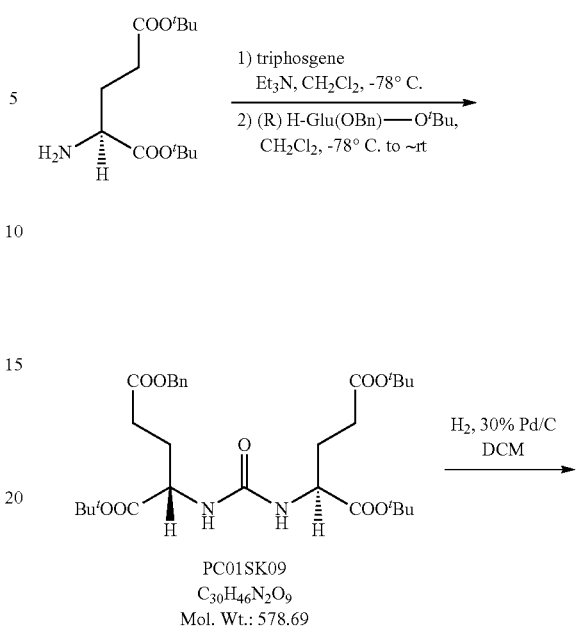

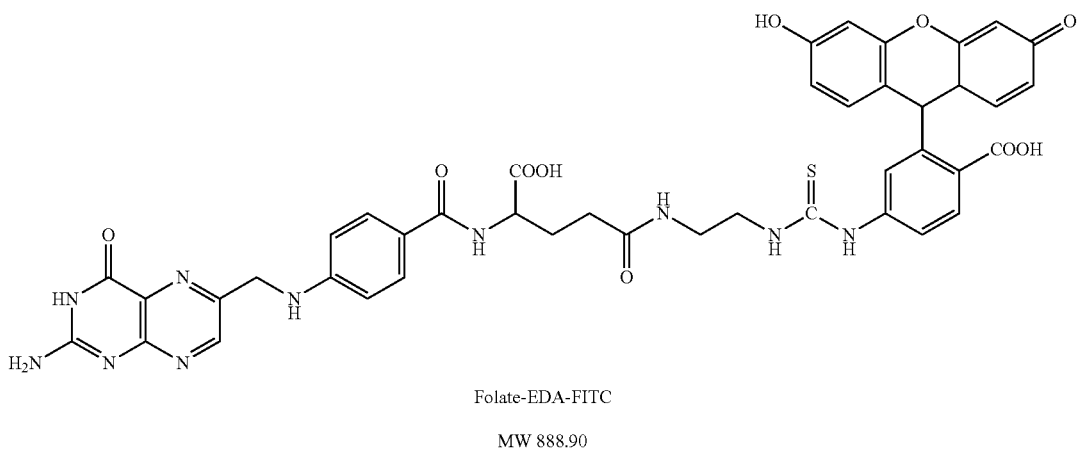 [SMILES: Nc1nc2ncc(CNc3ccc(C(=O)NC(CCC(=O)NCCNC(=S)Nc4ccc(C(=O)O)c(C5c6ccc(O)cc6OC6=CC(=O)C=CC65)c4)C(=O)O)cc3)nc2c(=O)[nH]1]

Folate-EDA-FITC

MW 888.90

Example 18

Compound Examples for Circulating Prostate Cancer Cell Detection

The compounds described herein may be prepared by conventional organic synthetic methods. In addition, the compounds described herein may be prepared as indicated below. Unless otherwise indicated, all starting materials and reagents are available from commercial supplies. All amino acid starting materials were purchased from Chem-Impex Int (Chicago, Ill.). $^1$H NMR spectra were obtained using a Bruker 500 MHz cryoprobe, unless otherwise indicated.

Example A

General synthesis of PSMA inhibitor intermediates for conjugation. Illustrated for specific synthesis of DUPA derivative 2-[3-(1,3-Bis-tert-butoxycarbonyl-propyl)-ureido]-pentanedioic acid 1-tert-butyl ester (I).

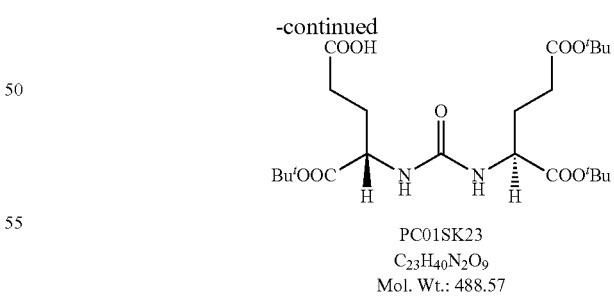

PC01SK09. To a mixture of L-glutamate di-tert-butylester HCl (1.0 g, 3.39 mmol) and triphosgene (329.8 mg, 1.12 mmol) in CH$_2$Cl$_2$ (25.0 mL) cooled to −78° C., triethylamine (1.0 mL, 8.19 mmol) was added. After stirring for 2 h at −78° C. under nitrogen, mixture of L-Glu(OBn)-O-tert-Bu (1.2 g, 3.72 mmol) and triethylamine (600 μL, 4.91 mmol) in CH$_2$Cl$_2$ (5.0 mL) was added. The reaction mixture was allowed to come to room temperature over a period of 1 h and continued to stir at room temperature overnight. The reaction mixture was washed with 1N HCl, brine and dried over $Na_2SO_4$. The crude product was purified using a flash chromatography (hexane:EtOAc=1:1, $R_f$=0.67) to give PC01SK09 (1.76 g, 90.2%). $C_{30}H_{46}N_2O_9$; MW=578.69 g/mol; colorless oil; $^1$H NMR (CDCl$_3$) δ 1.43 (s, 9H, CH$_3$-$^t$Bu); 1.44 (s, 9H, CH$_3$-$^t$Bu); 1.46 (s, 9H, CH$_3$-$^t$Bu); 1.85 (m, 1H, Glu-H); 1.87 (m, 1H, Glu-H); 2.06 (m, 1H, Glu-H); 2.07 (m, 1H, Glu-H); 2.30 (m, 2H, Glu-H); 2.44 (m, 2H, Glu-H); 4.34 [s (broad), 1H, αH]; 4.38 [s (broad), 1H, α-H]; 5.10 (s, 2H, CH$_2$—Ar); 5.22 [s (broad), 2H, Urea-H]; 7.34 (m, 5H, Ar—H). $^{13}$C NMR (CDCl$_3$) δ 28.16; 28.25; 28.54; 28.60; 30.52; 31.73; 53.13; 53.22; 66.58; 80.71; 82.25; 82.35; 128.39; 128.71; 136.03; 156.96; 172.01; 172.16; 172.65; 173.13: CI-MS=579 (M+H)$^+$, ESI-MS=579 (M+H)$^+$, 601 (M+Na adduct).

PC01SK23. To a solution of compound PC01SK09 (250 mg, 432 mmol) in CH$_2$Cl$_2$, 30% Pd/C (50 mg) was added. The reaction mixture was hydrogenated at 1 atm, room temperature for 24 h. Pd/C was filtered through celite pad and washed with CH$_2$Cl$_2$. The crude product was purified using a flash chromatography (hexane:EtOAc=40:60, $R_f$=0.58) to give PC01SK23 (169 mg, 80.2%). $C_{23}H_{40}N_2O_9$; MW=488.57 g/mol; colorless oil; $^1$H NMR (CDCl$_3$) δ 1.46 (m, 27H, CH$_3$-$^t$Bu); 1.91 (m, 2H, Glu-H); 2.07 (m, 1H, Glu-H); 2.18 (m, 1H, Glu-H); 2.33 (m, 2H, Glu-H); 2.46 (m, 2H, Glu-H); 4.31 [s (broad), 1H, αH]; 4.35 [s (broad), 1H, α-H]; 5.05 (t, 2H, Urea-H); CI-MS=489 (M+H)$^+$, ESI-MS=489 (M+H)$^+$, 511 (M+Na adduct), 487 (M−H)$^−$.

Example B

General synthesis of PSMA inhibitor intermediates for conjugation. Illustrated for specific synthesis of tertiary butyl protected MUPA derivative 2-[3-(1-tert-Butoxycarbonyl-2-mercapto-ethyl)-ureido]-pentanedioic acid di-tert-butyl ester (II).

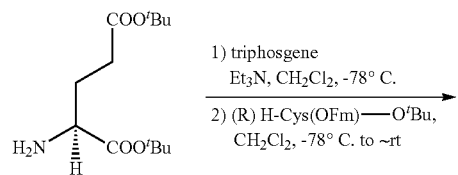

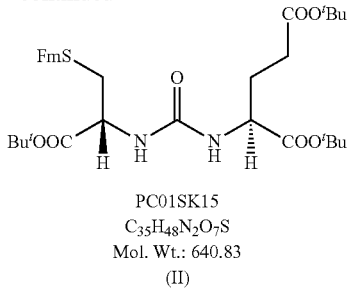

PC01SK15. To a mixture of L-glutamate di-tert-butylester HCl (200 mg, 0.676 mmol) and triphosgene (67 mg, 0.228 mmol) in CH$_2$Cl$_2$ (5.0 mL), cooled to −78° C., triethylamine (50 μL, 0.410 mmol) was added. After stirring for 2 h at −78° C. under nitrogen, mixture of D-Cys(Fm)—O$^t$Bu (291.4 mg, 0.774 mmol) and triethylamine (30 μL, 240 mmol) in CH$_2$Cl$_2$ (1.0 mL) was added. The reaction mixture was allowed to come to room temperature over a period of 1 h and continued to stir at room temperature overnight. The reaction mixture was washed with 1N HCl, brine and dried over Na$_2$SO$_4$. The crude product was purified using a flash chromatography (hexane:EtOAc=50:50, $R_f$=0.6) to give PC01SK15 (374 mg, 86.4%). $C_{35}H_{48}N_2O_7S$; MW=640.83 g/mol; pale yallow oil; $^1$H NMR (CDCl$_3$) δ 1.45 (s, 27H, CH$_3$-$^t$Bu); 1.88 (m, 1H, Glu-H); 2.10 (m, 1H, Glu-H); 2.32 (m, 2H, Glu-H); 2.97 (m, 2H, Fm—CH2); 3.13 (m, 2H, Cys-H); 4.09 (t, 1H, Fm—H); 4.38 (m, 1H, αH); 4.66 (m, 1H, α-H); 5.55 (d, 1H, Urea-H); 5.67 (d, 1H, Urea-H); 7.30 (q, 2H, Ar—H); 7.36 (q, 2H, Ar—H); 7.73 (m, 4H, Ar—H). $^{13}$C NMR (CDCl$_3$) δ 28.05; 28.14; 28.42; 31.64; 36.27; 37.25; 53.07; 53.73; 80.51; 81.98; 82.42; 119.85; 124.95; 125.09; 127.09; 127.51; 141.09; 145.99; 156.76; 170.80; 172.15; 172.43; CI-MS=641 (M+H)$^+$, ESI-MS=641 (M+H)$^+$.

Example C

General synthesis of PSMA imaging agent conjugates illustrated for PC01SK59 using Universal PSMA (DUPA) resin, a 2-atom spacer, and FITC. This conjugate may also be used for detecting circulating tumor cells in prostate cancer patients.

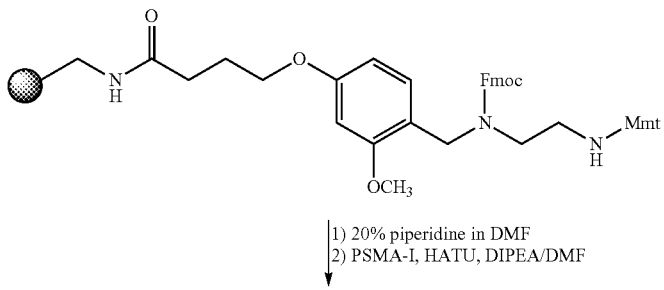

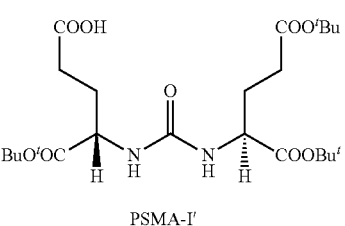

-continued

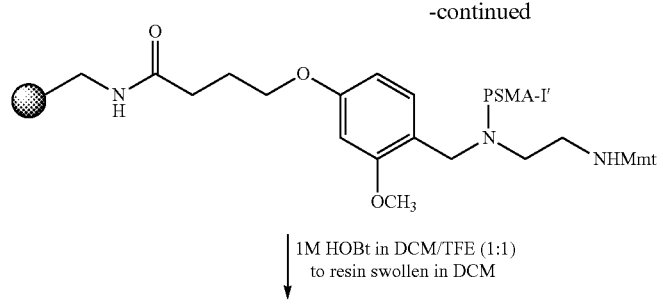

1M HOBt in DCM/TFE (1:1) to resin swollen in DCM

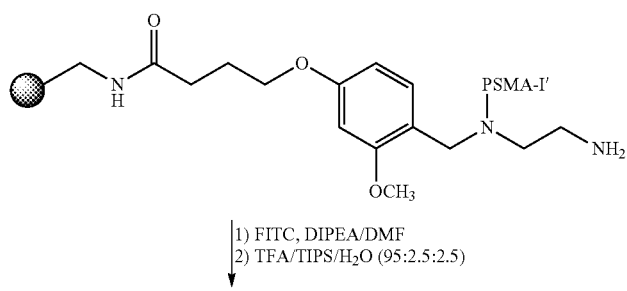

1) FITC, DIPEA/DMF
2) TFA/TIPS/H$_2$O (95:2.5:2.5)

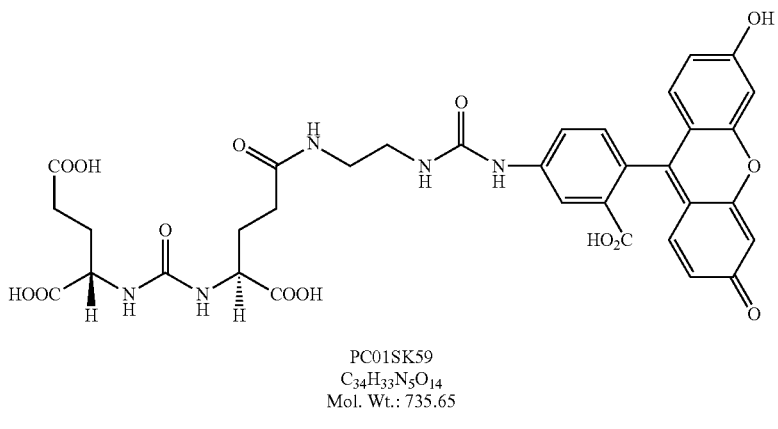

PC01SK59
C$_{34}$H$_{33}$N$_5$O$_{14}$
Mol. Wt.: 735.65

Synthesis of PSMA universal resin and PC01SK59. Universal PSMA ligand (DUPA) resin was synthesized using Universal NovaTag™ resin (Novabiochem; Catalog #04-12-3910). Fmoc group was deprotected using 20% piperidine/DMF (N,N-dimethylformamide), after swelling the resin with DCM (CH$_2$Cl$_2$) and DMF. tert-Butyl protected DUPA was coupled using HATU [2-(1H-7-azabenzotriazol-1-yl)-,1,3,3-tetramethyl uronium hexafluorophosphate] and DIPEA (N,N-diisopropylethylamine) in DMF. The pendant Mmt (4-Methoxytrityl) was removed with 1M HOBT (1-Hyroxybenzotriazole) in DCM/TFE (trifluoroethanol). The resin intermediate can be washed with DMF and used immediately in subsequent synthetic steps or washed with DCM/DMF and then with MeOH, and dried for later use.

Universal PSMA resin was reacted with commercially available FITC (1.25 equiv) in the presence of DIPEA (4 equiv) in DMF to yield PC01SK59 (2 atom spacer) construct. The final compound was cleaved from the resin using a mixture of TFA (trifluoro acetic acid), TIPS (triisopropylsilane), and water. Purification was by reverse phase preparative HPLC (Waters, xTerra C$_{18}$ 5 μm; 19×150 mm) A=10 mM NH$_4$OAc, B=ACN; λ=488 nm; Solvent gradient: 1% B to 50% B in 25 min, 80% B wash 40 min run, (63%). PC01SK59 was analyzed using reverse phase analytical HPLC (Waters, X-Bridge C$_{18}$ 5 μm; 3.0×15 mm); A=10 mM NH$_4$OAc, B=ACN; λ=488 nm, 1% B to 50% B in 10 min, 80% B wash 15 min run; C$_{34}$H$_{33}$N$_6$O$_{13}$S; MW=751.72 g/mol; orange color solid, R$_f$=7.2 min; ESI-MS=752 (M+H)$^+$; 774 (M+Na)$^+$; 750 (M−H)$^−$.

Example D

General synthesis of PSMA imaging agent conjugates illustrated for PC01SK64 using Universal PSMA (DUPA) resin, a 16-atom spacer, and FITC.

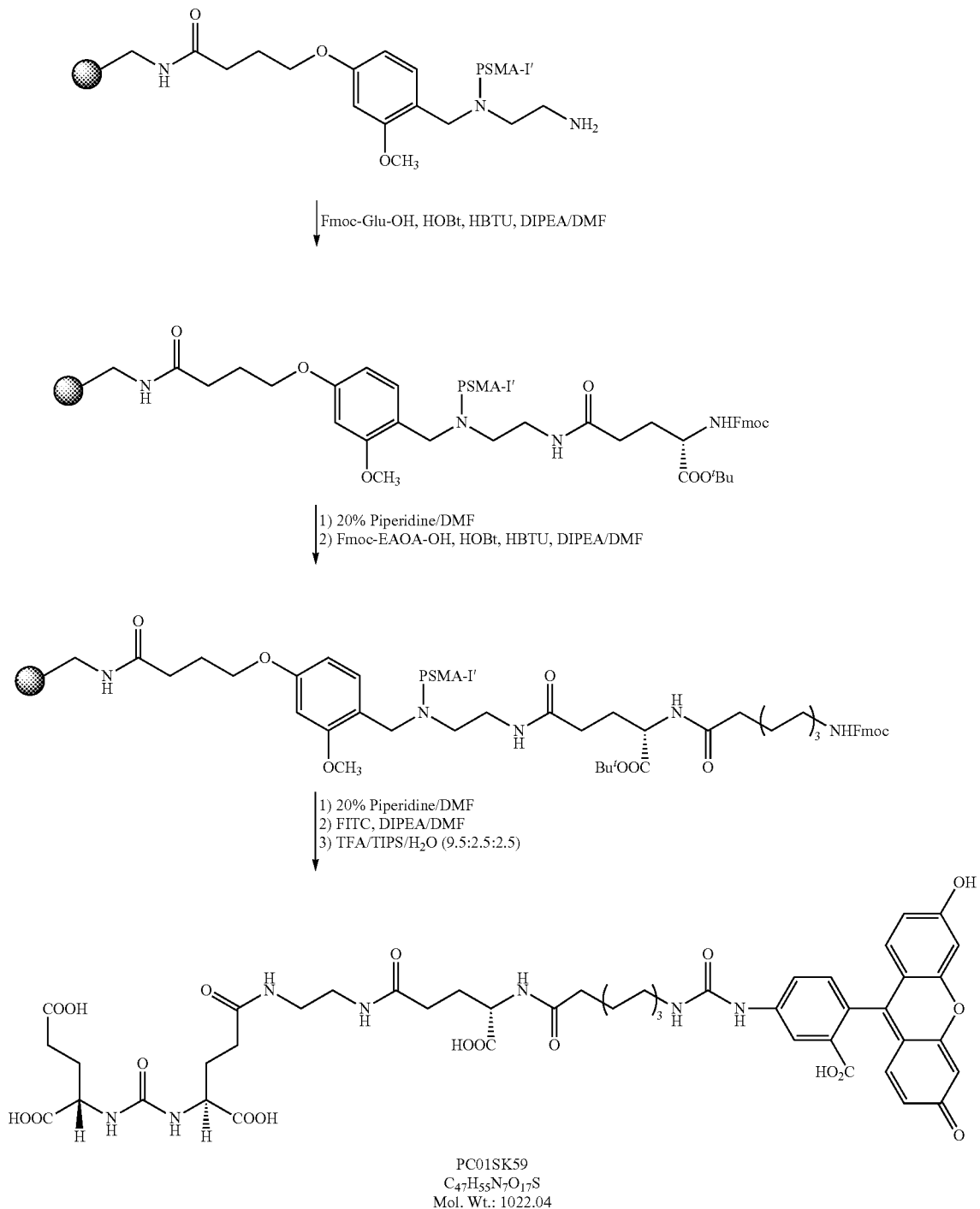

Universal PSMA resin was coupled with Fmoc-Glu-(OtBu)-OH and Fmoc-EAOA (8-aminooctonoic acid) using standard Fmoc SPPS. After conjugating with fluoroisothiocyanate (1.25 equiv) in the presence of DIPEA (4 equiv) in DMF, PC01SK64 (16 atom spacer) compound was cleaved from the resin using TFA/TIPS/H2O. Purification was performed using reverse phase preparative HPLC (Waters, xTerra C18 5 μm; 19×150 mm) A=10 mM NH4OAc, B=ACN; λ=488 nm; Solvent gradient: 1% B to 50% B in 25 min, 80% B wash 40 min run, (57%). PC01SK64 was analyzed using reverse phase analytical HPLC (Waters, X-Bridge C18 5 μm; 3.0×150 mm); A=10 mM NH4OAc, B=ACN; λ=488 nm, 1% B to 50% B in 10 min, 80% B wash 15 min run; C47H55N7O17 S; MW=1022.04 g/mol; orange color solid, Rt=7.8 min; ESI-MS=1022 (M+H)+; 1020 (M−H)−.

Examples E-F

The following compounds were prepared using the synthetic processes described herein:

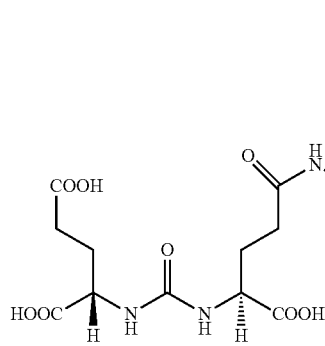
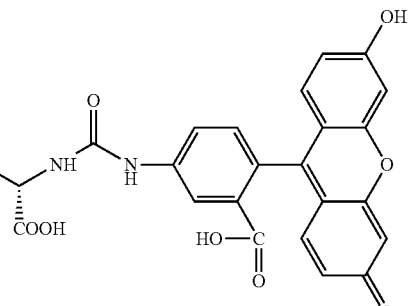

PC01SK63(7-atom spacer, C39H40N6O17, Mol. Wt.: 864.76). was prepared using universal PSMA resin and standard Fmoc SPPS conjugated with Fmoc-Glu-(O^tBu)-OH. After coupling with FITC, compounds were cleaved from the resin using TFA/TIPS/H$_2$O cocktail and purified with reverse phase preparative HPLC (Waters, xTerra C$_{18}$ 5 μM; 19×150 mm) A=10 mM NH$_4$OAc, B=ACN; λ488 nm; Solvent gradient: 1% B to 50% B in 25 min, 80% B wash 40 min run, (65%); analyzed using reverse phase analytical HPLC (Waters, X-Bridge C$_{18}$ 5 μm; 3.0×150 mm); A=10 mM NH$_4$OAc, B=ACN; λ=488 nm, 1% B to 50% B in 10 min, 80% B wash 15 min run; PC01SK63: C$_{39}$H$_{40}$N$_6$O$_{16}$S; MW=880.83 g/mol; orange color solid, R$_t$=6.8 min; ESI-MS=881 (M+H)$^+$; 903 (M+Na)+; 863(M−H)−.

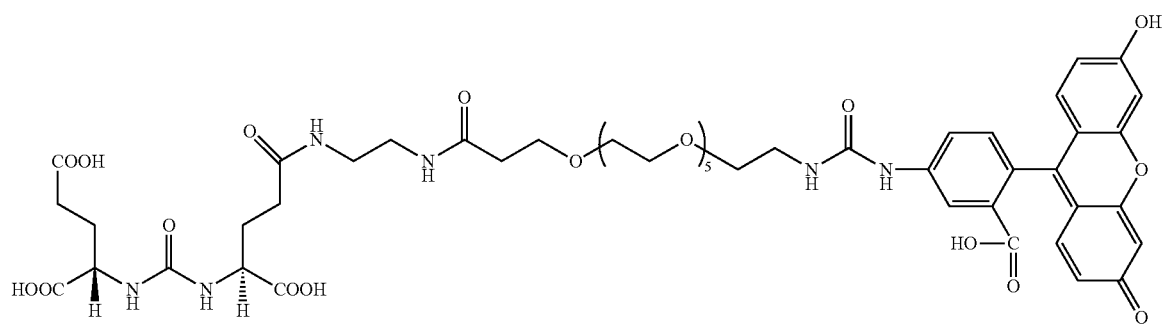

PC01SK58 (24-atom spacer, C49H62N6O20S, Mol. Wt.: 1087.11) was prepared using universal PSMA resin and standard Fmoc SPPS conjugated with Fmoc-(PEG)$_6$-OH and purified by HPLC 1% B to 60% B in 25 min, 80% B wash 40 min run, (65%); analyzed using reverse phase analytical HPLC (Waters, X-Bridge C$_{18}$ 5 μm; 3.0×150 mm); A=10 mM NH$_4$OAc, B=ACN; λ=488 nm, 1% B to 60% B in 10 min, 80% B wash 15 min run; C$_{49}$H$_{60}$N$_6$O$_{20}$S; MW=1087.11 g/mol; orange color solid, R$_t$=7.3 min; ESI-MS=1087 (M+H)$^+$; 1109 (M+Na)+; 1085 (M−H)$^-$.

Example G

General synthesis of Cys-maleimide PSMA imaging agent conjugates illustrated for PC01SK56 using Wang PSMA (DUPA) resin, a 24-atom spacer, and OREGON GREEN 488, where n=3.

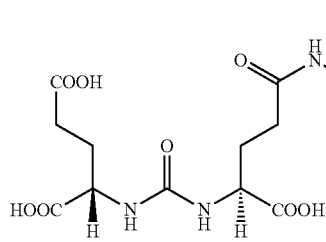
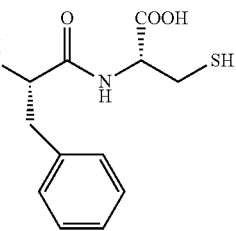

PC01SK54
C$_{38}$H$_{59}$N$_5$O$_{18}$S
Mol. Wt.: 905.96

Oregon Green 488 maleimide/THF
Water/pH~7/Ar

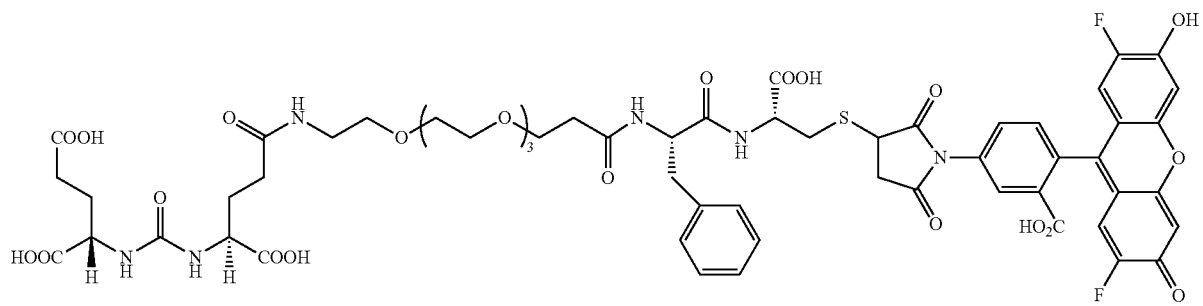

PC01SK56
C$_{62}$H$_{70}$F$_2$N$_6$O$_{25}$S
Mol. Wt.: 1369.31

Related analogs where n is an integer from 4 to about 30 may also be prepared according to the processes described herein.

PC01SK54 was prepared using standard Fmoc SPPS starting from Fmoc-Cys(Trt)-Wang resin (Novabiochem; Catalog #04-12-2050), purified using reverse phase preparative HPLC (Waters, xTerra C$_{18}$ 10 μm; 19×250 mm) A=0.1 TFA; B=ACN; λ=257 nm; Solvent gradient: 1% B to 60% B in 25 min, 80% B wash 40 min run, (63%), and analyzed using reverse phase analytical HPLC (Waters, X-Bridge C$_{18}$ 5 μm; 3.0×50 mm); A=10 mM NH$_4$OAc, B=ACN; λ=257 nm, 1% B to 50% B in 10 min, 80% B wash 15 min run; C$_{38}$H$_{59}$N$_5$O$_{18}$S, MW=905.96 g/mol; colorless solid; R$_t$=9.2 min, LC-MS=906.3 g/mol; ESI-MS=906 (M+H)$^+$; 904 (M−H)$^−$.

PC01SK56 (24 Atom spacer). HPLC grade Milli-Q water and satd NaHCO$_3$ were purged with argon for 10 min. PC01SK54 was dissolved in 1.0 mL of argon purged water while bubbling argon. The pH of the solution was increased up to 6.8 and OREGON GREEN 488 maleimide dissolved in 1.0 mL of THF was added to the reaction mixture. The reaction was monitored by analytical HPLC (10 mM NH$_4$OAc, pH=7.0; 1% B to 50% B in 10 min 80% B wash 15 min run) and reaction was completed within 10 min. THF was evaporated and reaction mixture was diluted with 5.0 mL of 7 mM phosphate buffer. Purification was performed using reverse phase preparative HPLC (Waters, xTerra C$_{18}$ 10 μm; 19×250 mm) A=7 mM Phosphate buffer pH=7.2, B=ACN; λ=488 nm; Solvent gradient: 1% B to 50% B in 25 min, 80% B wash 40 min run, (89%); and analyzed using reverse phase analytical HPLC (Waters, X-Bridge C$_{18}$ 5 μm; 3.0×150 mm); A=10 mM NH$_4$OAc, B=ACN; λ=488 nm, 1% B to 50% B in 10 min, 80% B wash 15 min run; C$_{62}$H$_{70}$F$_2$N$_6$O$_{25}$S; MW=1369.31 g/mol; orange color solid, R$_t$=7.0 min; LC-MS=1370.2; ESI-MS=1391 (M+Na)$^+$.

The following 24-atom spacer compounds were prepared in an analogous manner to those described herein using the General syntheses described herein.

Example H

The following ALEXAFLUOR 488 conjugate compound was prepared according to the processes described herein starting with PC01SK55, where n=3.

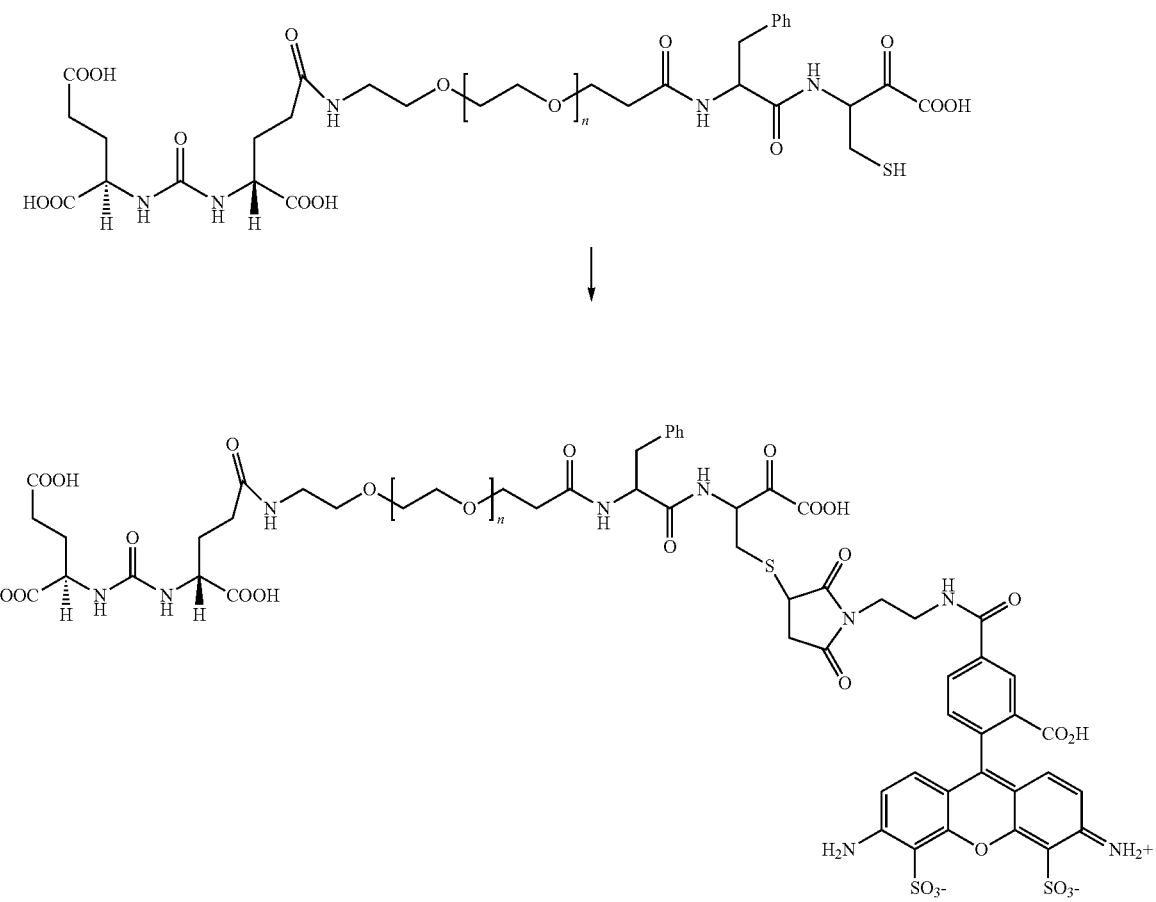

Related analogs where n is an integer from 4 to about 30 may also be prepared according to the processes described herein.

Examples I-K

The following DUPA imaging agent conjugate compounds, PC01SK51, PC01SK45, and PC01SK49 were prepared according to the processes described herein, where n is 5:

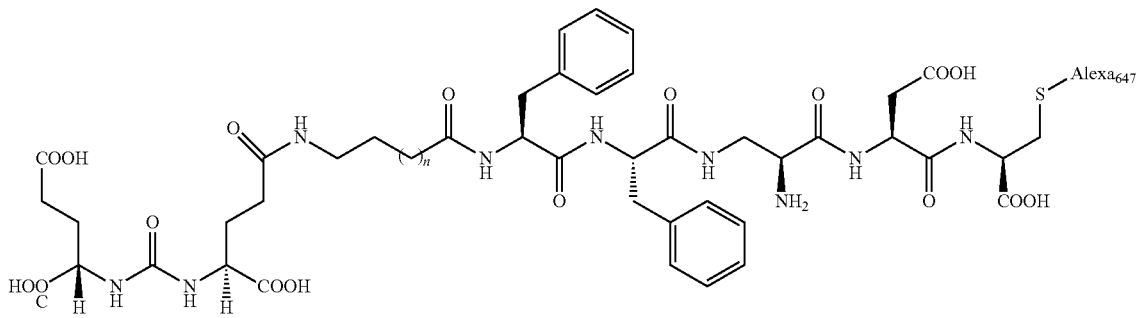

PC01SK51 (24-atom spacer, and ALEXAFLUOR 647, MW ~2300 (commercially available from Invitrogen))

Related analogs where n is an integer from 0 to about 12 may also be prepared according to the processes described herein.

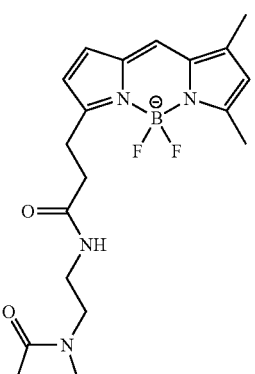
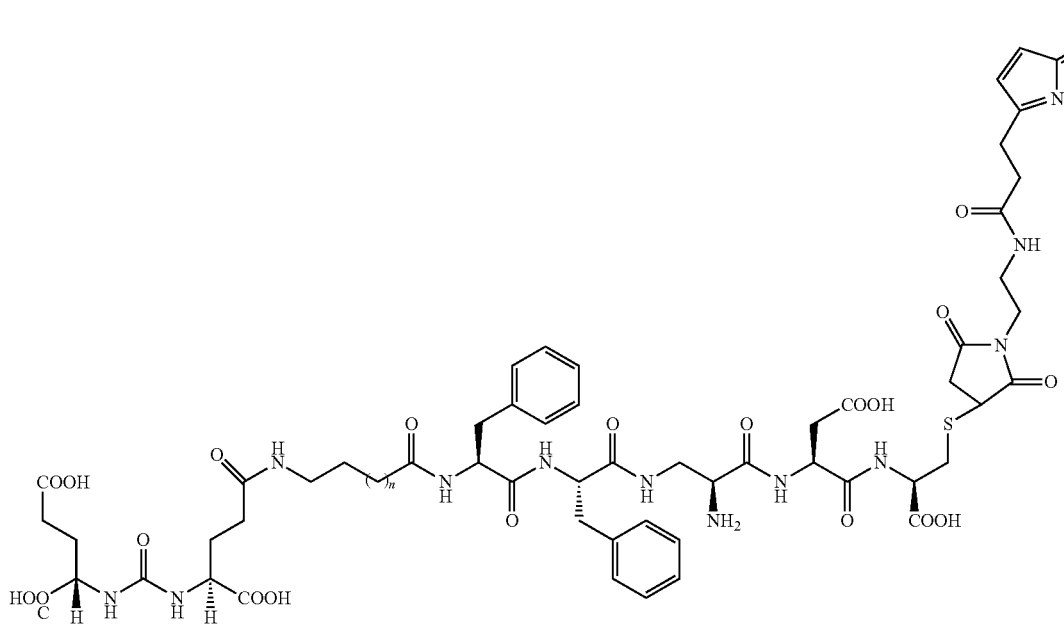
PC01SK45 (24 Atom spacer BODIPY 505, C67H87BF2N13O20S, Mol. Wt.: 1475.35)
Related analogs where n is an integer from 0 to about 12 may also be prepared according to the processes described herein.
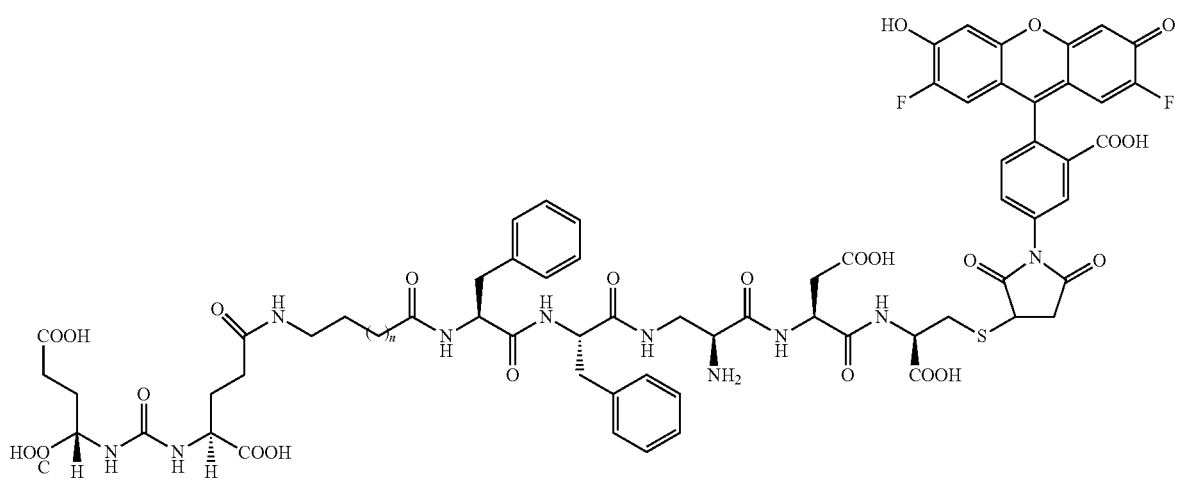

(24 Atom spacer-OREGON GREEN 488, C71H76F2N10O24, Mol. Wt.: 1523.48)

Related analogs where n is an integer from 0 to about 12 may also be prepared according to the processes described herein.

Synthesis of the Linker. In each of the foregoing Examples, the linker was synthesized using standard Fmoc SPPS starting from Fmoc-Cys(Trt)-Wang resin (Novabiochem; Catalog #04-12-2050); $C_{47}H_{65}N_2O_{17}S$; MW=1060.13 g/mol; white solid; $R_t$=7.7 min; $^1$H NMR (DMSO-$d_6$/$D_2O$) δ 0.93 (m, 2H); 1.08 (m, 5H); 1.27 (m, 5H); 1.69 (m, 2H); 1.90 (m, 2H); 1.94 (m, 2H); 2.10 (m, 2H); 2.24 (q, 2H); 2.62 (m, 2H); 2.78 (m, 4H); 2.88 (dd, 1H); 2.96 (t, 2H); 3.01 (dd, 1H); 3.31 (dd, 1H); 3.62 (dd, 1H); 3.80 (q, 1H, αH); 4.07 (m, 1H, αH); 4.37 (m, 1H, αH); 4.42 (m, 2H, αH); 4.66 (m, 1H, αH); 7.18 (m, 10H, Ar—H): LC-MS=1061 (M+H)$_+$; ESI-MS=1061 (M+H)$^+$.

Synthesis of PC01SK51 (ALEXAFLUOR 647 conjugate), PC01SK45 (BODIPY conjugate) and PC01SK49 (OREGON GREEN 488 conjugate). HPLC grade Milli-Q water and satd NaHCO$_3$ were purged with argon for 10 min. Linker was dissolved in 1.0 mL of argon purged while bubbling argon. The pH of the solution was increased up to 6.8 and ALEXAFLUOR maleimide, BODIPY maleimide, or OREGON GREEN 488 maleimide, respectively, was dissolved in 1.0 mL of tetrahydrofuran (THF) was added to the reaction mixture. Progress of the reaction was monitored by analytical HPLC (10 mM NH$_4$OAc, pH=7.0; 1% B to 50% B in 10 min 80% B wash 15 min run) and reaction was completed within 10 min. THF was evaporated and reaction mixture was diluted with 5.0 mL of 1 mM phosphate buffer (pH=7.2).

Compounds were purified using reverse phase preparative HPLC (Waters, xTerra $C_{18}$ 5 µm; 18×150 mm) A=1 mM Phosphate buffer pH=7.2, B=ACN; λ=647 or 488 nm; Solvent gradient: 1% B to 50% B in 25 min, 80% B wash 40 min run; and analyzed using reverse phase analytical HPLC (Waters, X-Bridge $C_{18}$ 5 µm; 3.0×50 mm); A=10 mM NH$_4$OAc, B=ACN; λ=588 or 488 nm, 1% B to 50% B in 10 min, 80% B wash 15 min run.

PC01SK51: MW ~2360.13 g/mol; blue color solid, $R_t$=6.7 min; (structure of the ALEXAFLUOR 647 is not known);

PC015K45: $C_{67}H_{87}BF_2N_{13}O_{20}S$; MW=1475.35 g/mol; orange color solid, $R_t$=7.6 min; LC-MS=1475.3 (M+H)$^+$;

PC01SK49: $C_{71}H_{76}F_2N_{10}O_{24}S$; MW=1523.48 g/mol; orange color solid, $R_t$=6.7 min; LC-MS=1524 (M+H)$^+$.

Example L

General synthesis of PSMA disulfide linker intermediate for conjugation, illustrated for PC01SK68.

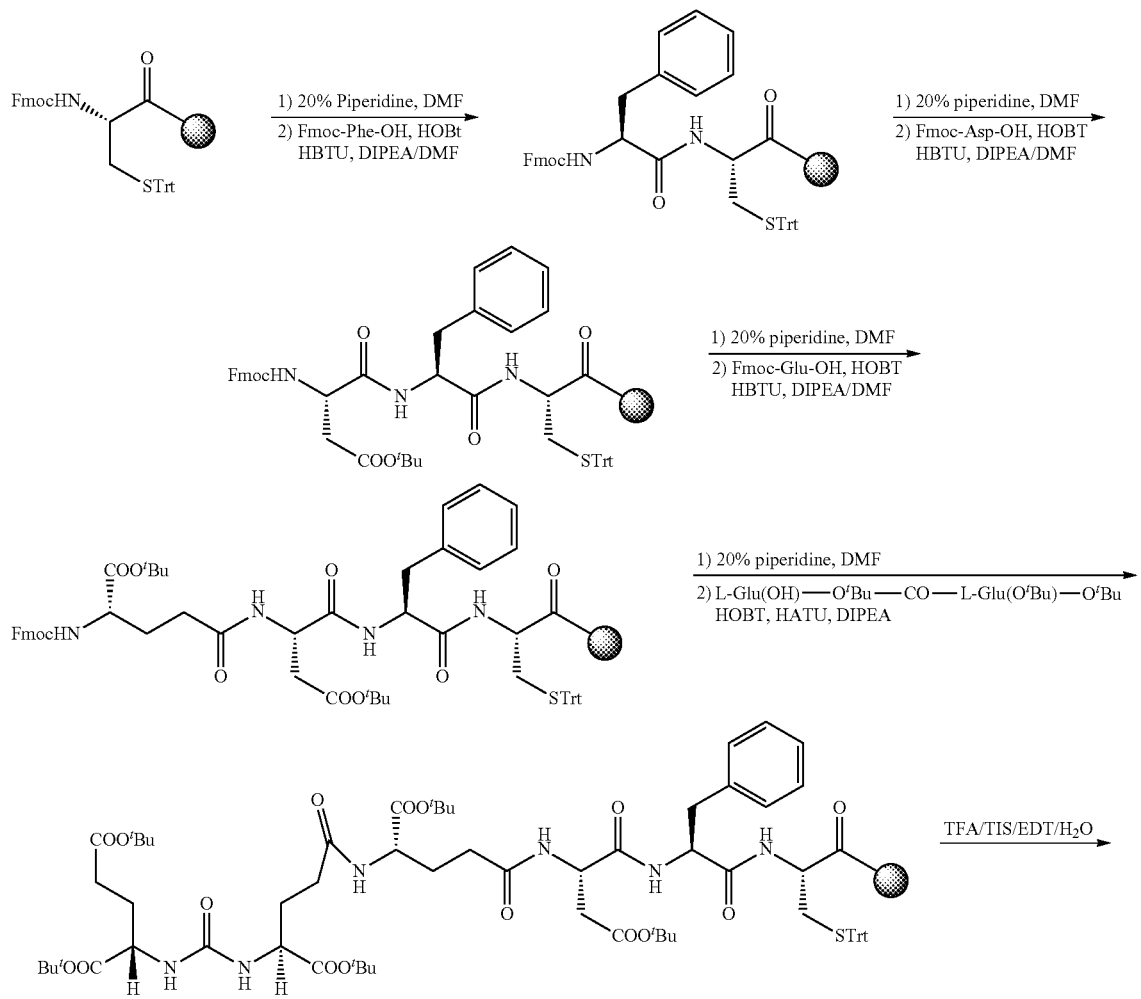

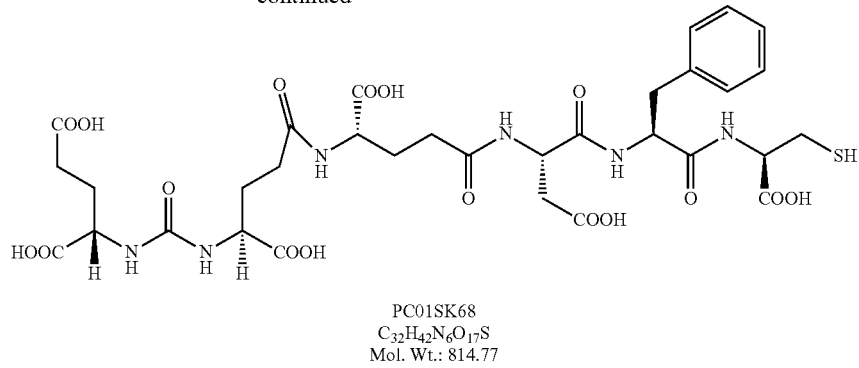

PC01SK68
C$_{32}$H$_{42}$N$_6$O$_{17}$S
Mol. Wt.: 814.77

PC01SK68 was synthesized using standard Fmoc SPPS starting from Fmoc-Cys(Trt)-Wang resin (Novabiochem; Catalog #04-12-2050), purified using reverse phase preparative HPLC (Waters, xTerra C$_{18}$ 10 µm; 19×250 mm) A=0.1 TFA, B=ACN; λ=257 nm; Solvent gradient: 1% B to 50% B in 30 min, 80% B wash 40 min run, (68%); and analyzed using reverse phase analytical HPLC (Waters, X-Bridge C$_{18}$ 5 µm; 3.0×15 mm); A=0.1 TFA, B=ACN; λ=257 nm, 1% B to 50% B in 10 min, 80% B wash 15 min run. C$_{32}$H$_{42}$N$_6$O$_{17}$S; MW=814.77 g/mol; white solid; R$_t$=8.2 min; $^1$H NMR (DMOS-d$_6$/D$_2$O) δ 1.70 (m, 3H); 1.90 (m, 3H); 2.10 (m, 2H); 2.17 (m, 2H); 2.23 (m, 2H); 2.36 (m, 1H); 2.59 (dd, 1H); 2.79 (m, 3H); 3.04 (dd, 1H); 4.07 (m, 2H, αH); 4.13 (m, 1H, αH); 4.37 [m, 1H, α-H]; 4.47 (m, 2H, α-H); 7.19 (m, 5H, Ar—H); 7.87 (d, Ures-NH); 8.20 (d, 1H, Urea-NH); LC-MS=815.3 (M+H)$^+$.

Example M

General synthesis of PSMA disulfide linker intermediate for conjugation, illustrated for PC01SK28L.

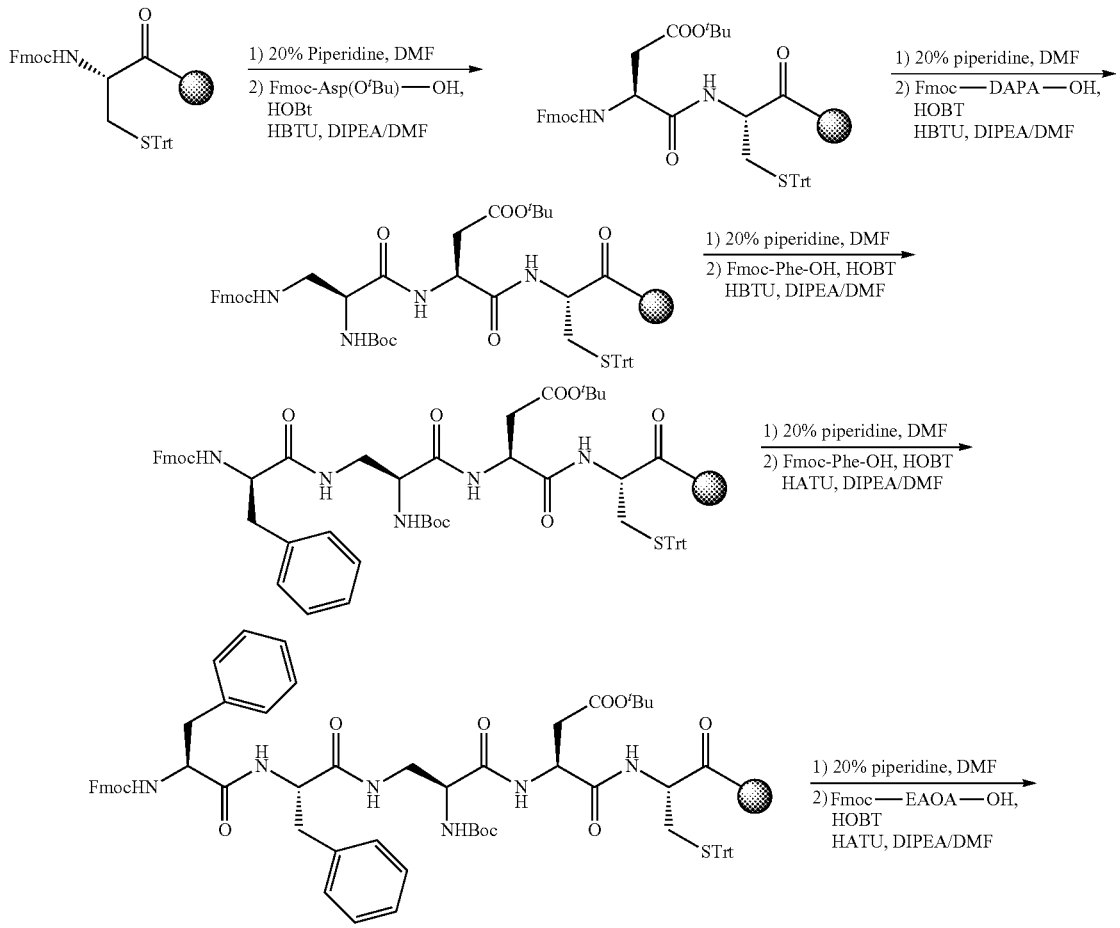

-continued

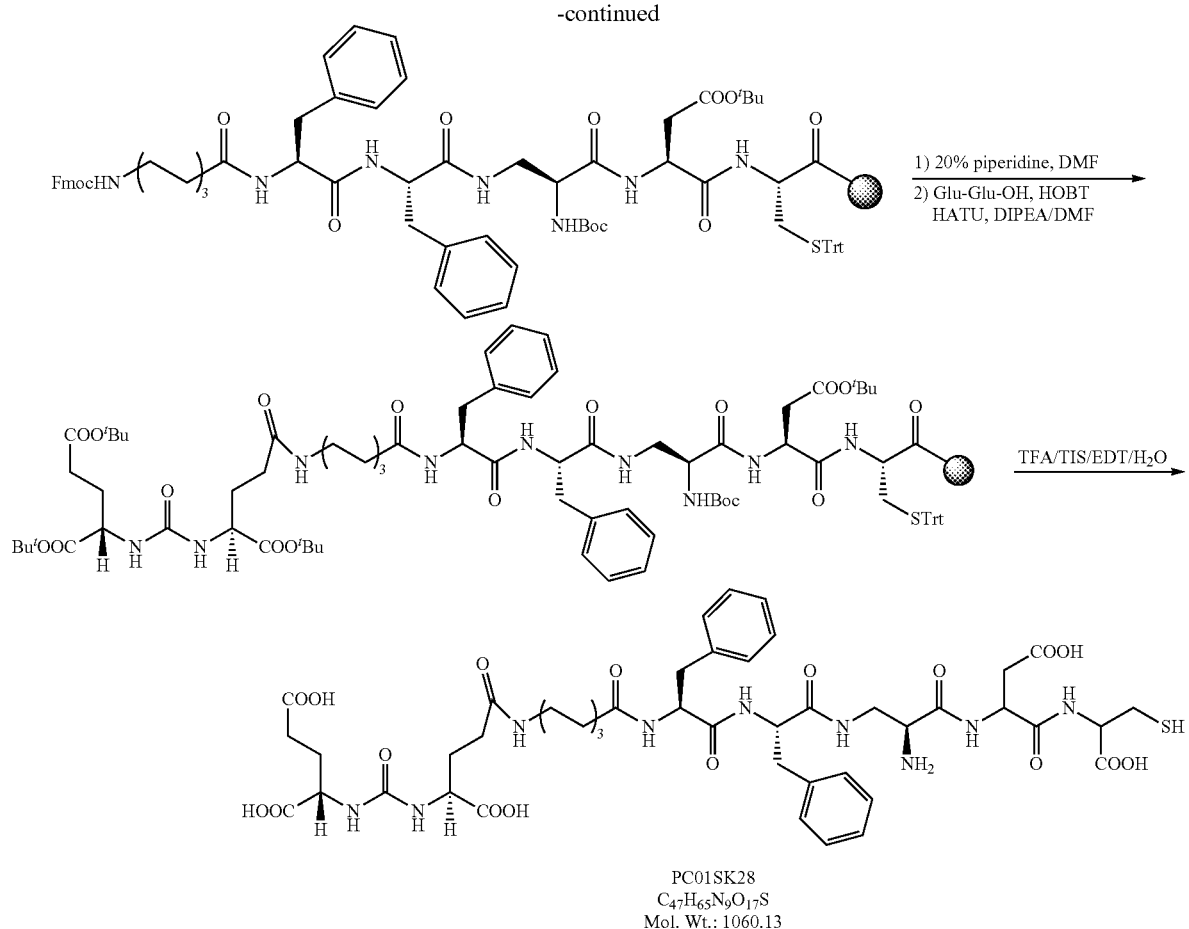

PC01SK28
$C_{47}H_{65}N_9O_{17}S$
Mol. Wt.: 1060.13

PC01SK28 was synthesized using standard Fmoc-SPPS starting from Fmoc-Cys(Trt)-Wang resin (Novabiochem; Catalog #04-12-2050); purified using reverse phase preparative HPLC (Waters, xTerra $C_{18}$ 10 µm; 19×250 mm) A=0.1 TFA, B=ACN; λ=257 nm; Solvent gradient: 5% B to 80% B in 25 min, 80% B wash 30 min run, (61%); and analyzed using reverse phase analytical HPLC (Waters, X-Bridge $C_{18}$ 5 µm; 3.0×15 mm); A=0.1 TFA, B=ACN; λ=257 nm, 5% B to 80% B in 10 min, 80% B wash 15 min run. PC01SK28L: $C_{47}H_{65}N_2O_{17}S$; MW=1060.13 g/mol; white solid; $R_t$=7.7 min; $^1$H NMR (DMSO-$d_6$/$D_2O$) δ 0.93 (m, 2H); 1.08 (m, 5H); 1.27 (m, 5H); 1.69 (m, 2H); 1.90 (m, 2H); 1.94 (m, 2H); 2.10 (m, 2H); 2.24 (q, 2H); 2.62 (m, 2H); 2.78 (m, 4H); 2.88 (dd, 1H); 2.96 (t, 2H); 3.01 (dd, 1H); 3.31 (dd, 1H); 3.62 (dd, 1H); 3.80 (q, 1H, αH); 4.07 (m, 1H, αH); 4.37 (m, 1H, αH); 4.42 (m, 2H, αH); 4.66 (m, 1H, αH); 7.18 (m, 10H, Ar—H): LC-MS=1061 (M+H)$_+$; ESI-MS=1061 (M+H)$^+$.

The foregoing exemplary embodiments are intended to be illustrative of the invention, and should not be interpreted or construed as limiting in any way the invention as described herein.

Example 19

Flourophore-Dependent Studies Using Fluorescent-Activated Cell Sorting (FACS)

LNCaP cells were seeded in T75 flasks and allowed to grow to adherent monolayers for 48 hours in RPMI with glutamine (2 mM, Gibco RPMI medium 1640, catalog #22400) plus 10% FBS (Fetal Bovine Serum), 1% sodium pyruvate (100 mM) and 1% PS (penicillin streptomycin) in a 5%-$CO_2$ atmosphere at 37° C. Cells were trypzinysed and an equal amount of cells (50,000 cells/tube) were transferred into 7 centrifuge tubes.

Figure 9A:
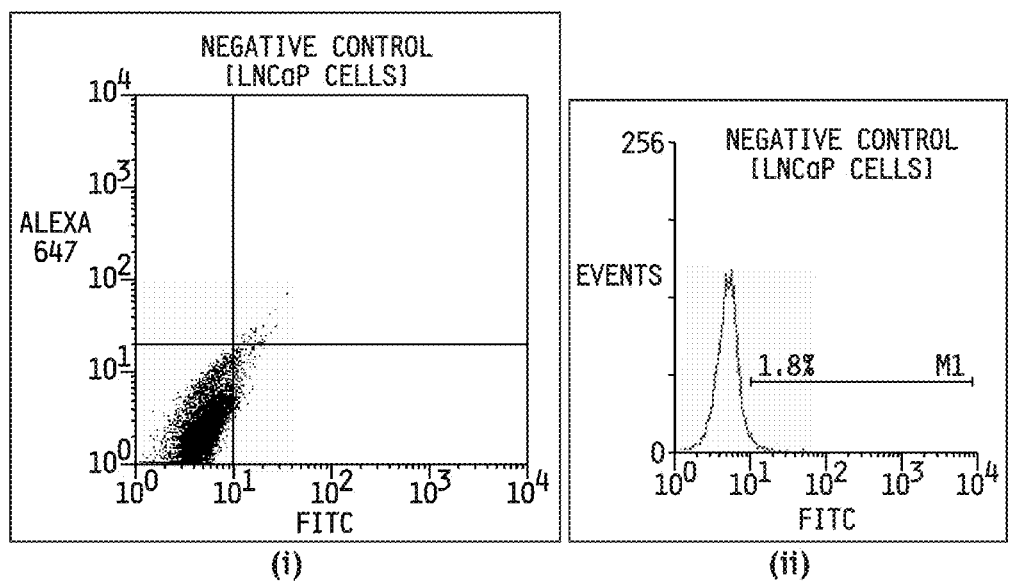
FIG. 9(a) shows a histogram (i) and dot plot (ii) of LNCaP cells alone (negative control).
Figure 9B:
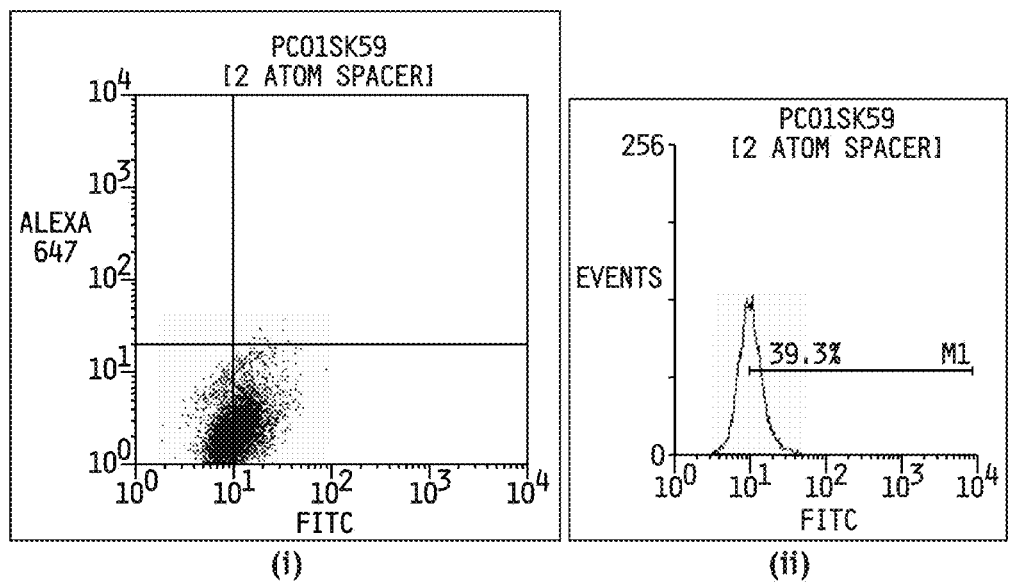
FIG. 9(b) shows a histogram (i) and dot plot (ii) of LNCaP cells incubated with PC01SK59.
Figure 10A:
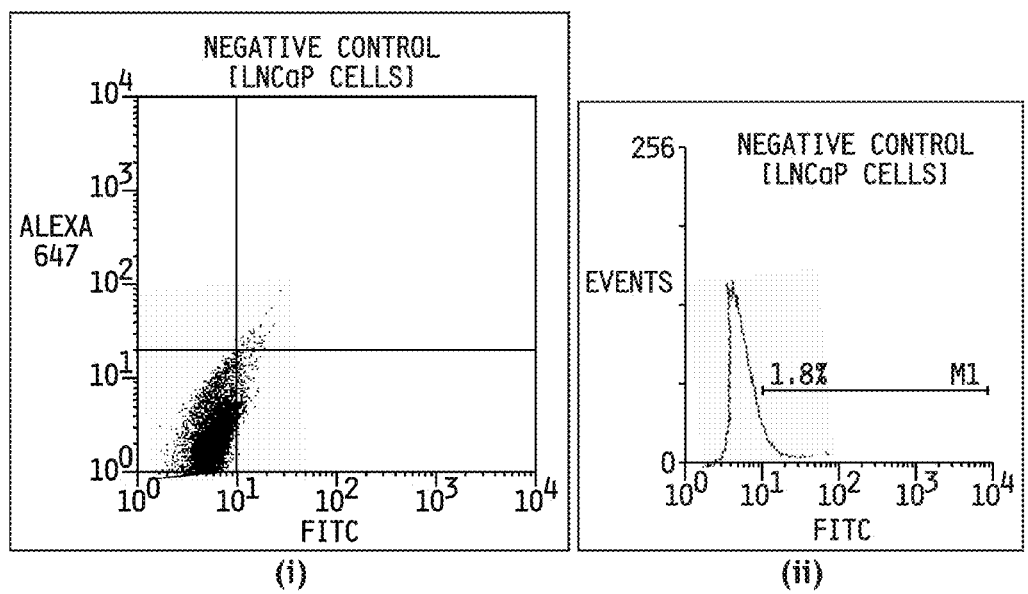
FIG. 10(a) shows a histogram (i) and dot plot (ii) of LNCaP cells alone (negative control).
Figure 10B:
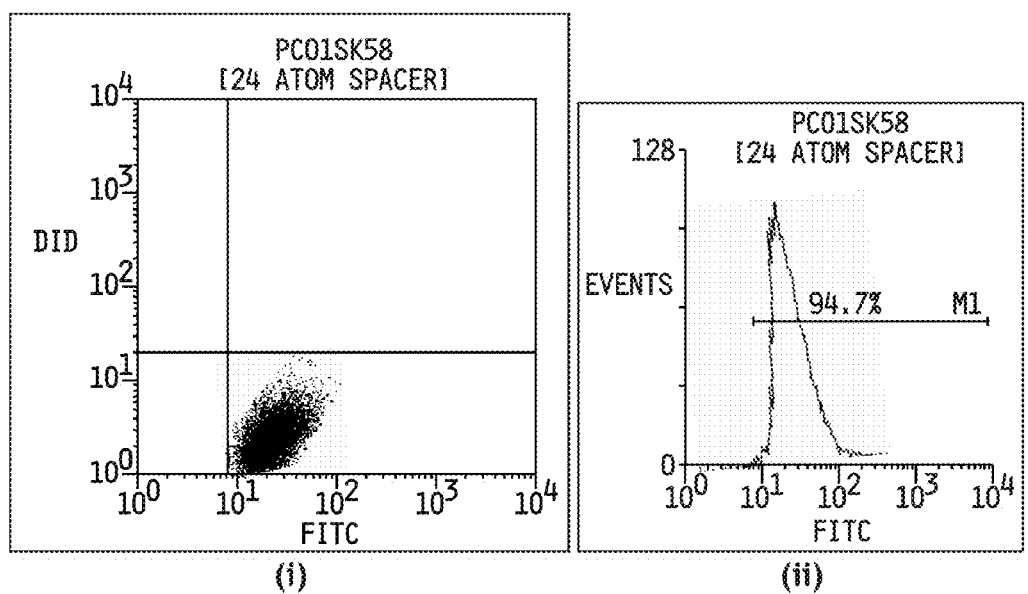
FIG. 10(b) shows a histogram (i) and dot plot (ii) of LNCaP cells incubated with PC01SK58.
Figure 11A:
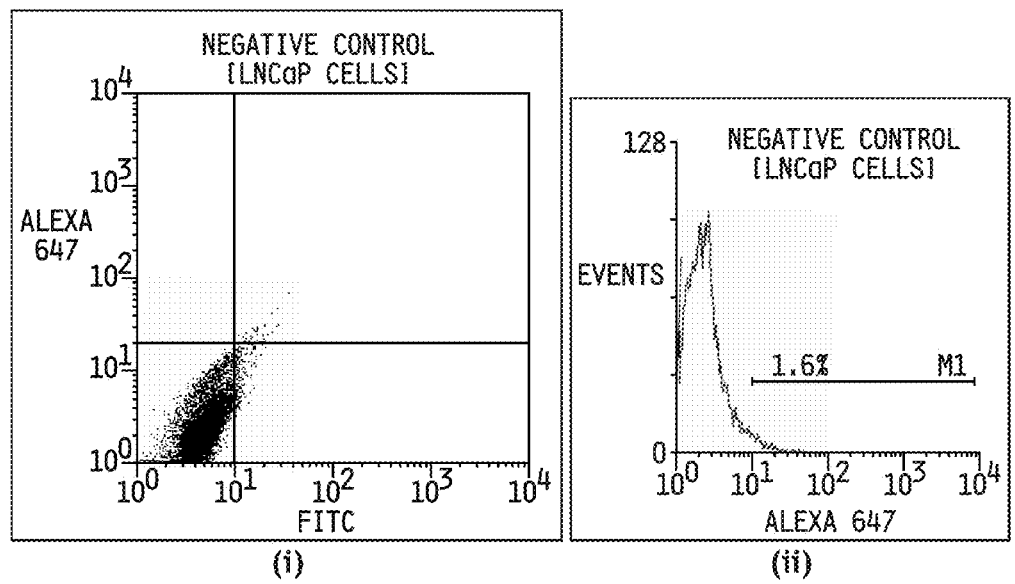
FIG. 11(a) shows a histogram (i) and dot plot (ii) of LNCaP cells alone (negative control).
Figure 11B:
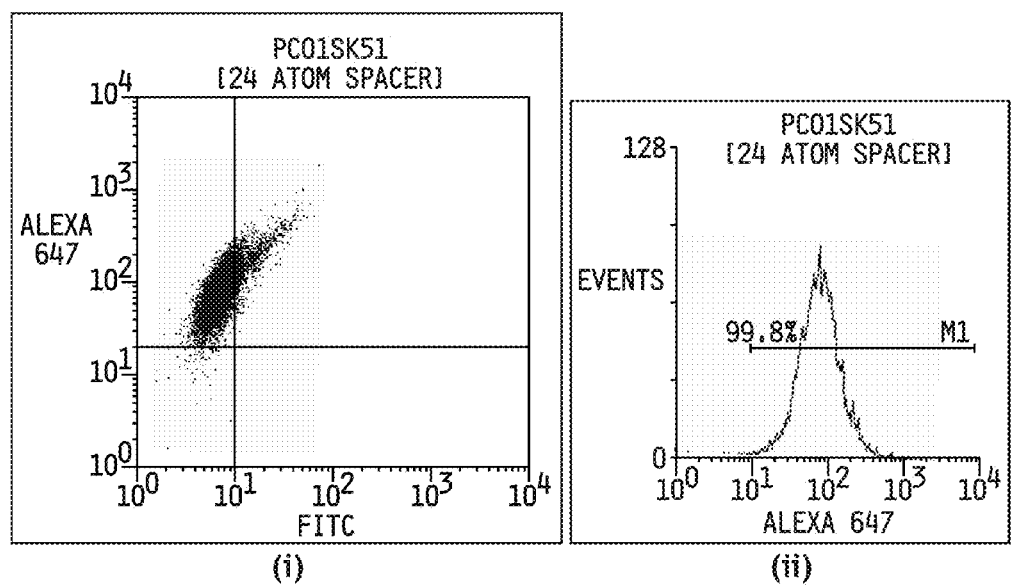
FIG. 11(b) shows a histogram (i) and dot plot (ii) of LNCaP cells incubated with PC01SK51.
Figure 12A:
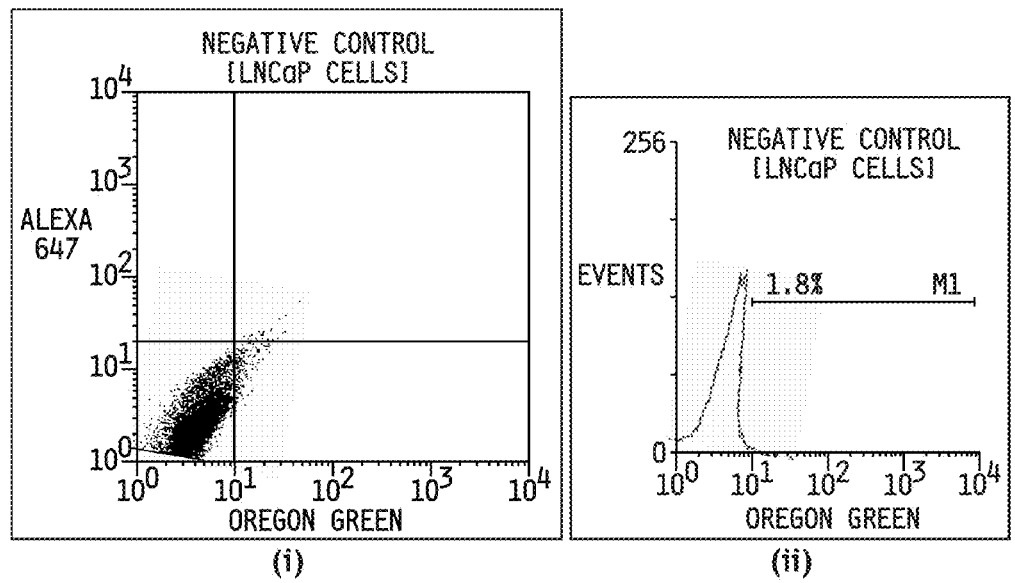
FIG. 12(a) shows a histogram (i) and dot plot (ii) of LNCaP cells alone (negative control).
Figure 12B:
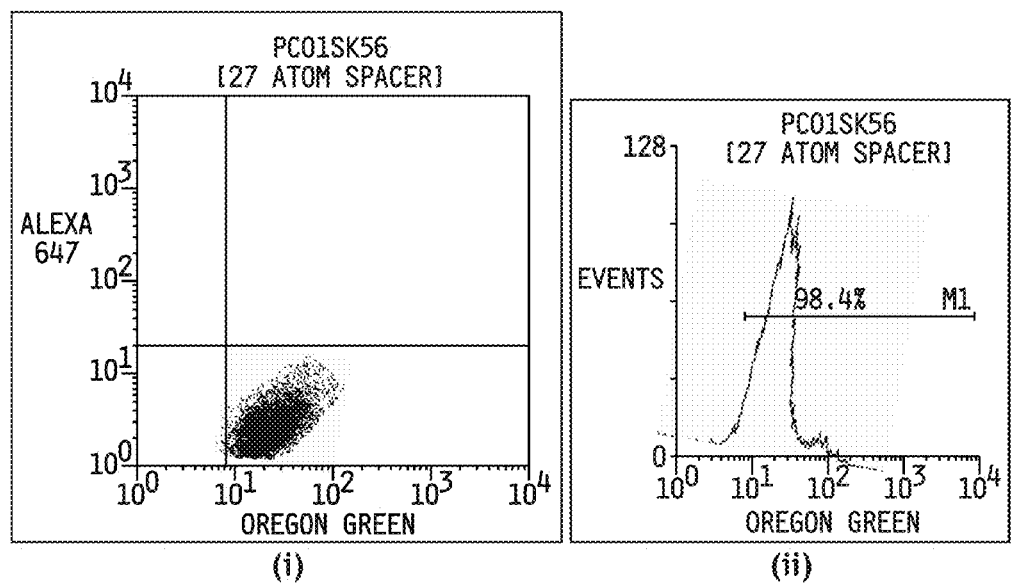
FIG. 12(b) shows a histogram (i) and dot plot (ii) of LNCaP cells incubated with PC01SK56.
Figure 13A:
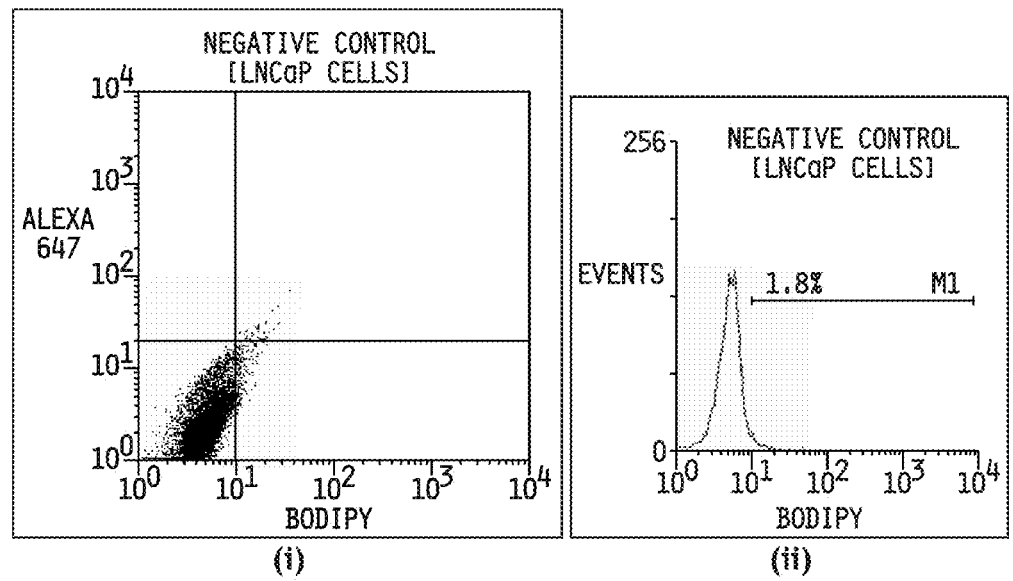
FIG. 13(a) shows a histogram (i) and dot plot (ii) of LNCaP cells alone (negative control).
Figure 13B:
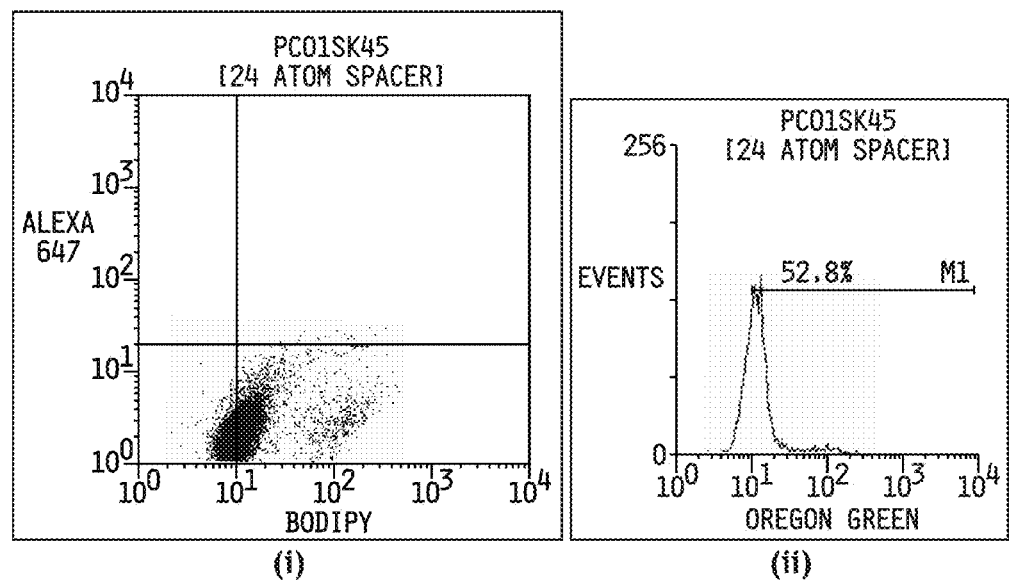
FIG. 13(b) shows a histogram (i) and dot plot (ii) of LNCaP cells incubated with PC01SK45.
Figure 14A:
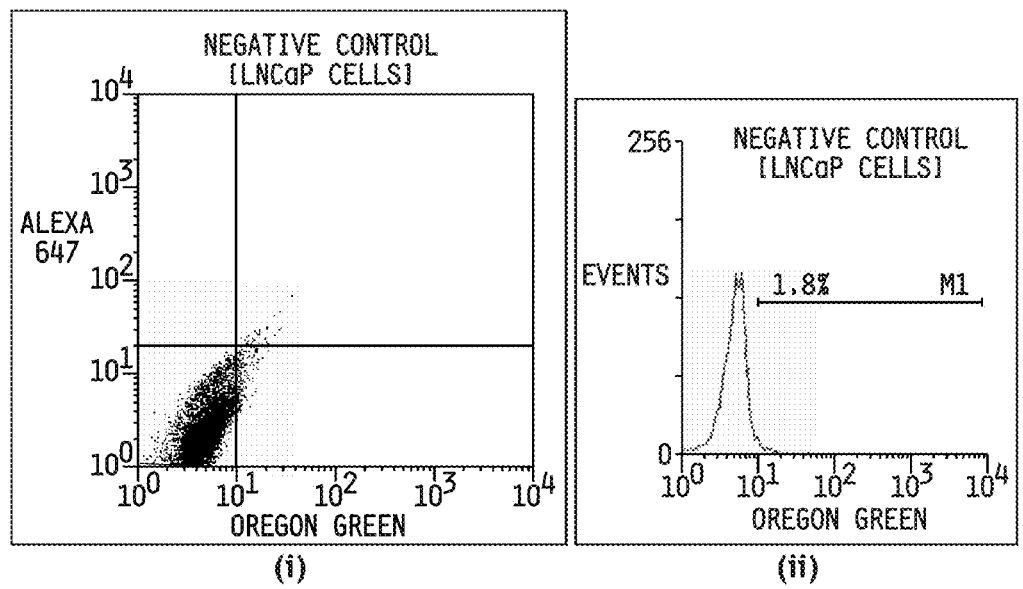
FIG. 14(a) shows a histogram (i) and dot plot (ii) of LNCaP cell alone (negative control).
Figure 14B:
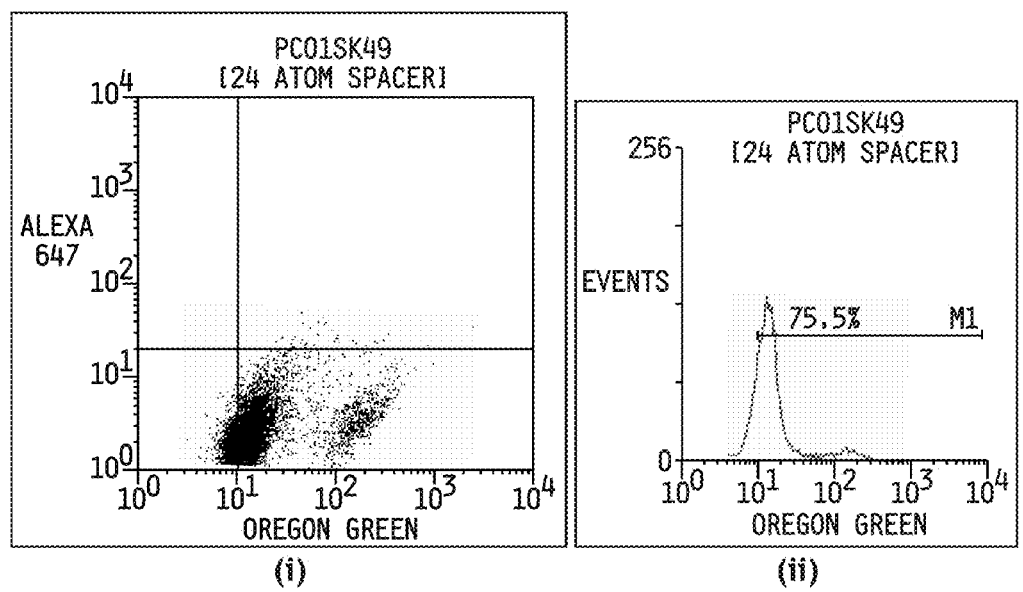
FIG. 14(b) shows a histogram (i) and dot plot (ii) of LNCaP cells incubated with PC01SK49.

| Tube number | Substrate |
|---|---|
| 1 | no substrate; 1.0 mL of medium => Negative control (FIG. 9a) |
| 2 | 1 uM of PC01SK59 in 1.0 mL of medium (FIG. 9b) |
| 3 | 1 uM of PC01SK58 in 1.0 mL of medium (FIG. 10b) |
| 4 | 1 uM of PC01SK51 in 1.0 mL of medium (FIG. 11b) |
| 5 | 1 uM of PC01SK56 in 1.0 mL of medium (FIG. 12b) |
| 6 | 1 uM of PC01SK45 in 1.0 mL of medium (FIG. 13b) |
| 7 | 1 uM of PC01SK49 in 1.0 mL of medium (FIG. 14b) |

Samples were incubated in a 5%-$CO_2$ atmosphere at 37° C. for 45 minutes. Cells were rinsed twice with 1.0 mL of RPMI medium and once with tris buffer. 1 mL of tris buffer was added to each tube and transferred to individual FACS vials. Data were acquired for each sample using a flow cytometer.

Example 20

Fluorescence-Labeling Studies Using Confocal Microscopy

Figure 15A:
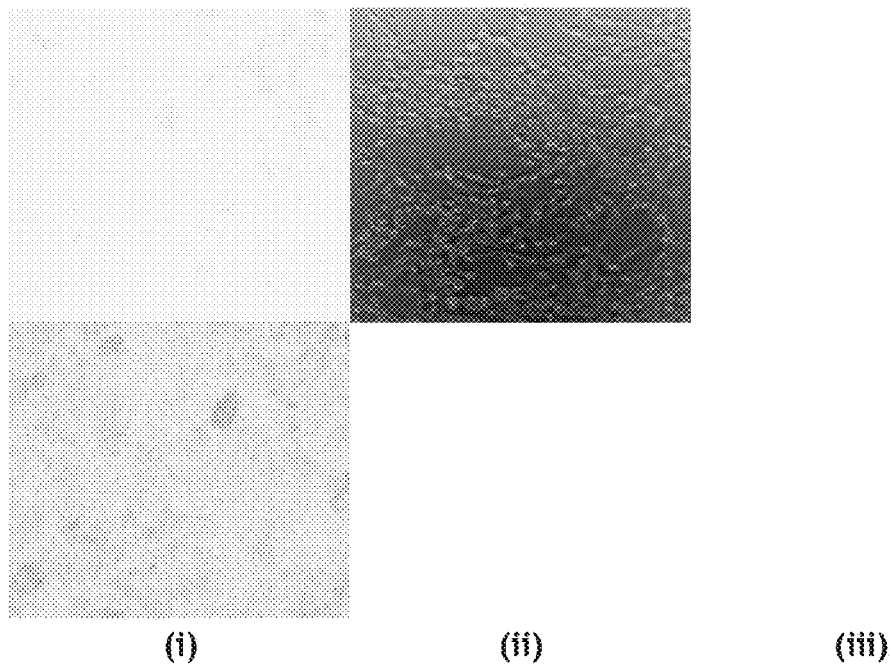
FIG. 15(a) shows FITC 488-labeling studies using confocal microscopy. Imaging of LNCaP cells incubated with PC01SK58 is shown by confocal microscopy (i) and phase contrast microscopy (ii). LNCaP cells incubated with PMPA then with PC01SK58 is shown by confocal microscopy (iii).
Figure 15B:
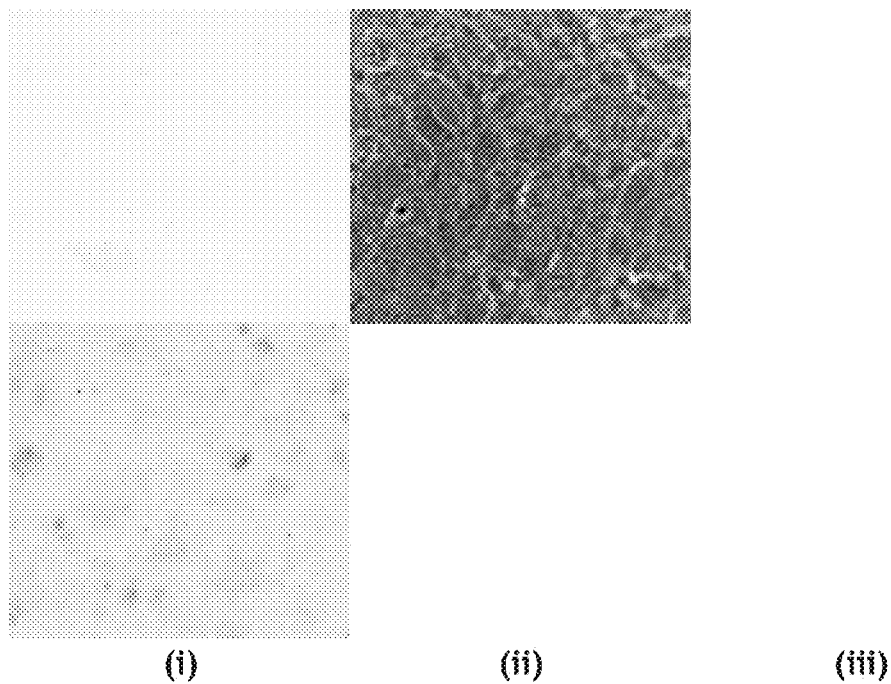
FIG. 15(b) shows OREGON GREEN 488-labeling studies using confocal microscopy. Imaging of LNCaP cells incubated with PC01SK49 is shown by confocal microscopy (i) and phase contrast microscopy (ii). LNCaP cells incubated with PMPA then with PC01SK49 is shown by confocal microscopy (iii).
Figure 15C:
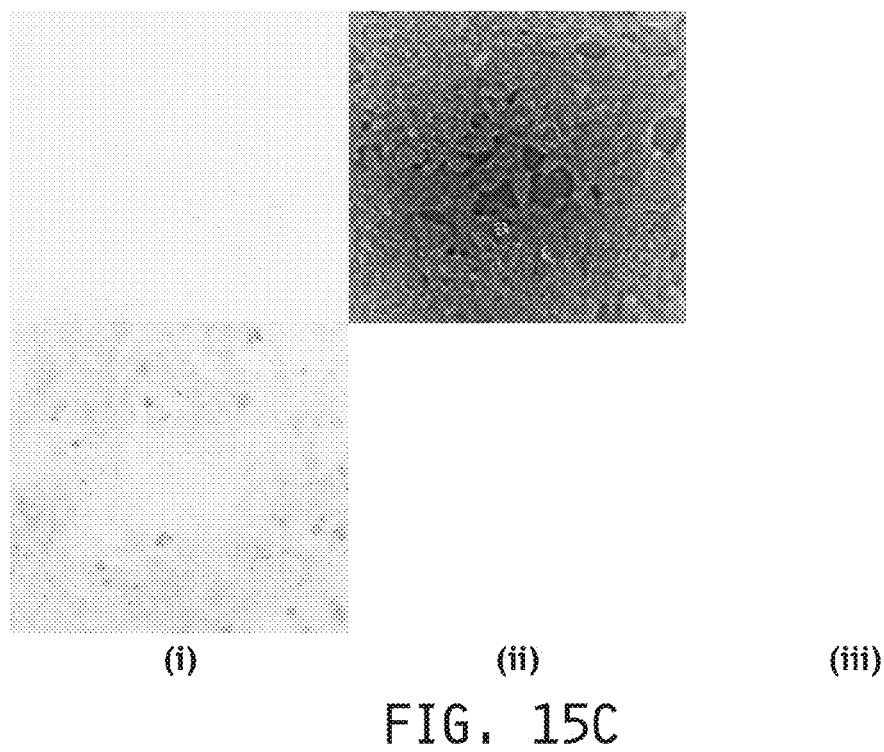
FIG. 15(c) shows ALEXAFLUOR 647 maleimide-labeling studies using confocal microscopy. Imaging of LNCaP cells incubated with PC01SK51 is shown by confocal microscopy (i) and microscopy (ii). LNCaP cells incubated with PMPA then with PC01SK51 is shown by confocal microscopy (iii).

LNCaP cells were seeded in 6-well falcon plates and allowed to grow to adherent monolayers for 48 hours in RPMI with glutamine (2 mM)(Gibco RPMI medium 1640, catalog #22400) plus 10% FBS (Fetal Bovine Serum), 1% sodium pyruvate (100 mM) and 1% PS (penicillin streptomycin) in a 5% $CO_2$ atmosphere at 37° C. Cells in 3 wells were incubated with PC01SK58 (1 uM; FIG. 15(a), (i)) or PC01SK49 (1 uM; FIG. 15(b), (i)) or PC01SK51 (1 uM; FIG. 15(c), (i)) in a 5% $CO_2$ atmosphere at 37° C. for 1 hour. Cells in the other three wells were incubated with PMPA (competition) in a 5% $CO_2$ atmosphere at 37° C. for 30 minutes and then with PC01SK58 (1 uM; FIG. 15(a), (iii)) or PC01SK49 (1 uM; FIG. 15(b), (iii)) or PC01SK51 (1 uM; FIG. 15(c), (iii)) in a 5% $CO_2$ atmosphere at 37° C. for 1 hour. Cells were rinsed three times with 1.0 mL of RPMI and then 2 mL of RPMI medium was added to each well. Confocal microscopy pictures were taken for each well to show fluorescence-labeling and competition (binding specificity of the ligand to PSMA).

Example 21

Blood Spiking Studies Using FACS

LNCaP cells were seeded in T75 flasks and allowed to grow to adherent monolayers for 48 hours in RPMI with glutamine (2 mM)(Gibco RPMI medium 1640, catalog #22400) plus 10% FBS (Fetal Bovine Serum), 1% sodium pyruvate (100 mM) and 1% PS (penicillin streptomycin) in a 5% $CO_2$ atmosphere at 37° C. Cells were trypsinized and $2 \times 10^6$ cells were transferred into a centrifuge tube. LNCaP cells were incubated with DID (1 uM) in a 5%-$CO_2$ atmosphere at 37° C. for 20 minutes. DID-labeled LNCaP cells were transferred into a healthy donor blood sample (4.0 mL) in a centrifuge tube. The RosetteSep procedure was followed for the DID-labeled LNCaP cells in blood (4.0 mL) and also blood samples (1.0 mL) that did not contain LNCaP cells in a separate centrifuge tube.

Briefly, blood samples, PBS+2% FBS, Ficoll Paque and centrifuge were kept at room temperature. RosetteSep Human Circulating Eptthelial Tumor Cell Enrichment Cocktail was added at 50 uL/mL of whole blood (e.g. 100 uL of cocktail was added to 2 mL of whole blood) and mixed well. Samples were incubated at room temperature for 20 minutes. Samples were diluted with an equal volume of PBS+2% FBS and mixed gently. The diluted samples were layered on top of the Ficoll-Paque (3 mL). Samples were centrifuged for 20 minutes at 1200×g at room temperature with the brake off. The enriched cells were removed from the Ficoll-Paque (plasma interface) and the plasma interface was removed from the blood sample that did not contain LNCaP cells. It is appreciated that the cells at the interface may be difficult to visualize in some instances, especially when very rare cells are enriched. In those cases some of the Ficoll-Paque may be removed along with the enriched cells in order to ensure their complete recovery.

Enriched cells were washed two times with PBS+2% FBS and once with ammonium chloride to remove red blood cells. An equal amount of enriched cells (DID-labeled LNCaP cells) were transferred to 4 centrifuge tubes (~50,000 cells/tube) that contained 1.0 mL of RPMI medium (tube number 2-5) and an equal volume of plasma interface was transferred to another centrifuge tube (tube number 1) from the blood sample that did not contain LNCaP cells to 1.0 mL of RPMI medium.

Figure 16A:
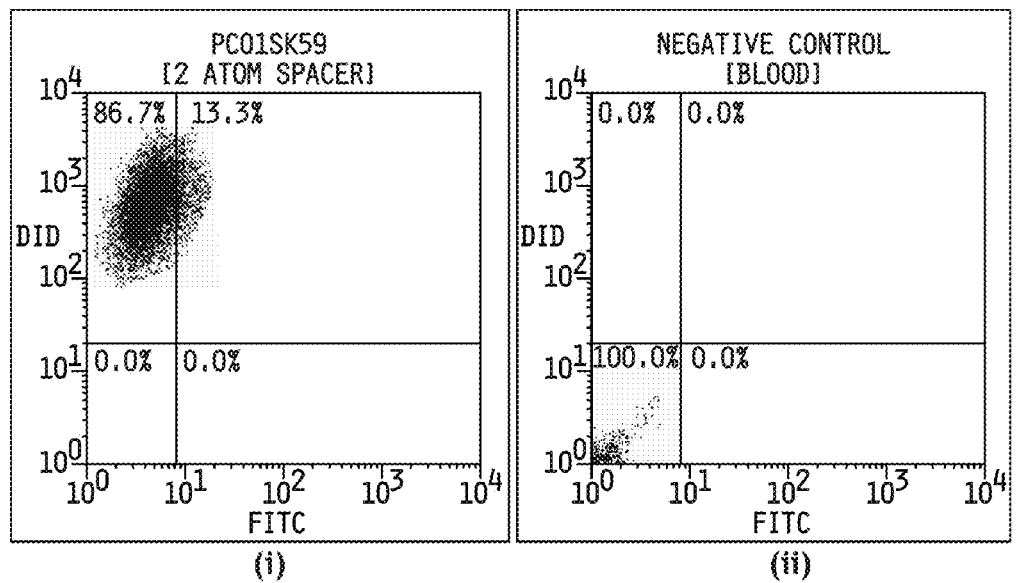
FIG. 16(a) shows a 2 Atom Spacer: (i) shows a dot plot diagram of a blood sample labeled with PC01SK64 (negative control) and (ii) shows a dot plot diagram of LNCaP cells first labeled with DID then with PC01SK63.
Figure 16B:
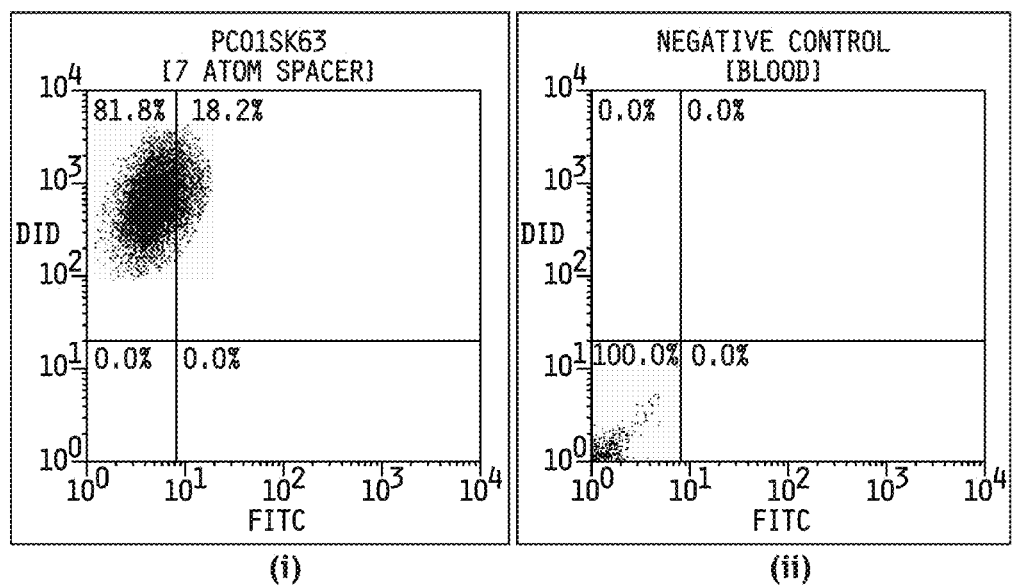
FIG. 16(b) shows a 7 Atom Spacer: (i) shows a dot plot diagram of a blood sample labeled with PC01SK64 (negative control) and (ii) shows a dot plot diagram of LNCaP cells first labeled with DID then with PC01SK63.
Figure 16C:
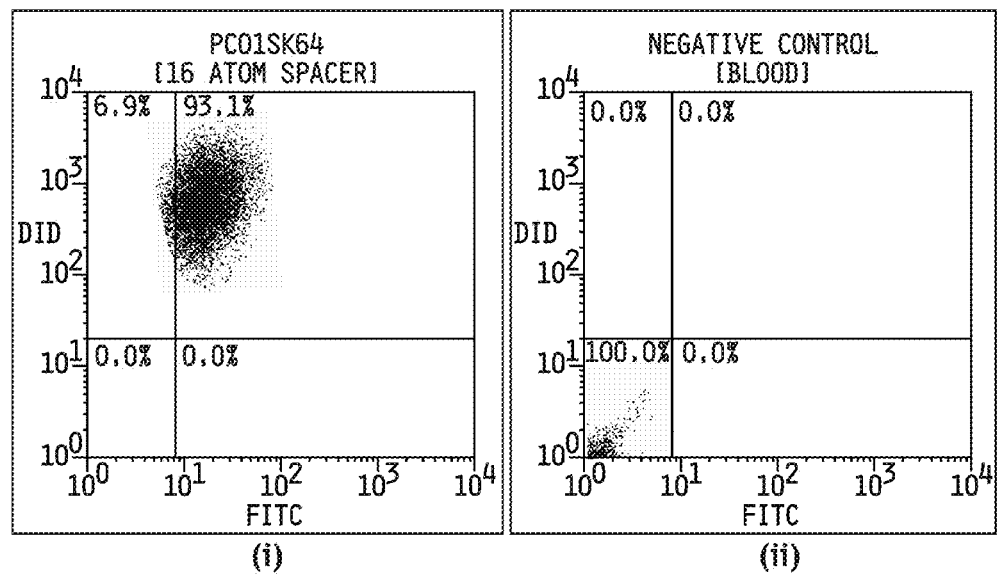
FIG. 16(c) shows a 16 Atom Spacer: (i) shows a dot plot diagram of a blood sample labeled with PC01SK64 (negative control) and (ii) shows a dot plot diagram of LNCaP cells first labeled with DID then with PC01SK64.
Figure 16D:
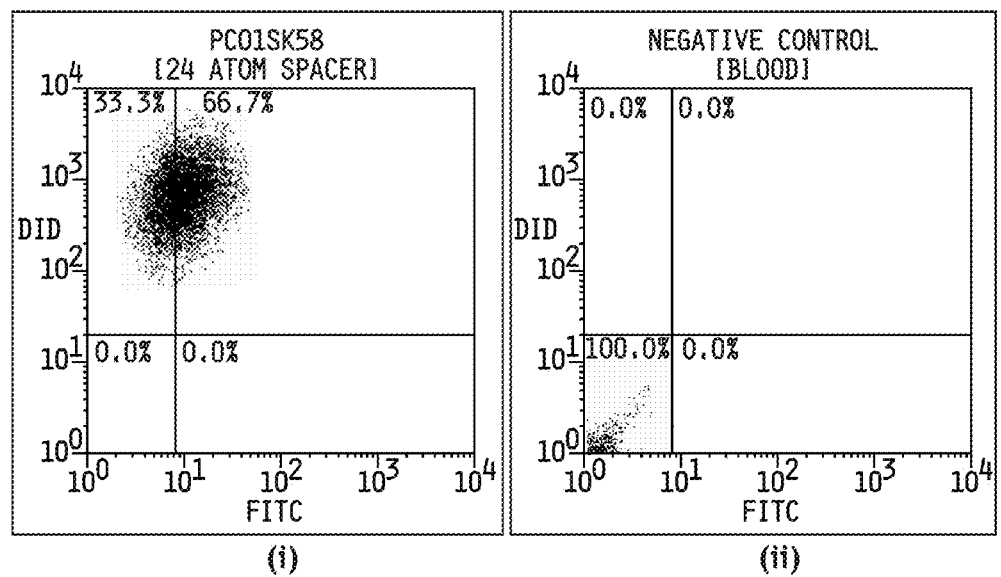
FIG. 16(d) shows a 24 Atom Spacer: (i) shows a dot plot diagram of a blood sample labeled with PC01SK64 (negative control) and (ii) shows a dot plot diagram of LNCaP cells first labeled with DID then with PC01SK58.

| Sample number (tube #) | Substrate added |
|---|---|
| 1 (plasma interface) | 1 uM of PC01SK64 => FIG. 16(a)(i) |
| 2 (DID labeled LNCaP cells in plasma interface) | 1 uM of PC01SK59 => FIG. 16(a)(ii) |
| 3 (DID labeled LNCaP cells in plasma interface) | 1 uM of PC01SK63 => FIG. 16(b)(ii) |
| 4 (DID labeled LNCaP cells in plasma interface) | 1 uM of PC01SK64 => FIG. 16(c)(ii) |
| 5 (DID labeled LNCaP cells in plasma interface) | 1 uM of PC01SK58 => FIG. 16(d)(ii) |

100 uL of substrate (from 10 uM stock solution) was added to each centrifuge tube as indicated above and the samples were incubated in a 5% $CO_2$ atmosphere at 37° C. for 45 minutes. Samples were washed with RPMI medium two times, once with tris buffer and flow cytometric analysis was carried out.

Figure 17:
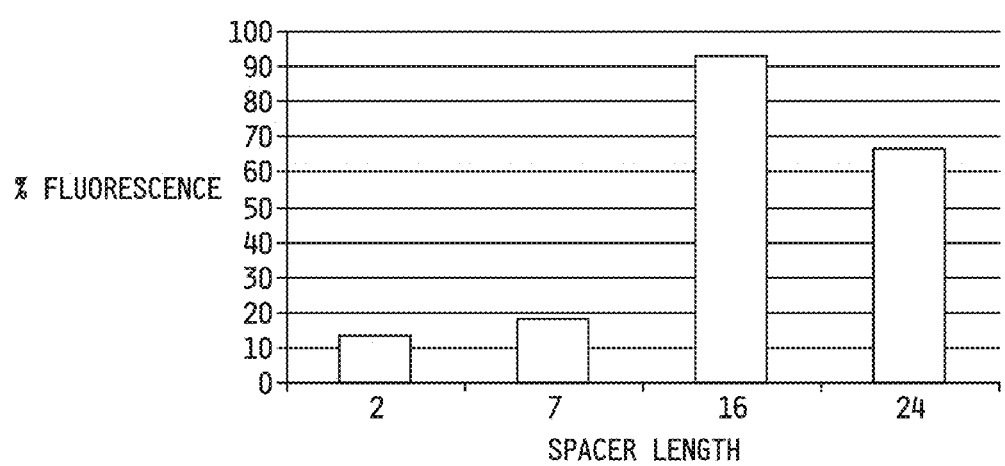
FIG. 17 shows a summary of blood spiking studies using FACS: plot of fluorescence versus spacer length (atoms).

The dot plot of % DID-labeled versus % FITC-labeled were used to determine the binding affinity of each compound to PSMA. From the plot of % fluorescence versus spacer length (FIG. 17), PC01SK64 had the best binding affinity for PSMA of the four compounds.

Example 22

Figure 18A:
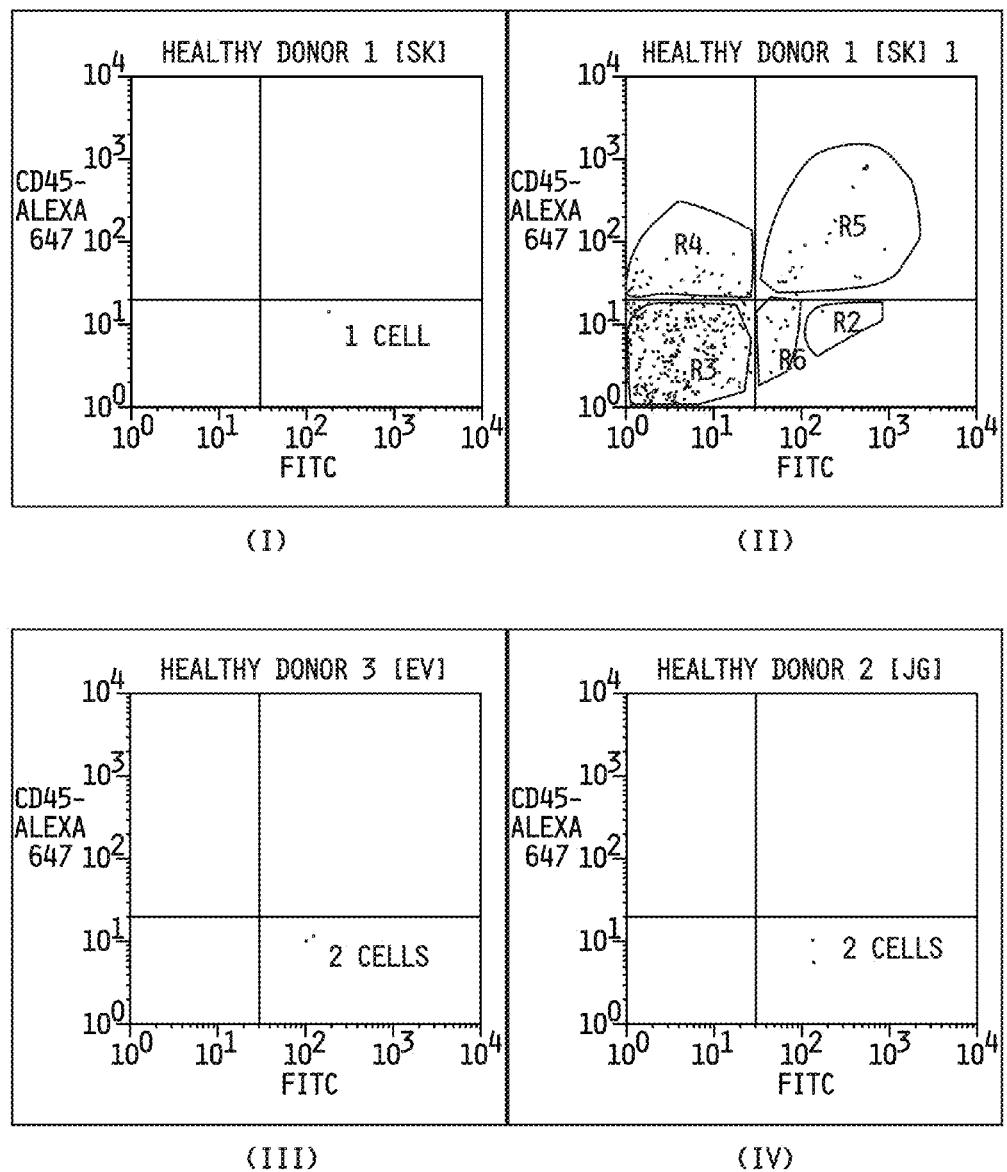
FIG. 18(a) shows a dot plot of healthy donor blood samples labeled with CD45-ALEXAFLUOR then incubated with PC01SK64 (16 atom spacer). Panel (I) shows cells in all regions for male healthy donor 1 (SK), panel (II) shows cells in region 2 for male healthy donor 1 (SK), panel (III), shows cells in region 2 for female donor 3 (EV), and panel (IV) shows cells in region 2 for male healthy donor 2 (JG).

Detection of Circulating Tumor Cells (CTC) in Prostate Cancer Patient Blood Samples Using Facs Analysis Samples:

1) Blood samples of five healthy donors (6.0-8.0 mL/donor). Data is shown for 3 donors (FIG. 18(a)).

Figure 18B:
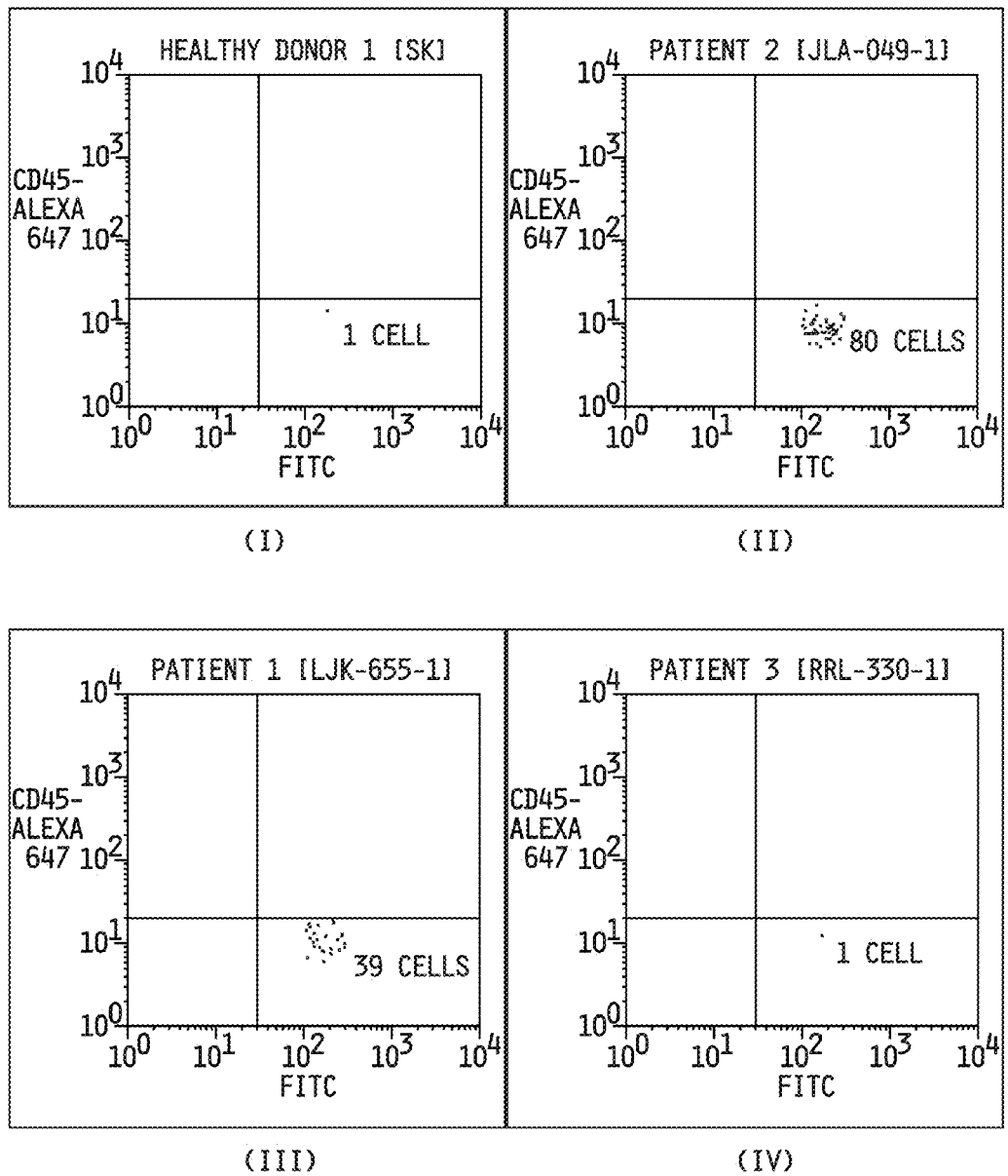
FIG. 18(b) shows a dot plot of prostate cancer patient blood samples labeled with CD45-ALEXAFLUOR then incubated with PC01SK64 (16 atom spacer). Panel (I) shows cells in region 2 for male healthy donor 1 (SK), panel (II) shows cells in region 2 for patient 1 (JLA-049-1), panel (III) shows cells in region 2 for patient 2 (LJK-665-1), and panel (IV) shows cells in region 2 for patient 3 (RRL-330-1).
Figure 19:
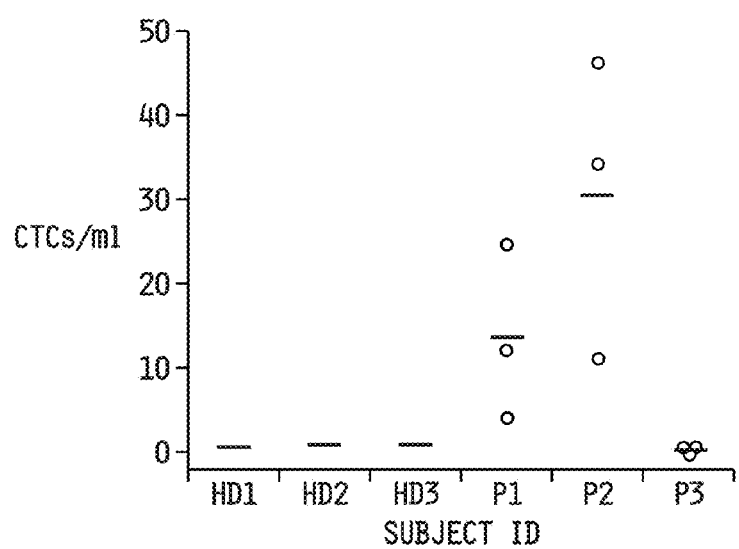
FIG. 19 shows a summary of CTC studies: plot of circulating tumor cells/mL versus subject ID.

2) Blood samples of five prostate cancer patients (6.0-8.0 mL/donor) received from Mayo clinic (Rochester, Minn.). Data is shown for 3 patients (FIG. 18(b), (II), (III) and (IV)).

Each blood sample was split into three centrifuge tubes (2.0 mL/tube) and the RosetteSep procedure was carried out separately for each sample. Briefly, the blood samples, PBS+2% FBS, Ficoll Paque and centrifuge were kept at room temperature. RosetteSep Human Circulating Eptthelial Tumor Cell Enrichment Cocktail was added at 50 uL/mL of whole blood (e.g. 100 uL of cocktail was added to 2 mL of whole blood) and mixed well. Samples were incubated at room temperature for 20 minutes. Samples were diluted with an equal volume of PBS+2% FBS and mixed gently. The diluted samples were layered on top of the Ficoll-Paque (3 mL). Samples were centrifuged for 20 minutes at 1200×g at room temperature with the brake off. The plasma interface was removed from the Ficoll-Paque from each sample.

The plasma interface was washed twice with PBS+2% FBS and once with ammonium chloride to remove red blood cells. 1 mL of medium was added to each centrifuge tube and 200 uL of CD45-ALEXAFLUOR 647 (1 uM, antibody) was added to each sample. 100 uL of PC01SK64 (from 10 uM stock solution) was added to each sample and incubated in a 5%-$CO_2$ atmosphere at 37° C. for 45 minutes. Cells were washed twice with RPMI medium and once with tris buffer before FACS analysis was performed.

The dot plot of CD45-ALEXAFLUOR 647-labeled cells verses FITC-labeled cells was used to calculate the number of PC01SK58 (24-atom spacer, C49H62N6O20S, Mol. Wt.: 1087.11) was prepared using universal PSMA resin and standard Fmoc SPPS conjugated with Fmoc-(PEG)$_6$-OH and purified by HPLC 1% B to 60% B in 25 min, 80% B wash 40 min run, (65%); analyzed using reverse phase analytical HPLC (Waters, X-Bridge C$_{18}$ 5 µm; 3.0×150 mm); A=10 mM NH$_4$OAc, B=ACN; λ=488 nm, 1% B to 60% B in 10 min, 80% B wash 15 min run; C$_{49}$H$_{60}$N$_6$O$_{20}$S; MW=1087.11 g/mol; orange color solid, R$_t$=7.3 min; ESI-MS=1087 (M+H)$^+$; 1109 (M+Na)+; 1085 (M−H)$^-$.

Example G

General synthesis of Cys-maleimide PSMA imaging agent conjugates illustrated for PC01SK56 using Wang PSMA (DUPA) resin, a 24-atom spacer, and OREGON GREEN 488, where n=3. CTCs in a blood sample (FIG. 18(*a*), (I); Region 2 or gate 2). Due to the size and granularity of the cancer calls, they appear on the R2 region (gate). The graph of CTCs versus subject ID was used to determine the number of circulating tumor cell in the blood of the prostate cancer patients.

Example 23

Synthesis of Folate-Cysteine

Standard Fmoc peptide chemistry was used to synthesize folate-cysteine with the cysteine attached to the γ-COOH of folic acid. The sequence Cys-Glu-Pteroic acid (Folate-Cys) was constructed by Fmoc chemistry with HBTU and N-hydroxybenzotriazole as the activating agents along with diisopropyethylamine as the base and 20% piperidine in dimethylformamide (DMF) for deprotection of the Fmoc groups. An α-t-Boc-protected N-α-Fmoc-L-glutamic acid was linked to a trityl-protected Cys linked to a 2-Chlorotrityl resin. N10-trifluoroacetylpteroic acid was then attached to the γ-COOH of Glu. The Folate-Cys was cleaved from the resin using a 92.5% trifluoroacetic acid-2.5% water-2.5% triisopropylsilane-2.5% ethanedithio solution. Diethyl ether was used to precipitate the product, and the precipitant was collected by centrifugation. The product was washed twice with diethyl ether and dried under vacuum overnight. To remove the N10-trifluoracetyl protecting group, the product was dissolved in a 10% ammonium hydroxide solution and stirred for 30 min at room temperature. The solution was kept under a stream of nitrogen the entire time in order to prevent the cysteine from forming disulfides. After 30 minutes, hydrochloric acid was added to the solution until the compound precipitated. The product was collected by centrifugation and lyophilized. The product was analyzed and confirmed by mass spectroscopic analysis (MW 544, M+545).

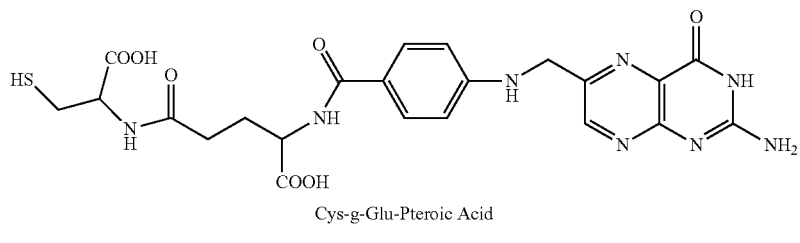

Cys-g-Glu-Pteroic Acid

MW 544.54

Example 24

Synthesis of Folate-Cys-Alexafluor 488

ALEXAFLUOR 488 C5-maleimide (Molecular Probes, Eugene, Oreg.) was dissolved in dimethyl sulfoxide (DMSO) (0.5 mg in 50 µl DMSO). A 1.5 molar equivalent (0.57 mg) of Folate-Cys was added to the solution and mixed for 4 hours at room temperature. Folate-Cys-ALEXAFLUOR 488 (Folate-ALEXAFLUOR) was purified by reverse-phase HPLC on a C18 column at a flow rate of 1 ml/min. The mobile phase, consisting of 10 mM NH4HCO3 buffer, pH 7.0 (eluent A) and acetonitrile (eluent B), was maintained at a 99:1 A:B ratio for the first minute and then changed to 1:99 A:B in a linear gradient over the next 29 minutes. Folate-Cys-ALEXAFLUOR 488 eluted at 20 minutes. The product was confirmed by mass spectroscopy and the biologic activity was confirmed by fluorescence measurement of its binding to cell surface folate receptors on folate receptor positive M109 cells in culture.

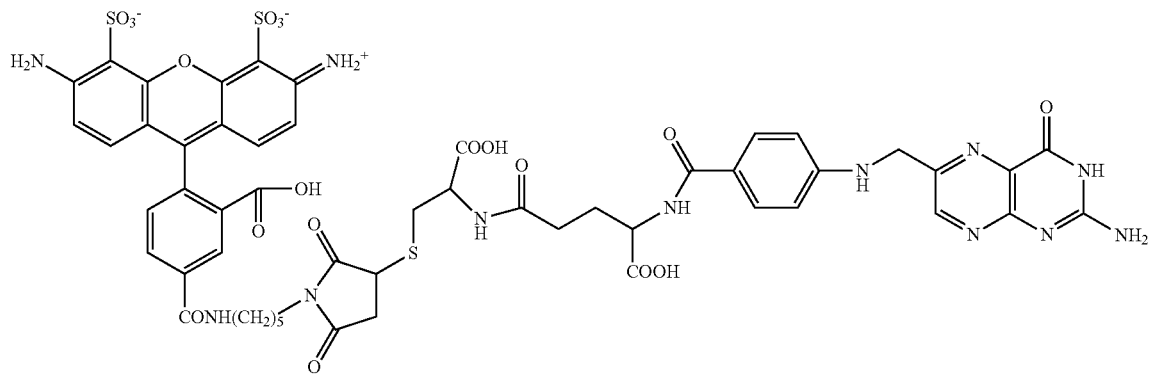

Alexa Fluor 488 - Cys-γ-Glu-Pteroic Acid

MW 1242.21

Example 25

Solid Phase Synthesis of Folate Conjugates

The precursor of folate, $N^{10}$-TFA-Pteroic acid was synthesized according to standard procedures. Fmoc-Lys(Mtt)-Wang resin was soaked in DMF for 20 minutes with nitrogen bubbling before the reaction. 20% piperidine was added to cleave the Fmoc protective group. 2.5 e.q. Fmoc-Glu-OtBu, HOBT and HBTU, dissolved in DMF, as well as 4 e.q. DIPEA were added to the reaction funnel. After 2 hours of nitrogen bubbling at room temperature, the Fmoc cleavage step was repeated with 20% piperidine. 1.5 e.q. $N^{10}$-TFA-Pteroic acid and 2.5 e.q. HOBT and HBTU, dissolved in 1:1 DMF/DMSO (dimethylformamide/dimethylsulfoxide), as well as 4 e.q. DIPEA were then added to the reaction for 4 hours with bubbling with nitrogen. The product was then washed with DMF, DCM (dichloromethane), methanol and isopropyl alcohol thoroughly and dried under nitrogen. 1% TFA/DCM (trifluoroacetic acid/dichloromethane) was used to cleave the Mtt (Mtt=4-methyltrityl) group. 2.5 e.q. Rd-ITC, dissolved in DMF, and 4 e.q. DIPEA were added to the resin and reaction was carried out at room temperature overnight under reduced light conditions. Cleavage of the conjugates was achieved by TFA:TIPS:$H_2O$ (95:2.5:2.5). The crude product was collected by precipitation with cool ether. The crude product was lyophilized overnight. On the second day, the crude product was hydrolyzed using 10% ammonium hydroxide (pH=10) for 45 minutes with nitrogen bubbling. The product was collected by lyophilization. Purification was carried out using preparative HPLC (Rigel).

Example 26

Synthesis of Folate Oregon Green 488

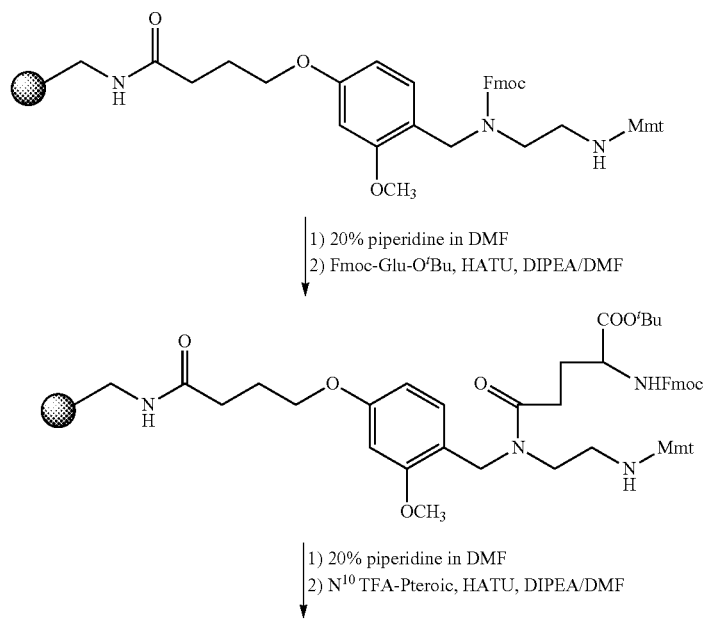

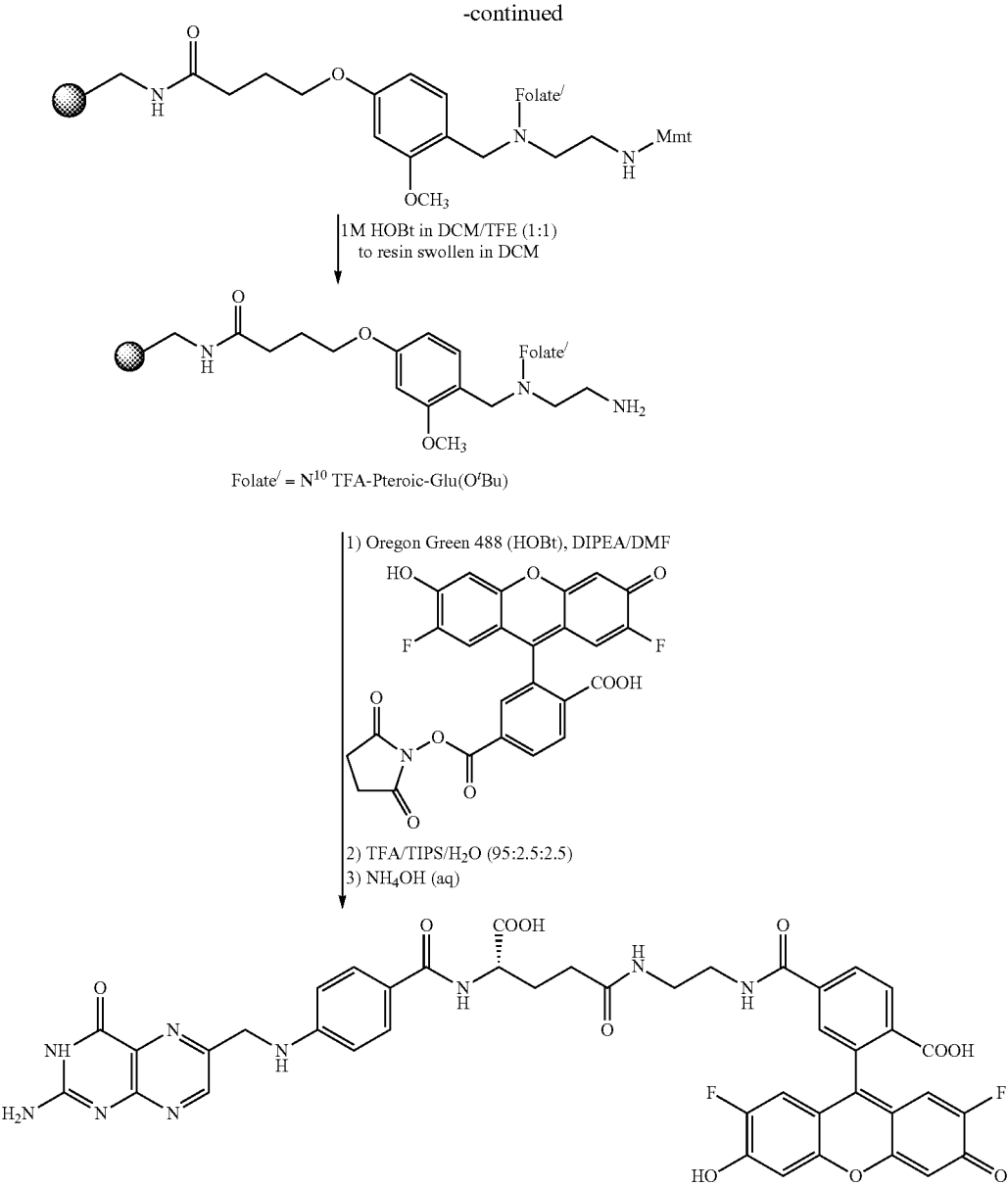

$N^{10}$ TFA-Pteroic acid was synthesized as follows. A universal folate resin was synthesized using Universal NovaTag™ resin (Novabiochem; Catalog #04-12-3910). After swelling the resin in DCM (Dichloromethane) for one hour and then with DMF (N,N-Dimethylformamide) for thirty minutes, deprotection of the Fmoc (Fluorenlmethyloxycarbonyl) protecting group was achieved by using a solution of 20% piperidine in DMF. Then Fmoc-Glu-OtBu (three-fold molar excess) was coupled to the deprotected secondary amine using HATU [2-(1H-7-Azabenzotriazol-1-yl)-1,1,3,3-tetramethyl uronium hexafluorophosphate] (three-fold molar excess) and DIPEA (N,N-Diisopropylethylamine) (ten-fold molar excess) in DMF. After thorough washing of this resin, the Fmoc on Glu was removed as described above and $N^{10}$-TFA Pteroic acid was coupled using standard Fmoc solid phase peptide synthesis (SPPS) procedures. Next, the pendant Mmt (4-Methoxytrityl) was removed with 1M HOBT (1-Hyroxybenzotriazole) in DCM/TFE (Trifluoroethanol).

At this point the resin can be washed with DMF and used immediately for further synthesis or washed sequentially with DCM, DMF and MeOH (Methanol), and dried for later use. To the deprotected, amine reactive universal folate resin, a 1.5-fold molar excess of OREGON GREEN 488 carboxylic acid succinimidyl ester 6 isomer (O-6149) and a 3-fold molar excess of DIPEA was allowed to react for 12 h at room temperature. The resin was next exhaustively rinsed with DMF, DCM, and methanol and dried for 2 hours. The Folate-OREGON GREEN 488 was then cleaved from the resin with a 95% trifluoroacetic acid-2.5% water-2.5% triisopropylsilane solution. Diethyl ether was used to precipitate the product, and the precipitant was collected by centrifugation. The product was washed twice with diethyl ether and dried under vacuum overnight. To remove the $N^{10}$-trifluoracetyl protecting group, the product was dissolved in a 10% ammonium hydroxide solution and stirred for 30 min at room temperature. The product was precipitated with combined isopropanol and ether, and the precipitant was collected by centrifugation. The product was purified by reverse-phase HPLC on a C18 column at a flow rate of 1 ml/min. The mobile phase, consisting of 10 mM NH$_4$HCO$_3$ buffer, pH 7.0 (eluent A) and acetonitrile (eluent B), was maintained at a 99:1 A:B ratio for the first minute and then changed to 1:99 A:B in a linear gradient over the next 29 minutes. The product was confirmed by MS and NMR.

Example 27

Synthesis of Folate Dylight 680

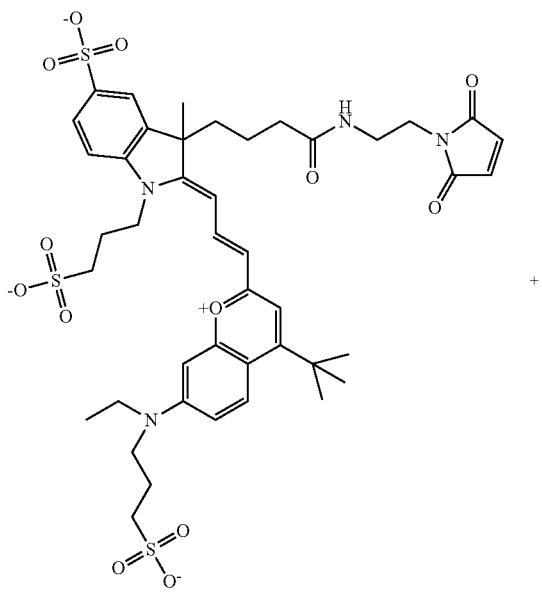

DyLight 680 maleimide

+

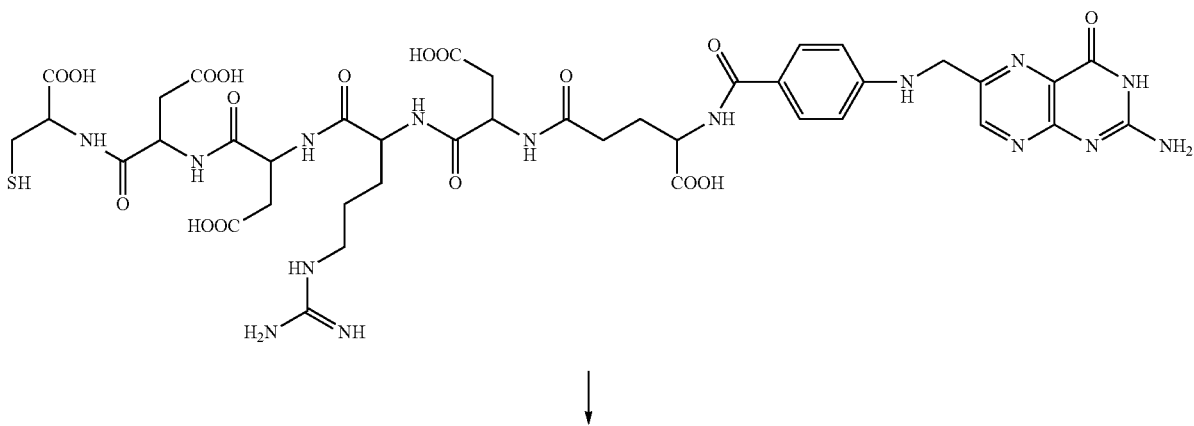

↓

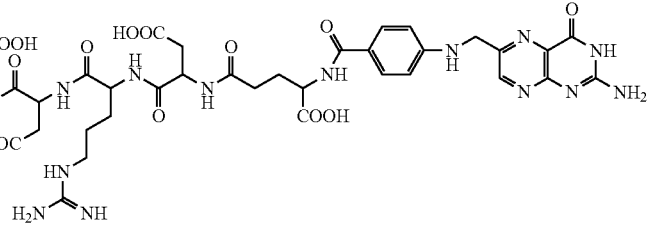
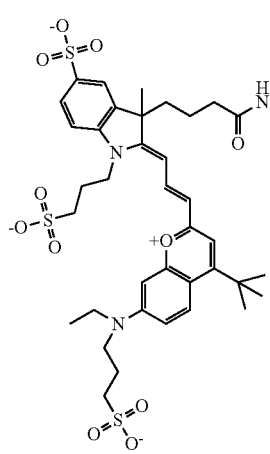

Folate DyLight 680

DYLIGHT 680 Maleimide (Pierce) was dissolved in dimethyl sulfoxide (DMSO) (1 mg in 100 uL DMSO). A 3-fold molar excess of Folate-Asp-Arg-Asp-Asp-Cys (synthesized as previously described: *Bioorganic & Medicinal Chemistry Letters*, Volume 16, Issue 20, 15 Oct. 2006, Pages 5350-5355) was added to the solution and mixed for 4 hours at room temperature. Folate-DYLIGHT 680 was purified by reverse-phase HPLC on a C18 column at a flow rate of 1 ml/min. The mobile phase, consisting of 10 mM NH$_4$HCO$_3$ buffer, pH 7.0 (eluent A) and acetonitrile (eluent B), was maintained at a 99:1 A:B ratio for the first minute and then changed to 1:99 A:B in a linear gradient over the next 29 minutes. The product was confirmed by MS and NMR (($C_{83}H_{103}N_{19}O_{30}S_4)^{2-}$; exact Mass: 1973.60; molecular weight: 1975.08; C, 50.47; H, 5.26; N, 13.47; O, 24.30; S, 6.49).

Example 28

Synthesis of Rhodamine Peg Conjugates

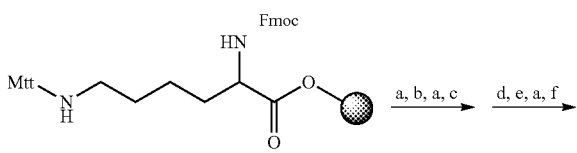

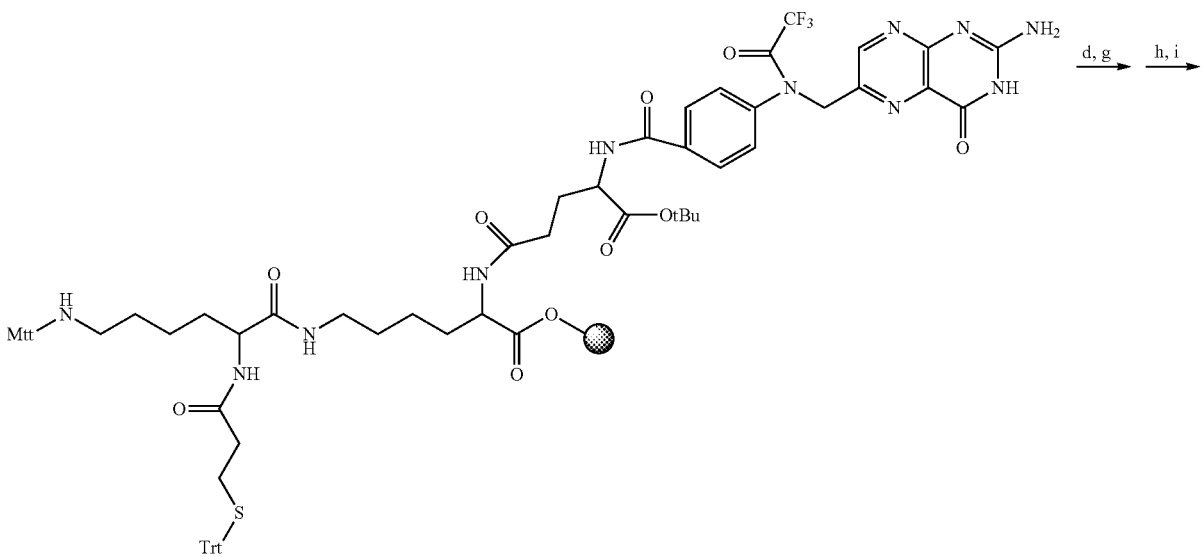

-continued

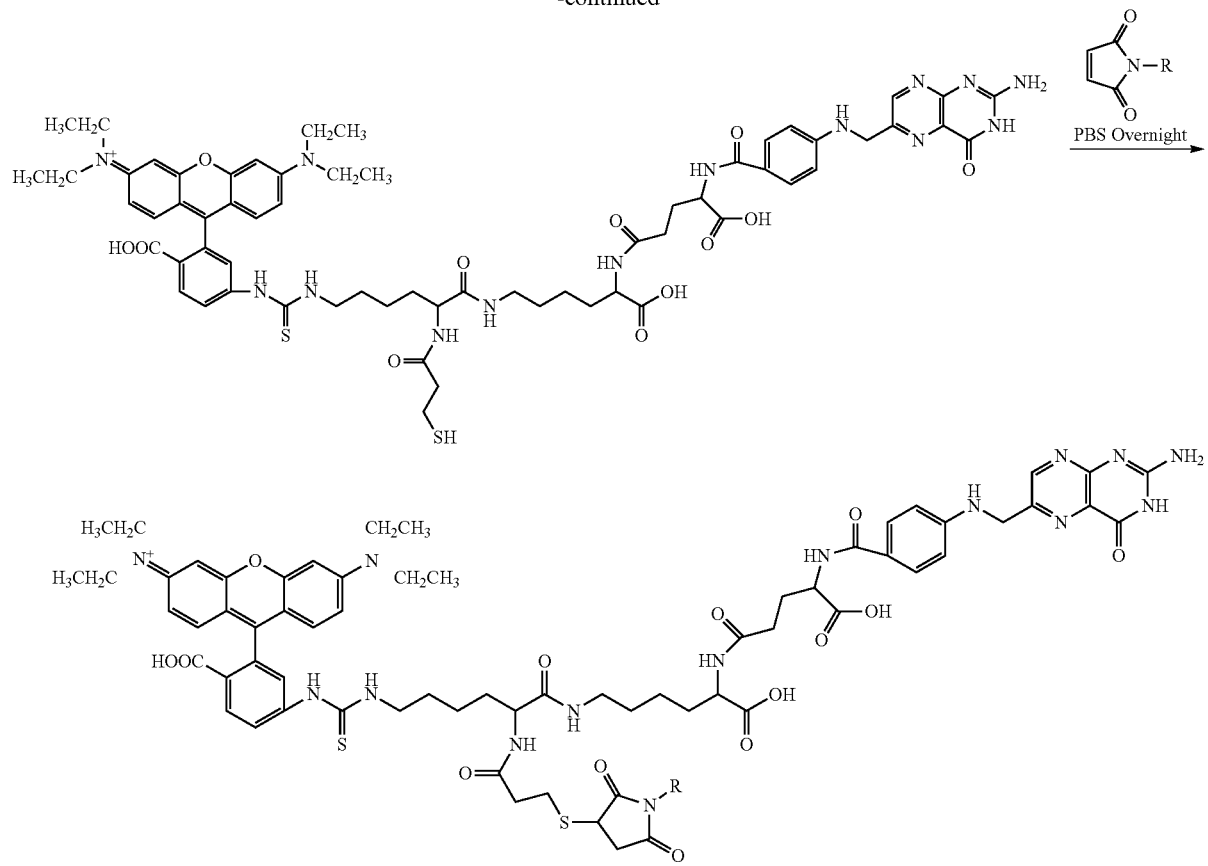

a) piperidine, DMF; b) Fmoc-Glu-OtBu (1), HOBt, HBTU, DIPEA, DMF; c) Pteroic acid (2), HOBt, HBTU, DIPEA, DMF; d) 1% TFA, CH$_2$Cl$_2$; e) Fmoc-Lys(Mtt)-OH (3), HOBT, HBTU, DIPEA, DMF; f) S-Trityl-3-mercaptopropionic acid (4), HOBT, HBTU, DIPEA, DMF; g) Rhodamine-ITC (5), DIPEA; h) 94.5% TFA, 2.5% H$_2$O, 2.5% EDT; 1% TIS; i) NH$_4$OH.

In the preceding scheme, R represents the following:

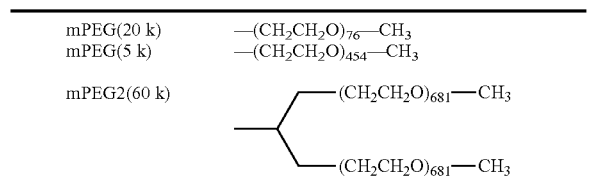

| | |
|---|---|
| mPEG(20 k) | —(CH$_2$CH$_2$O)$_{76}$—CH$_3$ |
| mPEG(5 k) | —(CH$_2$CH$_2$O)$_{454}$—CH$_3$ |
| mPEG2(60 k) | (CH$_2$CH$_2$O)$_{681}$—CH$_3$ / (CH$_2$CH$_2$O)$_{681}$—CH$_3$ |

Synthesis of Folate-Rhodamine-Sh as a Peg-Anchor

Standard Fmoc peptide chemistry was used to synthesize a folate linked to Rhodamine B-isothiocyanate via a spacer composed of two lysines attached to the γ-COOH terminal of folic acid. The sequence Lys-Lys-(γ)Glu-pteroic acid was constructed by Fmoc chemistry with HBTU and HOBT (Novabiochem, San Diego, Calif.) as the activating agents along with diisopropyethylamine (DIPEA) as the base. The Fmoc groups were deprotected with 20% piperidine in dimethylformamide (DMF). α-Fmoc-protected lysine-loaded Wang resin, containing a 4-methyltrityl protecting group on the ε-amine, was used as an anchor for folate. An Fmoc-Glu-OtBu was linked to the α-amine of the lysine to provide a γ-linked conjugate of folate after N$^{10}$-trifluoroacetylpteroic acid (SIGMA, St. Louis, Mo.) was attached to the glutamic acid amine. The methoxytrityl (Mtt) protecting group on the ε-amine of lysine was removed with 1% trifluoroacetic acid in dichloromethane to allow attachment of a second Fmoc-Lys(Mtt)-OH. After removing the Mtt-protecting group of the second lysine, S-Trityl-protected 3-mecaptopropionic acid was coupled to the α-amine of the second lysine, using the coupling reagents, HOBT and HBTU as described above. Finally, the Mtt-protecting group of the second lysine was removed and Rhodamine-B isothiocyanate (SIGMA, St. Louis, Mo.) dissolved in DMF was reacted overnight with the peptide in the presence of DIPEA, and then washed thoroughly from the peptide resin beads. The resin was washed several times with dichloromethane, and methanol and left to dry under N$_2$ for several hours. The folate-Lys-Lys-mercaptopropionic acid-rhodamine peptide was then cleaved from the resin with 95% TFA/2.5 H$_2$O/2.5% TIS/2.5% EDT solution for 3-4 hours. Ice cold diethyl ether was used to precipitate the product, and the precipitant was collected by centrifugation. The product was then washed three times with diethyl ether and dried under vacuum. To remove the N$^{10}$-trifluoracetyl protecting group from the folate moiety, the product was dissolved in 10% ammonium hydroxide solution and stirred for 30 min at room temperature under argon to prevent disulfide bonds from forming. The product was then lyophilized until dry and stored under argon. The product was confirmed by mass spectroscopic analysis ([M$^-$] calculated, 1286.5. found, 1285.08).

Synthesis of Folate-Peg(5K)-Rhodamine, Folate-Peg(20K)-Rhodamine, and Folate-Peg(60K)-Rhodamine The folate-rhodamine-SH anchor, synthesized as described above, was used to react with maleimide-activated PEG(5 k), PEG(20 k), or PEG(60 k) (Nektar Therapeutics, San Carlos, Calif.). The PEG-MAL molecules were dissolved in PBS and a 5-fold molar excess of folate-rhodamine-SH was added to the solution and stirred overnight, at room temperature, under nitrogen. The non-reacted folate-rhodamine was then separated from the folate-PEG-rhodamine conjugate by gel filtration chromatography, using a coarse Sephadex G-50 column equilibrated in water, (fractionation range for globular proteins: 1,500-30,000, SIGMA, St. Louis, Mo.), and using gravity for running the samples. The folate-PEG-rhodamine peak was collected, lyophilized and re-suspended in phosphate buffered saline (PBS) for animal studies.

Characterization of the Molecular Weight of Folate-Peg-Rhodamine Conjugates

In order to characterize the apparent molecular weight of the folate-PEG-rhodamine conjugates, their $V_e/V_o$ ratio was compared with the $V_e/V_o$ of protein standards of known molecular weight ($V_e$ is the elution volume, and $V_o$ is the void volume). Columns were run in phosphate buffered saline (PBS, pH 7.4), at room temperature, at a flow rate of 5 ml/min. The void volume of the column ($V_o$) was determined spectrophotometrically by the elution volume for blue dextran (molecular weight approx. 2,000,000, SIGMA, St. Loius, Mo.) at 610 nm, by measuring the volume of effluent collected from the point of sample application to the center of the effluent peak. Individual protein standards were dissolved in the PBS and their elution time was followed by absorbance readings at 280 nm. The elution volume ($V_e$) of the protein standards was determined by measuring the volume of effluent collected from the point of sample application to the center of the effluent peak. In order to determine the $V_e$ of the folate-PEG-rhodamine conjugates, samples were applied on the column and ran at the same flow rate as used for blue dextran and the protein standards. The $V_e$ of the folate-PEG-rhodamine conjugates was determined using the same method applied to the standards. Plotting the logarithms of the known molecular weights of protein standards versus their respective $V_e/V_o$ values produces a linear calibration curve. Two different Sephacryl HR columns were used for the purpose of resolving all the folate-PEG-conjugates. A 24 cm×1.0 cm Sephacryl 100-HR (MW range 1000-10,000 Da) was able to resolve the folate-PEG(5 k)-rhodamine conjugate, but not the folate-PEG(20 k)-rhodamine and folate-PEG(60 k)-rhodamine conjugates. The latter two conjugates were resolved on a 22 cm×1.0 cm Sephacryl 200-HR (MW range 5-250 kDa). The protein standards used on the Sephacryl 100-HR were: bradykinin fragment 2-9 (MW ~904), aprotinin from bovine lung (MW 6,511.44), myoglobin from horse heart (MW ~17,000), carbonic anhydrase from bovine erythrocytes (MW ~29,000), albumin (MW ~66,000), aldolase (MW ~161,000). The protein standards used on Sephacryl 200-HR were: myoglobin from horse heart (MW ~17,000), carbonic anhydrase from bovine erythrocytes (MW ~29,000), albumin (MW ~66,000), alcohol dehydrogenase from yeast (MW ~150,000), β-amylase from sweet potato (MW ~200,000), apoferritin from horse spleen (MW ~443,000), bovine thyroglobulin (MW ~669,000).

Characterization of Folate/Rhodamine Ratio for Folate-Peg-Rhodamine Conjugates

In order to determine the ratio of folate to rhodamine on all the folate-PEG-rhodamine conjugates, first the extinction coefficients of folic acid and rhodamine-isothiocyanate in water were determined at two different wavelengths, 280 nm and 560 nm, by constructing standard curves at both these wavelengths. The slopes of these standard curves correspond to the extinction coefficients of folic acid and rhodamine-isothiocyanate in water. Samples of folate-PEG-rhodamine conjugates were then dissolved in water and their absorbances 280 nm and 560 nm were measured. The absorbances of folate-PEG-rhodamine conjugates at these wavelengths are due to both, the absorbance of folic acid (FA) and rhodamine (Rhod), therefore:

$$A_{280}=A_{280}(FA)+A_{280}(Rhod) \text{ and } A_{560}=A_{560}(FA)+A_{560}(Rhod)$$

By using the extinction coefficients of folic acid (FA) and rhodamine (Rhod), determined by the standard curves, the concentrations of folate and rhodamine, and thus their ratio, in each folate-PEG-rhodamine conjugate sample can be determined by simultaneously solving for their respective concentrations in the following equations:

$$A_{280}=\epsilon_{280}(FA) \cdot 1 \cdot c(FA) + \epsilon_{280}(Rhod) \cdot 1 \cdot c(Rhod)$$

$$A_{560}=\epsilon_{560}(FA) \cdot 1 \cdot c(FA) + \epsilon_{560}(Rhod) \cdot 1 \cdot c(Rhod)$$

Example 29

Synthesis of Folate Cw800

$N^{10}$-TFA-Pteroic acid was synthesized as reported elsewhere. First, Fmoc-Lys(Mtt)-Wang resin was swelled in DMF for 20 min. The deprotection of Fmoc group on the resin was achieved by 20% piperidine in DMF. 2.5 e.q. Fmoc-(γ) Glu-OtBu, HOBT, HBTU and 4 e.q. DIPEA were added to the reaction. Two hours later, the Fmoc group on glutamic acid was deprotected with 20% piperidine. Then, 2.5 e.q. $N^{10}$-TFA-Pteroic acid, HOBT and HBTU were dissolved in 3:1 DMF/DMSO and 4 e.q. DIPEA were added to the reaction and reacted for 4 h. The product was washed with DMF, DCM and methanol. 1% TFA/DCM was used to cleave the Mtt protection group. Cleavage of the conjugates was achieved by TFA:TIPS:$H_2O$ (95:2.5:2.5). The crude product was then precipitated with cool ether. The crude product was then hydrolyzed with ammonium hydroxide (pH=10) for 20 min. Folate-lysine was purified by HPLC and characterized by MS and NMR. Folate-lysine and CW 800 succinimidyl ester (1:1) were stirred in 0.1 M carbonate buffer (pH 9.0) in the dark for 18 h. The folate-CW800 conjugates was purified by HPLC and characterized by MS and NMR.

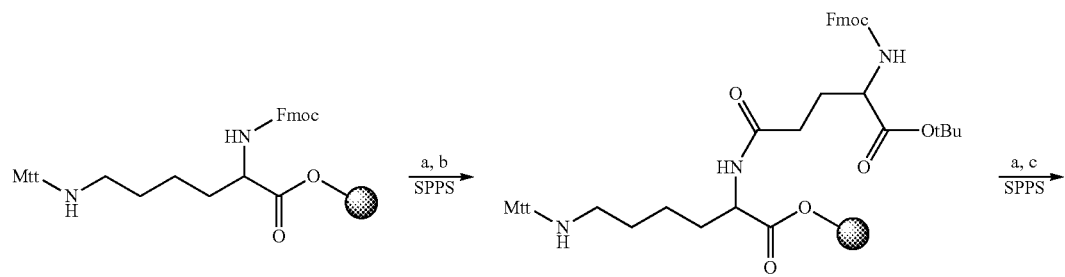
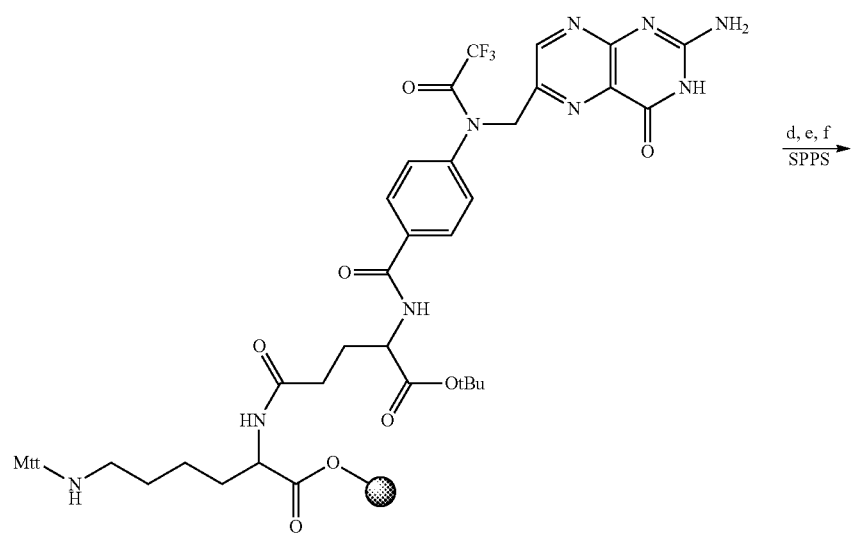
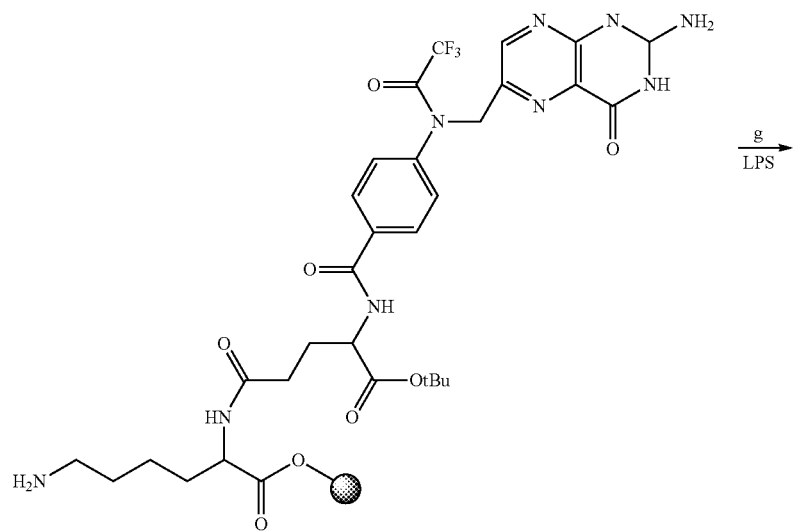

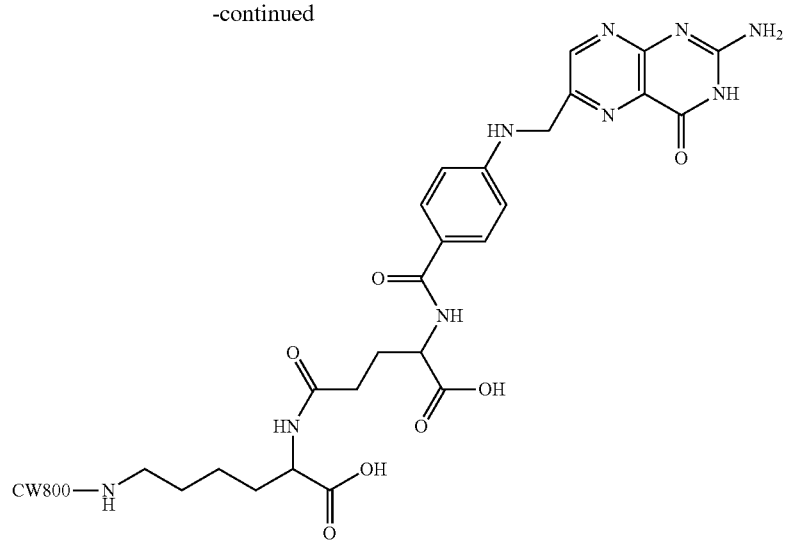
a) 20% piperidine/DMF b) Fmoc-GluOtBu(1)/HOBt/HBTU/DIPEA/DMF c) $N^{10}$-*tfa*-pteroic HOBt/HBTU/DIPEA/DMF d) 1% TFA/DCM e) 95% TFA/2.5% $H_2O$/2.5% TIPS f) 10% NH CW800/DIPEA/DMSO
Example 30
Synthesis of Folate Alexafluor 647
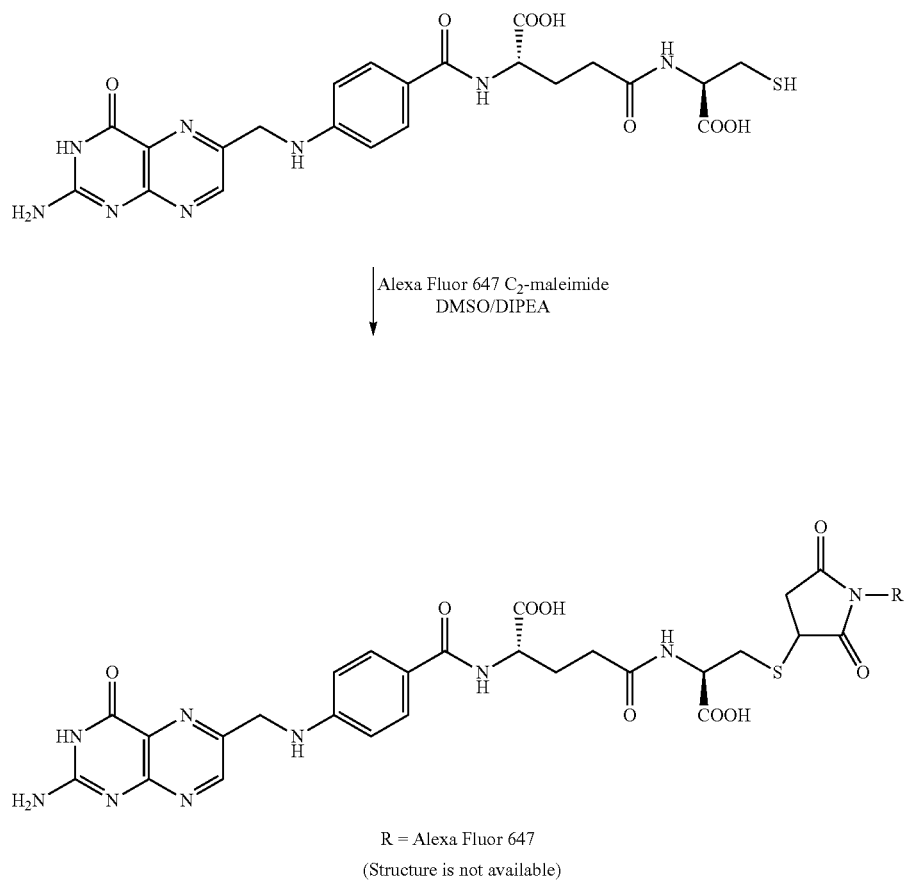
R = Alexa Fluor 647
(Structure is not available)

First, H-Cys(Trt)-2-Cl Trt resin was swelled in DMF for 20 min. The deprotection of Fmoc group on the resin was achieved with 20% piperidine in DMF. 2.5 e.q. Fmoc-(γ)Glu-OtBu, HOBT, HBTU and 4 e.q. DIPEA were added to the reaction. Two hours later, the Fmoc group on glutamic acid was deprotected with 20% piperidine. Then, 2.5 e.q. $N^{10}$-TFA-Pteroic acid, HOBT and HBTU were dissolved in 3:1 DMF/DMSO and 4 e.q. DIPEA were added to the reaction and reacted for 4 h. The product was washed with DMF, DCM and methanol. Cleavage of the conjugates was achieved with TFA:TIPS:$H_2O$ (95:2.5:2.5). The crude product was then precipitated with cool ether. The crude product was hydrolyzed with ammonium hydroxide (pH=10) for 20 min. Folate-cysteine was purified by HPLC and characterized by MS and NMR. Folate-cysteine and ALEXAFLUOR 647 maleimide (1:1) were coupled in DMSO in the dark for 18 h. The folate-ALEXAFLUOR 647 conjugate was purified by HPLC and characterized by MS and NMR.

Example 31

Synthesis of Folate-EDA-Rhodamine

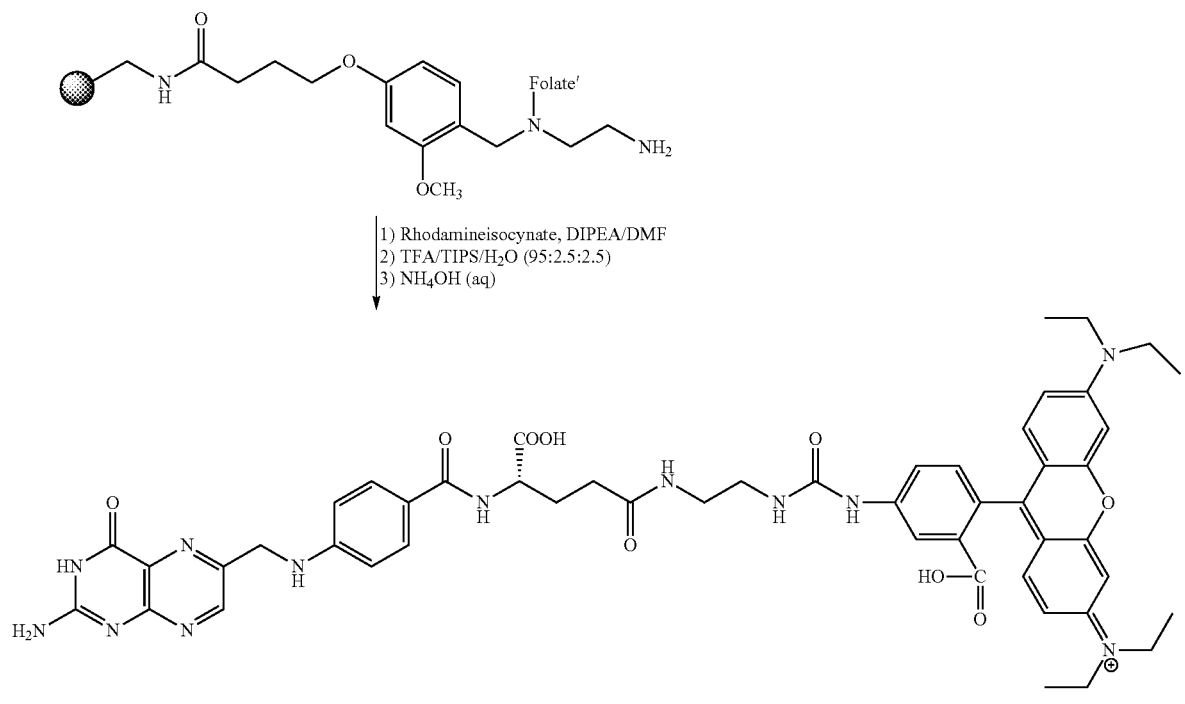

Folate-EDA-Tetramethylrhodamine

Example 32

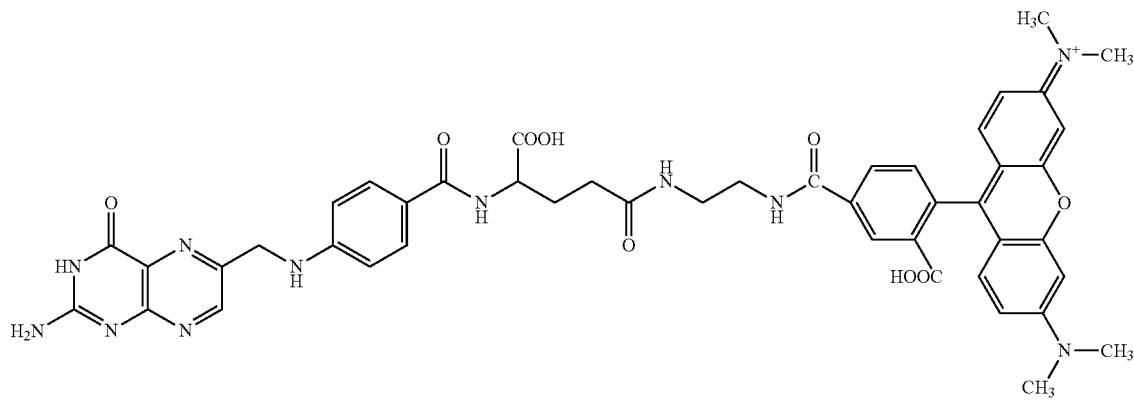 [SMILES: CN(C)c1ccc2c(-c3ccc(C(=O)NCCNC(=O)CCC(NC(=O)c4ccc(NCc5cnc6nc(N)[nH]c(=O)c6n5)cc4)C(=O)O)cc3C(=O)O)c3ccc(=[N+](C)C)cc-3oc2c1]

Folate-EDA-tetramethylrhodamine was prepared according to the process described above for Example 34.
Example 33
Synthesis of Folate-Lys-Rhodamine
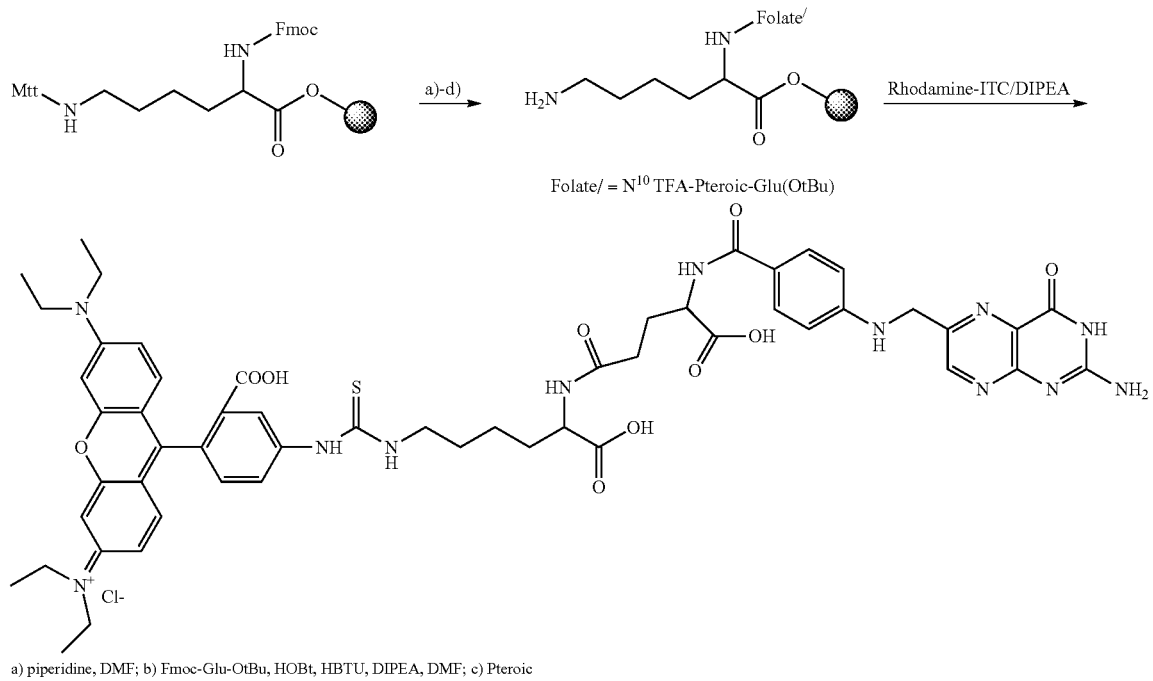
a) piperidine, DMF; b) Fmoc-Glu-OtBu, HOBt, HBTU, DIPEA, DMF; c) Pteroic acid, HOBt, HBTU, DIPEA, DMF; d) 1% TFA, DCM.
Example 34
Synthesis of Folate-Alexafluor 488
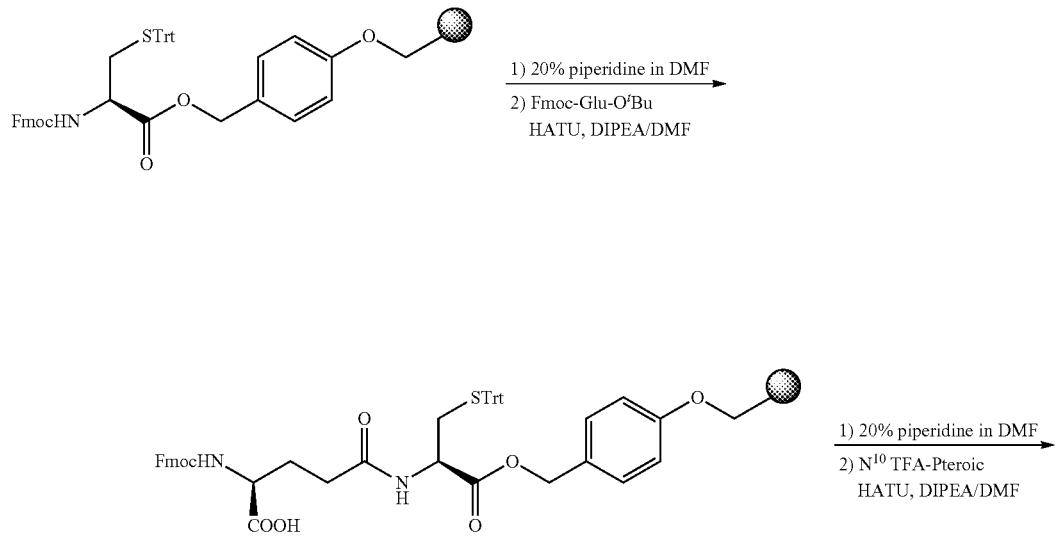

-continued

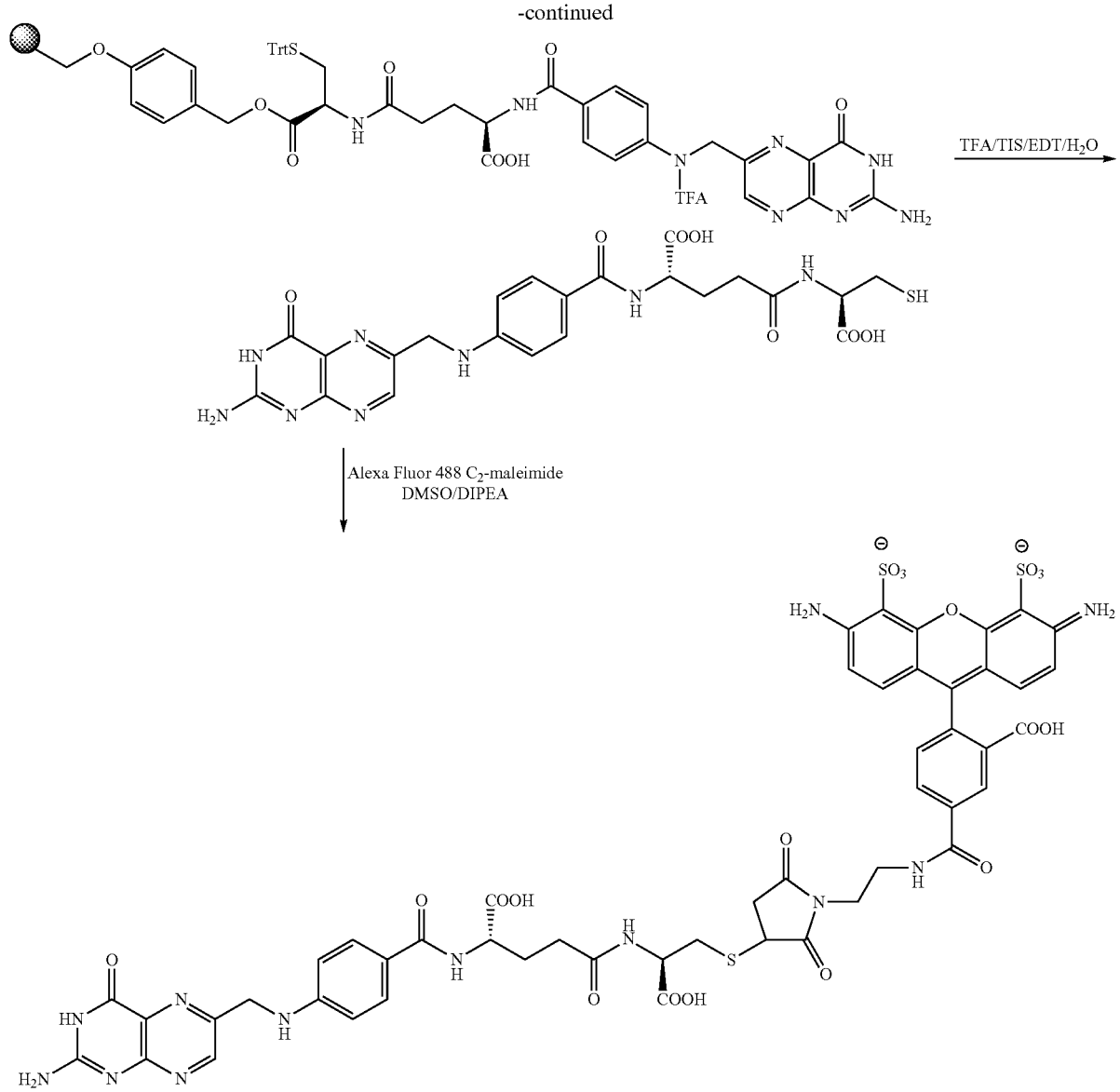

It is to be understood that the foregoing Examples are merely illustrative of the compounds described herein and additional compounds may be prepared as described herein by the appropriate selection the starting materials, including the dye or fluorescent agent.

What is claimed is:

1. A method of detecting an imaging agent bound to pathogenic cells comprising the steps of:
   (i) combining 1) an ex vivo patient sample comprising the pathogenic cells collected from a patient, wherein the ex vivo patient sample is a body fluid of the patient, and 2) a composition comprising a conjugate of the formula $A_b\text{-}X$ wherein X is the imaging agent, wherein the imaging agent emits a detectable signal, and
   wherein $A_b$ comprises a prostate-specific membrane antigen binding ligand, and wherein the prostate-specific membrane antigen binding ligand binds to the prostate-specific membrane antigen on the pathogenic cells; and
   (ii) detecting, using flow cytometry, the signal from the imaging agent moiety of the conjugate that is bound to the pathogenic cells, and wherein the conjugate of the formula $A_b$-X in the method allows quantitation of the pathogenic cells at about 1 to about 10 cells per two milliliters of the ex vivo patient sample.

2. The method of claim 1 wherein the body fluid is selected from the group consisting of spinal fluid, lymph fluid, urine, mucus, and blood.

3. The method of claim 1 wherein the pathogenic cells are cancer cells.

4. The method of claim 3 wherein the cancer cells are metastatic cancer cells.

5. The method of claim 1 wherein the imaging agent comprises a chromophore.

6. The method of claim 5 wherein the chromophore is a fluorescent chromophore.

7. The method of claim 6 wherein the chromophore is selected from the group consisting of fluorescein, OREGON GREEN®, rhodamine, phycoerythrin, TEXAS RED®, DYLIGHT®, and ALEXAFLUOR®.

8. The method of claim 6 wherein the fluorescent chromophore is group X of $A_b$-X, and $A_b$-X is selected from the group consisting of folate-fluorescein, folate-OREGON GREEN®, folate-rhodamine, folate-phycoerythrin, folate-cys-TEXAS RED®, folate-ALEXAFLUOR®, and folate-DYLIGHT®.

9. The method of claim 6 wherein the chromophore comprises a compound of the general structure

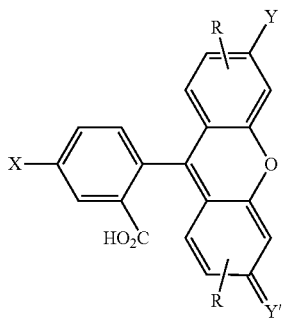

wherein X is oxygen, nitrogen, or sulfur, and where X is attached to linker L; Y is $OR^a$, $NR^a_2$, or $NR_3^{a+}$; and Y' is O, $NR^a$, or $NR_2^{a+}$; where each R is independently selected in each instance from H, fluoro, sulfonic acid, sulfonate, and salts thereof; and $R^a$ is hydrogen or alkyl.

10. The method of claim 6 wherein the chromophore comprises a compound of the general structure

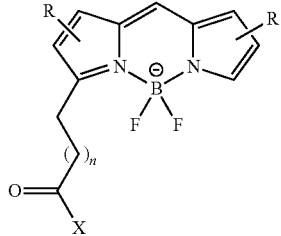

wherein X is oxygen, nitrogen, or sulfur, and where X is attached to linker L; each R is independently selected from H, alkyl, and heteroalkyl; and n is an integer from 0 to about 4.

11. The method of claim 1 wherein said pathogenic cells are detected using multiphoton flow cytometry.

12. The method of claim 1 wherein $A_b$-X is in a composition that comprises a pharmaceutically acceptable carrier.

13. The method of claim 1 wherein $A_b$-X has a linker of at least 7 atoms.

14. The method of claim 1 wherein the patient is a human patient.

15. The method of claim 1 wherein the patient is a veterinary patient.

16. The method of claim 1 wherein the group $A_b$ comprises a prostate-specific membrane antigen binding ligand of the structure:

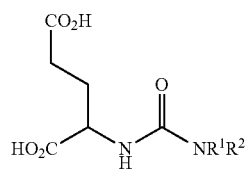

wherein $R^1$ and $R^2$ are each selected from hydrogen, optionally substituted carboxylic acids, such as thiolacetic acids, thiolpropionic acids, malonic acids, succinic acids, glutamic acids, and adipic acids.

17. The method of claim 1 wherein $A_b$ comprises a prostate-specific membrane antigen binding ligand selected from the group consisting of

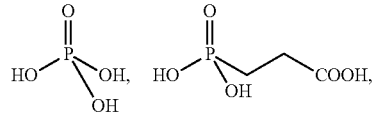

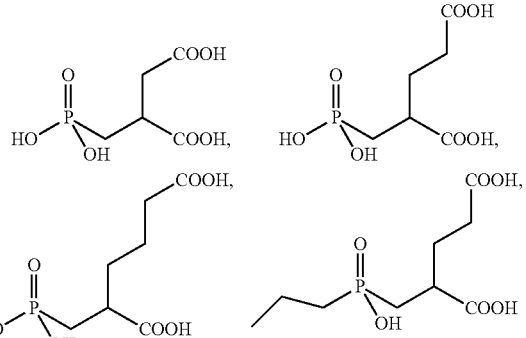

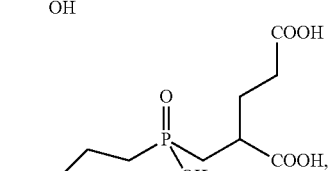

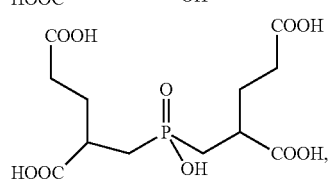

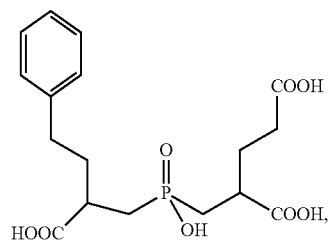

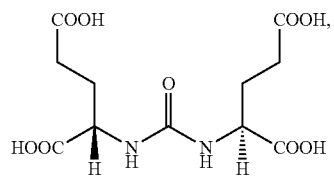 [SMILES: O=C(O)CC[C@H](NC(=O)N[C@@H](CCC(=O)O)C(=O)O)C(=O)O]

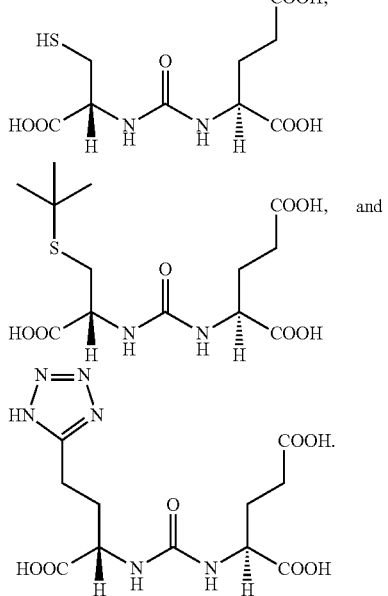
18. The method of claim 17 wherein the prostate-specific membrane antigen binding ligand has the formula
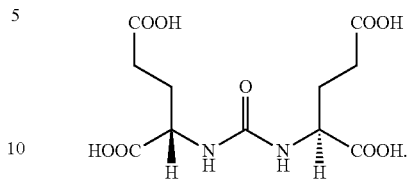
19. The method of claim 17 wherein the prostate-specific membrane antigen binding ligand has the formula
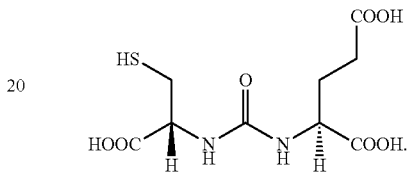
* * * * *